US008551453B2

(12) United States Patent
Raymond et al.

(10) Patent No.: US 8,551,453 B2
(45) Date of Patent: Oct. 8, 2013

(54) AROMATIC TRIAMIDE-LANTHANIDE COMPLEXES

(75) Inventors: Kenneth N. Raymond, Berkeley, CA (US); Stephane Petoud, Pittsburgh, PA (US); Jide Xu, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 832 days.

(21) Appl. No.: 10/585,178

(22) PCT Filed: Dec. 29, 2004

(86) PCT No.: PCT/US2004/043968
§ 371 (c)(1),
(2), (4) Date: Oct. 3, 2008

(87) PCT Pub. No.: WO2006/001835
PCT Pub. Date: Jan. 5, 2006

(65) Prior Publication Data
US 2009/0036537 A1  Feb. 5, 2009

Related U.S. Application Data

(60) Provisional application No. 60/533,482, filed on Dec. 30, 2003.

(51) Int. Cl.
*A61K 49/00* (2006.01)

(52) U.S. Cl.
USPC ......... 424/9.6; 424/1.11; 424/1.65; 424/1.69; 424/1.73; 424/9.1

(58) Field of Classification Search
USPC ........... 424/1.11, 1.49, 1.65, 1.69, 1.73, 1.81, 424/1.85, 1.89, 9.1, 9.2, 9.6; 534/7, 10–16; 514/1, 1.1; 530/300, 333, 334, 338, 530/343, 350
See application file for complete search history.

(56) References Cited

U.S. PATENT DOCUMENTS

| | | | | |
|---|---|---|---|---|
| 2,977,332 | A | * | 3/1961 | Zumstein .................... 528/111.3 |
| 4,748,184 | A | * | 5/1988 | Stout et al. .................... 514/422 |
| 4,855,225 | A | | 8/1989 | Fung et al. |
| 5,047,519 | A | | 9/1991 | Hobbs, Jr. et al. |
| 5,049,280 | A | | 9/1991 | Raymond et al. |
| 5,252,462 | A | | 10/1993 | Drevin et al. |
| 5,470,896 | A | | 11/1995 | Wegmann et al. |
| 5,820,849 | A | | 10/1998 | Schmitt-Willich et al. |
| 5,989,823 | A | | 11/1999 | Jayasena et al. |
| 6,406,297 | B1 | | 6/2002 | Raymond et al. |
| 6,515,113 | B2 | | 2/2003 | Raymond et al. |
| 6,864,103 | B2 | | 3/2005 | Raymond et al. |
| 7,018,850 | B2 | | 3/2006 | Raymond et al. |
| 7,442,558 | B2 | | 10/2008 | Raymond et al. |
| 2002/0128451 | A1 | | 9/2002 | Raymond et al. |
| 2002/0188111 | A1 | | 12/2002 | Raymond et al. |
| 2005/0058604 | A1 | | 3/2005 | Raymond et al. |
| 2008/0213780 | A1 | | 9/2008 | Butlin et al. |
| 2008/0213917 | A1 | | 9/2008 | Raymond et al. |
| 2009/0023928 | A1 | | 1/2009 | Raymond et al. |
| 2010/0151591 | A1 | | 6/2010 | Butlin et al. |
| 2010/0167289 | A1 | | 7/2010 | Butlin et al. |

FOREIGN PATENT DOCUMENTS

| | | |
|---|---|---|
| CA | 2099542 | 7/1993 |
| EP | 0578067 | 6/1993 |
| WO | WO/89/11475 | 11/1989 |
| WO | WO 92/11039 | 7/1992 |
| WO | WO 97/45539 | 4/1997 |
| WO | WO 00/48991 | 8/2000 |
| WO | WO 2008/063721 | 5/2008 |
| WO | WO 2008/092120 | 7/2008 |

OTHER PUBLICATIONS

Lichtenberger et al (Bulletin de la Societe Chimique de France, 1963, pp. 275-282).*
Blomberg, et al., "Terbium and rhodamine as labels in a homogeneous time resolved fluorometric energy transfer assay of the βsubunit of human chorionic gonadotropin in serum", *Clinical Cehmistry*, 45(6):855-861 (1999).
Brooker, S. et al., Chemical Abstract 2002: 593344 (2002).
Bünzli, et al., "Towards materials with planned properties : dinuclear f-f helicates and d-f non-convalent podates based on benzimidazole-pyridine binding units", *Journal of Alloys and Compounds*, 249:14-24 (1997).
Cardullo, R. et al., "Detection of nucleic acid hybridization by nonradiative fluorescence resonance energy transfer", *Proc. Natl. Acad. Sci. USA* 85:8790-8794 (1988).
Chen, et al., "Lifetime- and color-tailored fluorophores in the micro-to-millisecond time regime", *J. Am. Chem. Soc.*, 122(4):657-660 (2000).
Dahlén "Detection of Biotinylated DNA Probes by Using Eu-Labeled Streptavidin and Time-Resolved Fluorometry" *Anal. Biochem.*, 164:78-83 (1987).
De Sá, et al., "Spectroscopic properties and design of highly luminescent lanthanide coordination complexes", *Coordination Chemistry Reviews*, 196:165-195 (2000).
Dexter, D.L., "A Theory of Sensitized Luminescence in Solids", *Journal of Chemical Physics* 21: 836-850 (1953).
Dickins, et al., "Synthesis, time-resolved luminescence, NMR spectroscopy, circular dichroism and circularly polarised luminescence studies f enantiopure macrocyclic lanthanide tetraamide complexes", *Chem. Eur. J.*, 5(3):1095-1105 (1999).

(Continued)

*Primary Examiner* — D L Jones
(74) *Attorney, Agent, or Firm* — Morgan, Lewis & Bockius LLP; Jeffry S. Mann; Todd Esker

(57) ABSTRACT

The present invention provides luminescent lanthanide metal chelates comprising a metal ion of the lanthanide series and a complexing agent comprising at least one phthalamidyl moiety. Also provided are probes incorporating the phthalamidyl ligands of the invention and methods utilizing the ligands of the invention and probes comprising the ligands of the invention.

43 Claims, 7 Drawing Sheets

(56) References Cited

OTHER PUBLICATIONS

Dickson, et al., "Time-resolved detection of lanthanide luminescence of ultrasensitive bioanalytical assays", *Journal of Photochemistry and Photobiology*, B: Biology, 27:3-19 (1995).

Galaup, et al., "Mono(di)nuclear eropium(III) complexes of macrobi(tri)cyclic cryptands derived from diazatetralactams as luminophores in aqueous solution", *Helvetica Chimica Acta*, 82:543-560 (1999).

Heid, C. et al., "Real time quantitative PCR", *Genome Res.* 6:986-994 (1996).

Hemmilä, et al., "Development of luminescent lanthanide chelate labels for diagnostic assays", *Journal of Alloys and Compounds*, 249:158-162 (1997).

Higuchi, R. et al., "Simultaneous Amplification and Detection of Specific DNA Sequences", *Bio/Technology* 10:413-417 (1992).

Hochstrasser, R. et al., "Distance distribution in a dye-linked oligonucleotide dtermined by time-resolved fluorescence energy transfer", *Biophysical Chemistry* 45:133-141 (1992).

Holland, P. et al., "Detection of specific polymerase chain reaction product by utilizing the 5'→3' exonuclease activity of *Thermus aquaticus* DNA polymerase", *Proc. Nat. Acad. Sci. USA*, 88:7276-7280 (1991).

Johansson et al., "Time Gating Improves Sensitivity in Energy Transfer Assays with Terbium Chelate/Dark Quencher Oligonucleotide Probes" *J. Am. Chem. Soc.*, 126(50): 16451-16455 (2004).

Knight, C.G., "Fluorimetric Assays of Proteolytic Enzymes", *Methods in Enzymology* 248: 18-34 (1995).

Kostrikis, L. et al., "Spectral Genotyping of Human Alleles", *Science* 279:1228-1229 (1998).

Lee, L. et al., "Allelic discrimination by nick-translation PCR with fluorogenic probes", *Nucleic Acids Res.* 21:3761-3766 (1993).

Lee, L. G. et al., "Seven-Color, Homogeneous Detection of Six PCR Products" *Bio Techniques* 27:342-349 (1999).

Nazarenko, I.A. et al., "A closed tube format for amplification and detection of DNA based on energy transfer", *Nucleic Acids Res.* 25:2516-2521 (1997).

Ost, H., *Journal Prakt. Chem.* 2:110-111 (1876).

Petoud et al., "Stable Lanthanide Luminescence Agents Highly Emissive in Aqueous Solution: Multidentate 2-Hydroxyisophthalamide Complexes of $Sm^{3+}$, $Eu^{3+}$, $Tb^{3+}$, $Dy^{3+}$" *J. Am. Chem. Soc.*, 125: 13354-13325 (2003).

Sabbatini, et al., "Luminescent lanthanide complexes as photochemical supramolecular devices", *Coordination Chemistry Reviews*, 123:201-228 (1993).

Saha, et al., "Time-resolved fluorescence of a new europium chelate complex: Demonstration of highly sensitive detection of protein and DNA samples", *J. Am. Chem. Soc.*, 115:11032-11032 (1993).

Selvin, P., "Fluorescence Resonance Energy Transfer", *Methods in Enzymology* 246:300-334 (1995).

Sequoia, E., "Complexes of Lanthanide Perchlorates", *Inorganica Chimica Acta*, 37:1 L-449-L451 (1979).

Soini, et al., "Time-resolved fluorescence of lanthanide probes and applications in biotechnology", *CRC Critical Reviews in Analytical Chemistry*, 18(2):105-154 (1987).

Steemers, et al., "Water-soluble neutral calix[4]arene-lathanide complexes: Synthesis and luminescence properties", *J. Org. Chem.*, 62:4229-4235 (1997).

Steinberg, I., "Long-Range Nonradiative Transfer of Electronic Excitation Energy in Proteins and Polypeptides", *Ann. Rev. Biochem.* 40:83-114 (1971).

Stenroos, et al., "Homogeneous time-resolved IL-2IL-Rα assay using fluorescence resonance energy transfere", *Cytokine* 10(7):495-499 (Jul. 1998).

Stryer, L., "Fluorescence Energy Transfer as a Spectroscopic Ruler", *Ann. Rev. Biochem.* 47:819-846 (1978).

Syvänen et al., "Time-resolved fluorometry: a sensitive method to quantify DNA-hybrids" *Nucleic Acids Research*, 14:1017-1028 (1986).

Tyagi, S. et al., "Molecular Beacons: Probes that Fluoresce upon Hybridization", *Nature Biotechnology* 14: 303-308 (1996).

Tyagi, S. et al., "Multicolor molecular beacons for allele discrimination", *Nature Biotechnology* 16:49-53 (1998).

Veiopoulou, et al., "Comparative study of fluorescent ternary terbium complexes. Application in enzyme amplified fluorimetric immunoassay for α-fetoprotein", *Analytica Chimica Acta*, 335:177-184 (1996).

Vicentini, et al., "Luminescence and structure of europium compounds", *Coordination Chemistry Reviews*, 196:353-382 (2000).

Voss, H. et al., "Direct genomic fluorescent on-line sequencing and analysis using in vivo amplification of DNA", *Nucleic Acids Research* 17:2517 (1989).

Wang, G. et al., "Design and Synthesis of New Fluorogenic HIV Protease Substrates Based on Resonance Energy Transfer", *Tetrahedron Letters* 31: 6493-6496 (1990).

Wang, Y. et al., "Rapid Sizing of Short Tandem Repeat Alleles Using Capillary Array Electrophoresis and Energy-Transfer Fluorescent Primers", *Anal. Chem.* 67:1197-1203 (1995).

Whitcombe, D. et al., "Detection of PCR products using self-probing amplicons and fluorescence", *Nature Biotechnology* 17:804-807 (1999).

\* cited by examiner

ABSTRACT
AROMATIC TRIAMIDE-LANTHANIDE COMPLEXES

CROSS-REFERENCE TO RELATED APPLICATIONS

The present application is a U.S. national phase application of PCT Application No. PCT/US2004/43968, filed Dec. 29, 2004, and claims priority to U.S. Provisional Patent Application 60/533,482 filed on Dec. 30, 2003, the disclosures of which are incorporated herein by reference, in their entirety, for all purposes.

STATEMENT AS TO RIGHTS TO INVENTIONS MADE UNDER FEDERALLY SPONSORED RESEARCH AND DEVELOPMENT

This invention was made with government support under DK032999 awarded by the National Institutes of Health and under DE-AC03-76F00098 awarded by the Department of Energy. The government has certain rights in the invention.

BACKGROUND OF THE INVENTION

There is a continuing and expanding need for rapid, highly specific methods of detecting and quantifying chemical, biochemical and biological substances as analytes in research and diagnostic mixtures. Of particular value are methods for measuring small quantities of proteins, nucleic acids, peptides, pharmaceuticals, metabolites, microorganisms and other materials of diagnostic value. Examples of such materials include small molecular bioactive materials (e.g., narcotics and poisons, drugs administered for therapeutic purposes, hormones), pathogenic microorganisms and viruses, antibodies, and enzymes and nucleic acids, particularly those implicated in disease states.

The presence of a particular analyte can often be determined by binding methods that exploit the high degree of specificity, which characterizes many biochemical and biological systems. Frequently used methods are based on, for example, antigen-antibody systems, nucleic acid hybridization techniques, and protein-ligand systems. In these methods, the existence of a complex of diagnostic value is typically indicated by the presence or absence of an observable "label" which has been attached to one or more of the interacting materials. The specific labeling method chosen often dictates the usefulness and versatility of a particular system for detecting an analyte of interest. Preferred labels are inexpensive, safe, and capable of being attached efficiently to a wide variety of chemical, biochemical, and biological materials without significantly altering the important binding characteristics of those materials. The label should give a highly characteristic signal, and should be rarely, and preferably never, found in nature. The label should be stable and detectable in aqueous systems over periods of time ranging up to months. Detection of the label is preferably rapid, sensitive, and reproducible without the need for expensive, specialized facilities or the need for special precautions to protect personnel. Quantification of the label is preferably relatively independent of variables such as temperature and the composition of the mixture to be assayed.

A wide variety of labels have been developed, each with particular advantages and disadvantages. For example, radioactive labels are quite versatile, and can be detected at very low concentrations, such labels are, however, expensive, hazardous, and their use requires sophisticated equipment and trained personnel. Thus, there is wide interest in non-radioactive labels, particularly in labels that are observable by spectrophotometric, spin resonance, and luminescence techniques, and reactive materials, such as enzymes that produce such molecules.

Labels that are detectable using fluorescence spectroscopy are of particular interest, because of the large number of such labels that are known in the art. Moreover, the literature is replete with syntheses of fluorescent labels that are derivatized to allow their facile attachment to other molecules, and many such fluorescent labels are commercially available.

In addition to being directly detected, many fluorescent labels operate to quench or amplify the fluorescence of an adjacent second fluorescent label. Because of its dependence on the distance and the magnitude of the interaction between the quencher and the fluorophore, the quenching of a fluorescent species provides a sensitive probe of molecular conformation and binding, or other, interactions. An excellent example of the use of fluorescent reporter quencher pairs is found in the detection and analysis of nucleic acids.

An alternative detection scheme, which is theoretically more sensitive than autoradiography, is time-resolved fluorimetry. According to this method, a chelated lanthanide metal with a long radiative lifetime is attached to a molecule of interest. Pulsed excitation combined with a gated detection system allows for effective discrimination against short-lived background emission. For example, using this approach, the detection and quantification of DNA hybrids via an europium-labeled antibody has been demonstrated (Syvanen et al., *Nucleic Acids Research* 14: 1017-1028 (1986)). In addition, biotinylated DNA was measured in microtiter wells using Eu-labeled streptavidin (Dahlen, *Anal. Biochem,* 164: 78-83 (1982)). A disadvantage, however, of these types of assays is that the label must be washed from the probe and its fluorescence developed in an enhancement solution. A further drawback has been the fact that the fluorescence produced has only been in the nanosecond (ns) range, a generally unacceptably short period for adequate detection of the labeled molecules and for discrimination from background fluorescence.

In view of the predictable practical advantages it has been generally desired that the lanthanide chelates employed should exhibit a delayed fluorescence with decay times of more than 10 µs. The fluorescence of many of the known fluorescent chelates tends to be inhibited by water. As water is generally present in an assay, particularly an immunoassay system, lanthanide complexes that undergo inhibition of fluorescence in the presence of water are viewed as somewhat unfavorable or impractical for many applications. Moreover, the short fluorescence decay times is considered a disadvantage of these compounds. This inhibition is due to the affinity of the lanthanide ions for coordinating water molecules. When the lanthanide ion has coordinated water molecules, the absorbed light energy (excitation energy) is transferred from the complex to the solvent rather than being emitted as fluorescence.

Thus, lanthanide chelates, particularly coordinatively saturated chelates having excellent luminescence properties are highly desirable. In the alternative, coordinatively unsaturated lanthanide chelates that exhibit acceptable luminescence in the presence of water are also advantageous. Such chelates that are derivatized to allow their conjugation to one or more components of an assay, find use in a range of different assay formats. The present invention provides these and other such compounds and assays using these compounds.

SUMMARY OF THE INVENTION

Luminescent (including fluorescent, phosphorescent and emission arising from metal ions) markers find a wide variety of applications in science, medicine and engineering. In many situations, these markers provide competitive replacements for radiolabels, chromogens, radiation-dense dyes, etc. Moreover, improvements in fluorimetric instrumentation have increased attainable sensitivities and permitted quantitative analysis.

Lanthanide chelates in combination with time-resolved fluorescent spectroscopy is a generally accepted analytical, e.g., immunochemical tool. Lanthanide ions generally used in analytical procedures include $Dy^{3+}$, $Sm^{3+}$, $Tb^{3+}$, $Er^{3+}$ and $Eu^{3+}$, $Nd^{3+}$, $Tm^{3+}$, $Yb^{3+}$. Other lanthanide ions, such as $La^{3+}$, $Gd^{3+}$ and $Lu^{3+}$ are useful, but generally less preferred.

The present invention provides lanthanide complexes that are extremely luminescent and possess many features desired for luminescent markers and probes of use in fluorescent assay systems. Among these advantages are: 1) ligands acting as both chelators and chromophore/energy transfer devices; 2) very high quantum yields of lanthanide ion luminescence of the present complexes in water without external augmentation, such as by micelles or fluoride; 3) high stability and solubility of these complexes in water; 4) an extremely easy synthesis that employs inexpensive starting materials; and 5) facile access to many derivatives for linking these luminescent probes to, for example, an immunoreactive agent or solid support (e.g., polymer).

The present invention provides a new class of lanthanide-complexing ligands that incorporate derivatives of 2-hydroxy-benzene-1,3,5-tricarboxylic acid (3). The tricarboxylic acid is a known compound (Ost, *J. Prakt. Chem.* 2: 110-111 (1876)); the numbering of the aromatic ring is shown below. Although this acid has been known for more than one hundred years, its triamides (3A) have not been reported. The present invention also provides chelating agents and complexes that include the diamides (4).

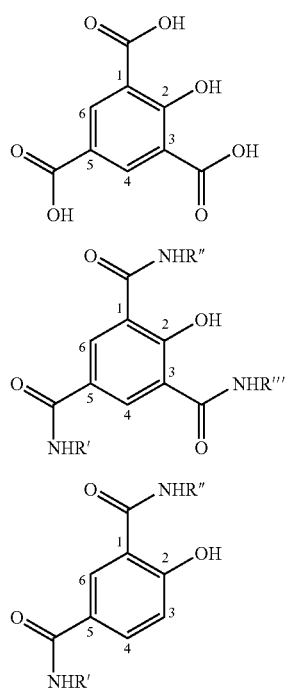

The compounds of the invention include bidentate, tridentate, tetradentate and other higher polydentate ligands. The compounds of the invention are easily prepared in good yields.

Thus, in a first aspect, the present invention provides a compound according to Formula I:

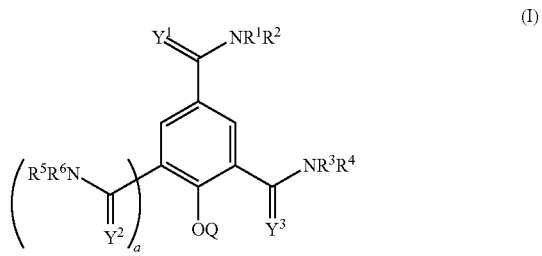

wherein the symbols $R^1$, $R^2$, $R^3$, $R^4$, $R^5$ and $R^6$ represent members independently selected from H, substituted or unsubstituted alkyl, substituted or unsubstituted heteroalkyl, substituted or unsubstituted aryl, and substituted or unsubstituted heterocycloalkyl. One or more member selected from $R^1$ and $R^2$; $R^3$ and $R^4$; and $R^5$ and $R^6$, together with the nitrogen atom to which they are attached, optionally form a ring system selected from substituted or unsubstituted heteroaryl and substituted or unsubstituted heterocycloalkyl. $Y^1$, $Y^2$ and $Y^3$ are members independently selected from O and $(H)_2$. The symbol Q represents a member selected from H, a protecting group and a cleaveable group. The symbol "a" represents the integer 0 or 1. Also provided are lanthanide complexes of the ligands of the invention, particularly luminescent lanthanide complexes.

In addition to the ligands and lanthanide complexes, the present invention also provides a number of methods, including assays utilizing the compounds of the invention. The assays of the invention preferably utilize the fluorescence of the compounds described herein to detect the subject of the assay. The methods of the invention allow the detection of, for example, small molecular bioactive materials and biomolecules at trace concentrations without using radioactive species.

Other objects advantages and aspects of the present invention will be apparent from the detailed description that follows.

BRIEF DESCRIPTION OF THE DRAWINGS

FIG. 4 Calculated species distribution from pH=3 to pH=9 of complexes of the invention.

DETAILED DESCRIPTION OF THE INVENTION AND THE PREFERRED EMBODIMENTS

Abbreviations

Figure 1A:
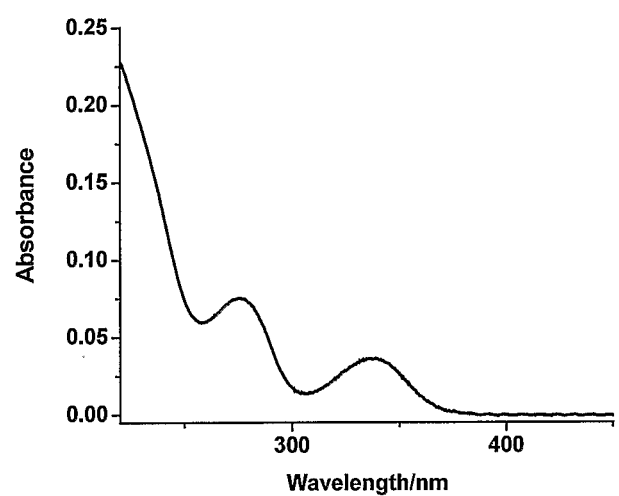
FIG. 1 Absorption spectra of aqueous solutions of the Tb complexes formed with the ligands H22MeTIAM (9A) (FIG. 1A) and H22tetra3LITIAM (9G) (FIG. 1B).

As used herein, "TIAM" refers to 2-hydroxy-benzene-1,3, 5-tricarboxylamide chelators (e.g., 3A) and metal complexes of the chelators. "TIAM" refers to both the ligands and the metal complexes of the invention. The discussion herein regarding "TIAM" chelators is also relevant to the analogous dicarboxylic amide chelators "DIAM" of the invention. Representative DIAM are compounds according to Formula I, in which a is equal to 0.

Definitions

Unless defined otherwise, all technical and scientific terms used herein generally have the same meaning as commonly understood by one of ordinary skill in the art to which this invention belongs. Generally, the nomenclature used herein and the laboratory procedures in molecular biology, organic chemistry and nucleic acid chemistry and hybridization described below are those well known and commonly employed in the art. The nomenclature used herein and the laboratory procedures in analytical chemistry, and organic synthetic described below are those known and employed in the art. Standard techniques, or modifications thereof, are used for chemical syntheses and chemical analyses.

"Analyte", as used herein, means any compound or molecule of interest for which a diagnostic test is performed, such as a biopolymer or a small molecular bioactive material. An analyte can be, for example, a protein, peptide, carbohydrate, polysaccharide, glycoprotein, hormone, receptor, antigen, antibody, virus, substrate, metabolite, transition state analog, cofactor, inhibitor, drug, dye, nutrient, growth factor, etc., without limitation.

As used herein, "energy transfer" refers to the process by which the fluorescence emission of a fluorescent group is altered by a fluorescence-modifying group. If the fluorescence-modifying group is a quenching group, then the fluorescence emission from the fluorescent group is attenuated (quenched). Energy transfer can occur through fluorescence resonance energy transfer, or through direct energy transfer. The exact energy transfer mechanisms in these two cases are different. It is to be understood that any reference to energy transfer in the instant application encompasses all of these phenomena.

As used herein, "energy transfer pair" refers to any two molecules that participate in energy transfer. Typically, one of the molecules acts as a fluorescent group, and the other acts as a fluorescence-modifying group. The preferred energy transfer pair of the instant invention comprises a fluorescent group and a quenching group of the invention. There is no limitation on the identity of the individual members of the energy transfer pair in this application. All that is required is that the spectroscopic properties of the energy transfer pair as a whole change in some measurable way if the distance between the individual members is altered by some critical amount.

"Energy transfer pair" is used to refer to a group of molecules that form a single complex within which energy transfer occurs. Such complexes may comprise, for example, two fluorescent groups, which may be different from one another and one quenching group, two quenching groups and one fluorescent group, or multiple fluorescent groups and multiple quenching groups. In cases where there are multiple fluorescent groups and/or multiple quenching groups, the individual groups may be different from one another.

As used herein, "fluorescence-modifying group" refers to a molecule of the invention that can alter in any way the fluorescence emission from a fluorescent group. A fluorescence-modifying group generally accomplishes this through an energy transfer mechanism. Depending on the identity of the fluorescence-modifying group, the fluorescence emission can undergo a number of alterations, including, but not limited to, attenuation, complete quenching, enhancement, a shift in wavelength, a shift in polarity, and a change in fluorescence lifetime. One example of a fluorescence-modifying group is a quenching group.

"Fluorescence resonance energy transfer" or "FRET" is used interchangeably with FET, and refers to an energy transfer phenomenon in which the light emitted by the excited fluorescent group is absorbed at least partially by a fluorescence-modifying group of the invention. If the fluorescence-modifying group is a quenching group, then that group will preferably not radiate a substantial fraction of the absorbed light as light of a different wavelength, and will preferably dissipate it as heat. FRET depends on an overlap between the emission spectrum of the fluorescent group and the absorption spectrum of the quenching group. FRET also depends on the distance between the quenching group and the fluorescent group.

As used herein, "fluorophore" refers to a fluorescent species other than a TIAM (DIAM) complex of the invention.

As used herein, "nucleic acid" means DNA, RNA, single-stranded, double-stranded, or more highly aggregated hybridization motifs, and any chemical modifications thereof. Modifications include, but are not limited to, those providing chemical groups that incorporate additional charge, polarizability, hydrogen bonding, electrostatic interaction, and fluxionality to the nucleic acid ligand bases or to the nucleic acid ligand as a whole. Such modifications include, but are not limited to, peptide nucleic acids, phosphodiester group modifications (e.g., phosphorothioates, methylphosphonates), 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases, isocytidine and isoguanidine and the like. Modifications can also include 3' and 5' modifications such as capping with a PL, a fluorophore or another moiety.

As used herein, "quenching group" refers to any fluorescence-modifying group of the invention that can attenuate at least partly the light emitted by a fluorescent group. This attenuation is referred to herein as "quenching". Hence, illumination of the fluorescent group in the presence of the quenching group leads to an emission signal that is less intense than expected, or even completely absent. Quenching typically occurs through energy transfer between the fluorescent group and the quenching group.

"Peptide" refers to a polymer in which the monomers are amino acids and are joined together through amide bonds, alternatively referred to as a polypeptide. When the amino acids are □-amino acids, either the L-optical isomer or the D-optical isomer can be used. Additionally, unnatural amino acids, for example, □-alanine, phenylglycine and homoarginine are also included. Commonly encountered amino acids that are not gene-encoded may also be used in the present invention. All of the amino acids used in the present invention may be either the D- or L-isomer. The L-isomers are generally preferred. In addition, other peptidomimetics are also useful in the present invention. For a general review, see, Spatola, A. F., in CHEMISTRY AND BIOCHEMISTRY OF AMINO ACIDS, PEPTIDES AND PROTEINS, B. Weinstein, eds., Marcel Dekker, New York, p. 267 (1983).

"Reactive functional group," as used herein refers to groups including, but not limited to, olefins, acetylenes, alcohols, phenols, ethers, oxides, halides, aldehydes, ketones, carboxylic acids, esters, amides, cyanates, isocyanates, thiocyanates, isothiocyanates, amines, hydrazines, hydrazones, hydrazides, diazo, diazonium, nitro, nitriles, mercaptans, sulfides, disulfides, sulfoxides, sulfones, sulfonic acids, sulfinic acids, acetals, ketals, anhydrides, sulfates, sulfenic acids isonitriles, amidines, imides, imidates, nitrones, hydroxylamines, oximes, hydroxamic acids thiohydroxamic acids, allenes, ortho esters, sulfites, enamines, ynamines, ureas, pseudoureas, semicarbazides, carbodiimides, carbamates, imines, azides, azo compounds, azoxy compounds, and nitroso compounds. Reactive functional groups also include those used to prepare bioconjugates, e.g., N-hydroxysuccinimide esters, maleimides and the like. Methods to prepare each of these functional groups are well known in the art and their application to or modification for a particular purpose is within the ability of one of skill in the art (see, for example, Sandler and Karo, eds. ORGANIC FUNCTIONAL GROUP PREPARATIONS, Academic Press, San Diego, 1989).

"Non-covalent protein binding groups" are moieties that interact with an intact or denatured polypeptide in an associative manner. The interaction may be either reversible or irreversible in a biological milieu. The incorporation of a "non-covalent protein binding group" into a chelating agent or complex of the invention provides the agent or complex with the ability to interact with a polypeptide in a non-covalent manner. Exemplary non-covalent interactions include hydrophobic-hydrophobic and electrostatic interactions. Exemplary "non-covalent protein binding groups" include anionic groups, e.g., phosphate, thiophosphate, phosphonate, carboxylate, boronate, sulfate, sulfone, sulfonate, thiosulfate, and thiosulfonate.

As used herein, "linking member" refers to a covalent chemical bond that includes at least one heteroatom. Exemplary linking members include —C(O)NH—, —C(O)O—, —NH—, —S—, —O—, and the like.

The term "targeting group" is intended to mean a moiety that is: (1) able to direct the entity to which it is attached (e.g., therapeutic agent or marker) to a target cell, for example, to a specific type of tumor cell; or (2) is preferentially activated at a target tissue, for example a tumor. The targeting group can be a small molecule, which is intended to include both non-peptides and peptides. The targeting group can also be a macromolecule, which includes saccharides, lectins, receptors, ligand for receptors, proteins such as BSA, antibodies, and so forth.

The symbol , whether utilized as a bond or displayed perpendicular to a bond indicates the point at which the displayed moiety is attached to the remainder of the molecule, solid support, etc.

Certain compounds of the present invention exist in unsolvated forms as well as solvated forms, including hydrated forms. The solvated forms are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention.

The compounds of the invention may be prepared as a single isomer (e.g., enantiomer, cis-trans, positional, diastereomer) or as a mixture of isomers. In a preferred embodiment, the compounds are prepared as substantially a single isomer. Methods of preparing substantially isomerically pure compounds are known in the art. For example, enantiomerically enriched mixtures and pure enantiomeric compounds can be prepared by using synthetic intermediates that are enantiomerically pure in combination with reactions that either leave the stereochemistry at a chiral center unchanged or result in its complete inversion. Alternatively, the final product or intermediates along the synthetic route can be resolved into a single stereoisomer. Techniques for inverting or leaving unchanged a particular stereocenter, and those for resolving mixtures of stereoisomers are well known in the art and it is well within the ability of one of skill in the art to choose and appropriate method for a particular situation. See, generally, Furniss et al. (eds.), VOGEL's ENCYCLOPEDIA OF PRACTICAL ORGANIC CHEMISTRY 5$^{TH}$ ED., Longman Scientific and Technical Ltd., Essex, 1991, pp. 809-816; and Heller, Acc. Chem. Res. 23: 128 (1990).

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

Where substituent groups are specified by their conventional chemical formulae, written from left to right, they equally encompass the chemically identical substituents, which would result from writing the structure from right to left, e.g., —CH$_2$O— is intended to also recite —OCH$_2$—.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. C$_1$-C$_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups, which are limited to hydrocarbon groups are termed "homoalkyl".

The term "alkylene" by itself or as part of another substituent means a divalent radical derived from an alkane, as exemplified, but not limited, by —CH$_2$CH$_2$CH$_2$CH$_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. Up to two heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo(C$_1$-C$_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, hydrocarbon substituent, which can be a single ring or multiple rings (preferably from 1 to 3 rings), which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents-described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") is meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$ in a number ranging from zero to (2 m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: halogen, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R'" and R"" are preferably independently selected from hydrogen, (C$_1$-C$_8$)alkyl and heteroalkyl, unsubstituted aryl and heteroaryl, (unsubstituted aryl)-(C$_1$-C$_4$)alkyl, and (unsubstituted aryl)oxy-(C$_1$-C$_4$)alkyl. When a compound of the invention includes more than one R group, for example, each of the R groups is independently selected as are each R', R", R'" and R"" groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R''')$_d$—, where s and d are independently integers of from 0 to 3, and X is —O—, —NR'—, —S—, —S(O)—, —S(O)$_2$—, or —S(O)$_2$NR'—. The substituents R, R', R" and R''' are preferably independently selected from hydrogen or substituted or unsubstituted (C$_1$-C$_6$)alkyl.

As used herein, the term "heteroatom" is meant to include oxygen (O), nitrogen (N), sulfur (S) and silicon (Si).

Introduction

The present invention provides a class of luminescent probes that are based on metal chelates of amides (mono-, di- and tri-amides) of 2-hydroxy-benzene-1,3,5-tricarboxylic acid-based ligands, and of 2-hydroxy-benzene-1,5-dicarboxylic acid-based ligands. Exemplary amides include the triamide of 2-hydroxy-benzene-1,3,5-tricarboxylic acid ("TIAM"), and the diamide of 2-hydroxy-benzene-1,5-dicarboxylic acid ("DIAM"). Other compounds of the invention include TIAM and other chelating groups, e.g., phthalamidyl, catecholamidyl, terephthalamidyl and salicylamidyl moieties, in a single ligand. The compounds of the invention emit light or they can be used to absorb light emitted by a reporter fluorophore. The fluorophores of the invention can be used as small molecules in solution assays or they can be utilized as a label that is attached to an analyte or a species that interacts with, and allows detection and/or quantification of an analyte.

The invention also provides metal chelates of the ligands of the invention, e.g., chelates of ions of the lanthanide series, particularly luminescent chelates.

Fluorescent labels have the advantage of requiring few precautions in their handling, and being amenable to high-throughput visualization techniques (optical analysis including digitization of the image for analysis in an integrated system comprising a computer). Preferred labels are typically characterized by high sensitivity, high stability, low background, long lifetimes, low environmental sensitivity and high specificity in labeling.

The fluorophores of the invention can also be used in conjunction with other fluorophores or quenchers as components of energy transfer probes. Many fluorescent labels are useful in combination with the chelators of the invention. Many such labels are commercially available and, if it not readily available commercially, will be able to synthesize the necessary fluorophore de novo or synthetically modify commercially available fluorescent compounds to arrive at the desired fluorescent label.

In addition to small molecule fluorophores, naturally occurring fluorescent proteins and engineered analogues of such proteins are useful with the TIAM ligands and complexes of the present invention. Such proteins include, for example, green fluorescent proteins of cnidarians (Ward et al., *Photochem. Photobiol.* 35:803-808 (1982); Levine et al., *Comp. Biochem. Physiol.*, 72B:77-85 (1982)), yellow fluorescent protein from Vibrio *fischeri* strain (Baldwin et al., *Biochemistry* 29:5509-15 (1990)), Peridinin-chlorophyll from the dinoflagellate Symbiodinium sp. (Morris et al., *Plant Molecular Biology* 24:673:77 (1994)), phycobiliproteins from marine cyanobacteria, such as Synechococcus, e.g., phycoerythrin and phycocyanin (Wilbanks et al., *J. Biol. Chem.* 268:1226-35 (1993)), and the like.

The compounds of the invention can be used as probes, as tools for separating particular ions from other solutes, as probes in microscopy, enzymology, clinical chemistry, molecular biology and medicine. The compounds of the invention are also useful as therapeutic agents in modalities, such as photodynamic therapy and as diagnostic agents in imaging methods, such as magnetic resonance imaging. Moreover, the compounds of the invention are useful as components of optical amplifiers of light, waveguides and the like. Furthermore, the compounds of the invention can be incorporated into inks and dyes, such as those used in the printing of currency or other negotiable instruments.

The compounds of the invention can be made to luminesce by exciting them in any manner known in the art, including, for example, with light or electrochemical energy (see, for example, Kulmala et al, *Analytica Chimica Acta* 386: 1 (1999)). The luminescence can, in the case of chiral compounds of the invention, be circularly polarized (see, for example, Riehl et al., *Chem. Rev.* 86: 1 (1986)).

The compounds, probes and methods discussed in the following sections are generally representative of the compositions of the invention and the methods in which such compositions can be used. The following discussion is intended as illustrative of selected aspects and embodiments of the present invention and it should not be interpreted as limiting the scope of the present invention.

The Compounds

The amides of the present invention are exemplified by reference to 2-hydroxy-benzene-1,3,5-tricarboxylamide-based metal chelating ligands ("TIAM") and the analogous diamines ("DIAM") that include at least one TIAM moiety within their framework. The focus of the discussion on these species is for clarity of illustration.

In a first aspect, the invention provides, a compound having the formula:

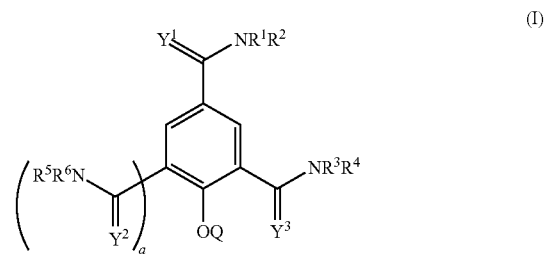

(I)

wherein the symbols R$^1$, R$^2$, R$^3$, R$^4$, R$^5$ and R$^6$ represent members independently selected from H, substituted or unsubstituted alkyl, substituted or unsubstituted heteroalkyl, substituted or unsubstituted aryl, and substituted or unsubstituted heterocycloalkyl. One or more member selected from R$^1$ and R$^2$; R$^3$ and R$^4$; and R$^5$ and R$^6$, together with the nitrogen atom to which they are attached, optionally form a ring system selected from substituted or unsubstituted heteroaryl and substituted or unsubstituted heterocycloalkyl. Y$^1$, Y$^2$ and Y$^3$ are members independently selected from O and (H)$_2$. The symbol Q represents a member selected from H, a protecting group and a cleaveable group. The symbol "a" represents the integer 0 or 1. Also provided are lanthanide complexes of the ligands of the invention, particularly luminescent lanthanide complexes.

Dicarboxylic acid amide (DIAM) ligands of the invention are those compounds according to Formula I in which a is zero.

The TIAM group(s) of the chelating ligand can be substituted with one or more electron-withdrawing and/or electron-donating group. Those of skill in the art understand which substituents, when appended to an aromatic ring will exhibit electron withdrawing or electron donating properties. Tables of substituents that are appropriate for inclusion in the chelators of the invention can be found in the literature. See, for example, Hammett, *J. Am. Chem. Soc.* 59: 96 (1937); Johnson, THE HAMMETT EQUATION, Cambridge University Press, New York, 1973; Hansch et al., *J. Med. Chem.* 16: 1207 (1973); and Hansch et al., SUBSTITUENT CONSTANTS FOR CORRELATION ANALYSIS IN CHEMISTRY AND BIOLOGY, Wiley, New York, 1979.

In other embodiments substituents on the TIAM group or on the backbone to which the TIAM group is attached are fluorescence sensitizers. Exemplary sensitizers include rhodamine 560, 575 and 590 fluoresceins, 2- or 4-quinolones, 2 or 4-coumarins, or derivatives thereof e.g. coumarin 445, 450, 490, 500 and 503, 4-trifluoromethylcoumarin (TFC), 7-diethyl-amino-cumarin-3-carbohyddzide, etc., and especially carbostyril 124 (7-amino-4-methyl-2-quinolone), coumarin 120 (7-amino-4-methyl-2-coumarin), coumarin 124 (7-amino-4-(trifluoromethyl)-2-coumarin), aminomethyltrimethylpsoralen, napthalene and the like.

In a preferred embodiment, the sensitizer is a moiety that comprises a napthyl moiety The TIAM groups of the chelating ligand can also be functionalized with one or more linker moieties, linking the TIAM to a group, through which the TIAM may optionally be tethered to another species. Exemplary species include carrier molecules, targeting agents and backbones through which the TIAM is connected with another chelating moiety. Thus, in an exemplary embodiment, the invention provides a compound according to Formula I, wherein a member selected from $R^1$, $R^3$ and $R^5$ has the structure:

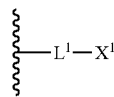

in which $L^1$ is a member selected from substituted or unsubstituted alkyl, substituted or unsubstituted heteroalkyl and substituted or unsubstituted aryl; and $X^1$ is a member selected from protected or unprotected reactive functional groups and non-covalent protein binding groups.

Exemplary $L^1$-$X^1$ groups include:

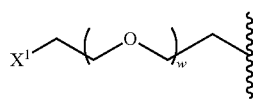 and 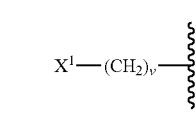

in which $X^1$ is a member selected from

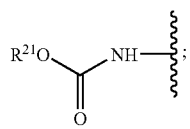 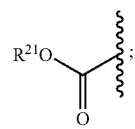 and

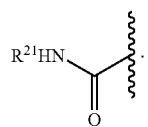

The symbol $R^{21}$ represents H, substituted or unsubstituted alkyl or substituted or unsubstituted aryl. The symbol v represents an integer from 1 to 20; and w represents an integer from 1 to 1,000.

Further exemplary triamide-$L^1$-$X^1$ species include:

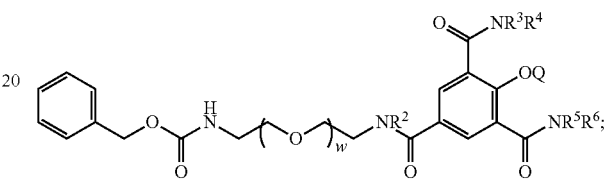

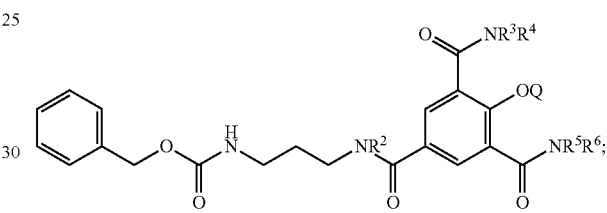

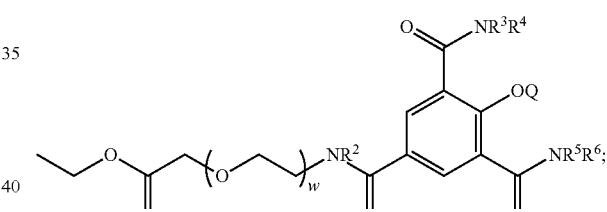

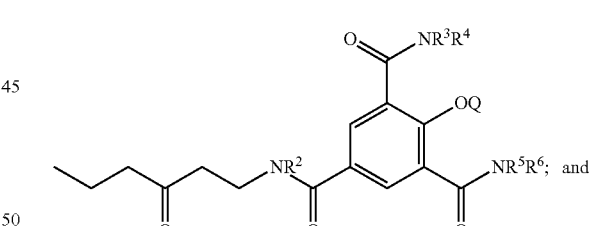

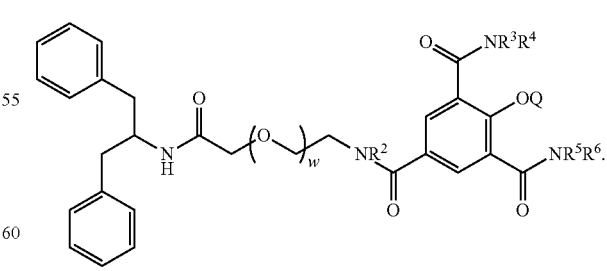

In another exemplary embodiment, the invention provides a compound according to Formula II:

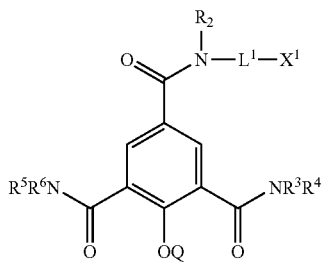

(II)

in which $X^1$ is selected from a reactive functional group or a moiety that includes a reactive functional group, e.g., $NH_2$, SH, $COR^7$, $O(CH_2)_mZ^6$, $NHNH_2$ and $O(CH_2)_2(OCH_2CH_2)_sO(CH_2)_2Z^6$. The symbol $R^7$ represents a member selected from H, $OR^8$, $OCOR^8$, and $NR^8R^9$. $R^8$ and $R^9$ are members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl. The symbol $Z^6$ represents $OR^{10}$, $OCOR^{10}$, or $NR^{10}R^{11}$, in which $R^{10}$ and $R^{11}$ are members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl. The symbol "m" represents an integer from 1 to 20; and s is an integer from 1 to 1000.

In yet another exemplary embodiment, the invention provides a compound according to Formula III:

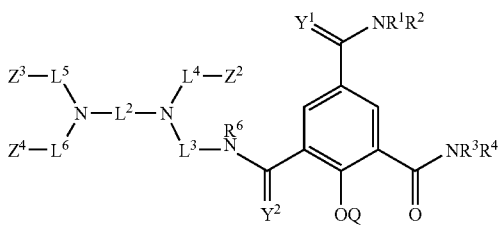

(III)

in which $L^2$ is a member selected from substituted or unsubstituted alkyl, substituted or unsubstituted heteroalkyl, substituted or unsubstituted aryl, substituted or unsubstituted heteroaryl, substituted or unsubstituted heterocycloalkyl. The symbols $L^3$, $L^4$, $L^5$ and $L^6$ represent members independently selected from a single bond, substituted or unsubstituted alkyl and substituted or unsubstituted heteroalkyl. In an exemplary embodiment, $L^2$ is a substituted or unsubstituted $C_1$-$C_6$ alkyl group. $Z^2$, $Z^3$, and $Z^4$ are members independently selected from H, substituted or unsubstituted aryl and substituted or unsubstituted heteroaryl. Exemplary species for $Z^2$, $Z^3$, and $Z^4$ include alkyl, e.g., $CH_2$, substituted with one or more OH (or O—), COOH (or COO—), phosphate, and the like.

Further exemplary moieties for $Z^2$, $Z^3$, and $Z^4$ include substituted or unsubstituted pyridyl, substituted or unsubstituted salicylamidyl, substituted or unsubstituted phthalamidyl, substituted or unsubstituted terephthalamidyl, substituted or unsubstituted catecholamidyl and

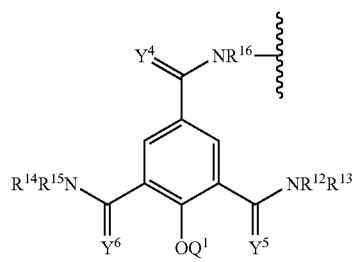

wherein the symbols $R^{12}$, $R^{13}$, $R^{14}$, $R^{15}$ and $R^{16}$ represent members independently selected from H, substituted or unsubstituted alkyl, substituted or unsubstituted heteroalkyl, substituted or unsubstituted aryl, and substituted or unsubstituted heterocycloalkyl, wherein one or more member selected from $R^7$ and $R^8$; and $R^9$ and $R^{10}$, together with the nitrogen atom to which they are attached, optionally form a ring system selected from heteroaryl and heterocycloalkyl. $Y^4$, $Y^5$ and $Y^6$ are members independently selected from O and $(H)_2$; and Q is a member selected from H, a protecting group or a cleaveable group. Other exemplary structures according to the invention are:

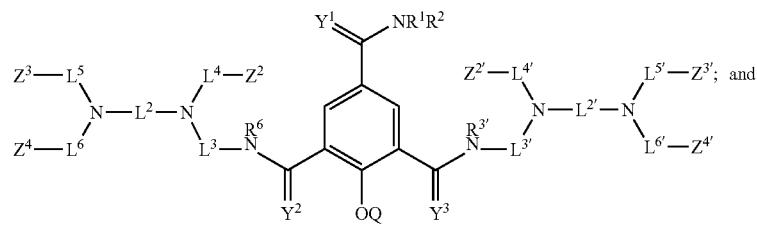

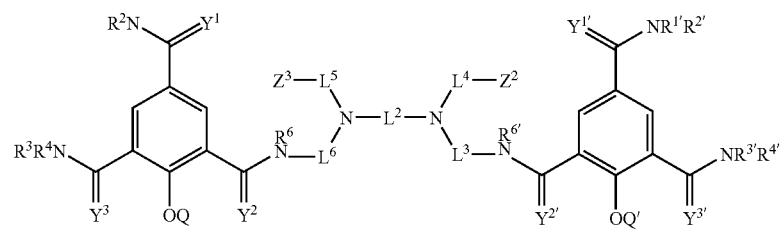

in which the identities of the primed radicals are identical to those discussed above in the context of the non-primed radicals: the identities of the primed and non-primed radicals in the structures immediately above are independently selected.

In another exemplary embodiment, the chelators used in conjunction with the TIAM are aminocarboxylates (i.e. EDTA, DTPA, DOTA, NTA, HDTA, TETA, TTHA etc. and their phosphonate analogs such as DTPP, EDTP, HDTP, NTP, etc), crown ethers, cryptands and the like. Thus, for example, $L^2$ is selected to provide the desired chelating agent. In an exemplary embodiment, the chelating agent is DTPA and $L^2$ has the formula:

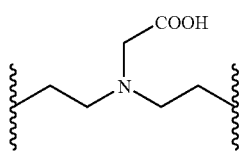 [SMILES: *CCN(CC*)CC(=O)O]

Many useful chelating groups, crown ethers, cryptands and the like are known in the art and can be incorporated into the compounds of the invention. See, for example, Pitt et al., "The Design of Chelating Agents for the Treatment of Iron Overload," In, INORGANIC CHEMISTRY IN BIOLOGY AND MEDICINE; Martell, Ed.; American Chemical Society, Washington, D.C., 1980, pp. 279-312; Lindoy, THE CHEMISTRY OF MACROCYCLIC LIGAND COMPLEXES; Cambridge University Press, Cambridge, 1989; Dugas, BIOORGANIC CHEMISTRY; Springer-Verlag, New York, 1989; Chen et al., *J. Photochem. Photobiol.* 135: 27-32 (2000); Parker et al., *Chem. Rev.* 102: 1977-2010 (2002), and references contained therein.

Additionally, a manifold of routes allowing the attachment of chelating agents, crown ethers and cyclodextrins to other molecules is available to those of skill in the art. See, for example, Meares et al., "Properties of In Vivo Chelate-Tagged Proteins and Polypeptides." In, MODIFICATION OF PROTEINS: FOOD, NUTRITIONAL, AND PHARMACOLOGICAL ASPECTS;" Feeney, et al., Eds., American Chemical Society, Washington, D.C., 1982, pp. 370-387; Kasina et al., *Bioconjugate Chem.*, 9: 108-117 (1998); Song et al., *Bioconjugate Chem.*, 8: 249-255 (1997).

In yet another exemplary embodiment, the invention provides a compound according to Formula I, wherein at least one of $R^1$, $R^3$ and $R^5$ has the structure:

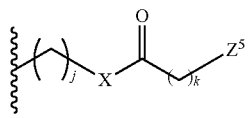

wherein $Z^5$ is a member selected from H, $OR^{17}$, $SR^{17}$, $NHR^{17}$, $OCOR^{18}$, $OC(O)NHR^{18}$, $NHC(O)OR^{17}$, $OS(O)_2OR^{17}$, and $C(O)R^{18}$. The symbol $R^{17}$ represents H, substituted or unsubstituted alkyl, or substituted or unsubstituted heteroalkyl. $R^{18}$ is a member selected from H, $OR^{19}$, $NR^{19}NH_2$, SH, $C(O)R^{19}$, $NR^{19}H$, substituted or unsubstituted alkyl and substituted or unsubstituted heteroalkyl. $R^{19}$ is a member selected from H, substituted or unsubstituted alkyl and substituted or unsubstituted alkyl. The symbol X represents a member selected from O, S and $NR^{20}$, wherein $R^{20}$ is a member selected from H, substituted or unsubstituted alkyl and substituted or unsubstituted heteroalkyl; and the symbols j an k represent members independently selected from the group consisting of integers from 1 to 20. Other linking moieties useful with the compounds of the invention will be apparent to those of skill in the art.

Thus, in another exemplary embodiment, at least one of $R^1$, $R^3$ and $R^5$ is an ether or a polyether, preferably a member selected from ethylene glycol, ethylene glycol oligomers and combinations thereof, having a molecular weight of from about 60 daltons to about 10,000 daltons, and more preferably of from about 100 daltons to about 1,000 daltons.

Representative polyether-based substituents include, but are not limited to, the following structures:

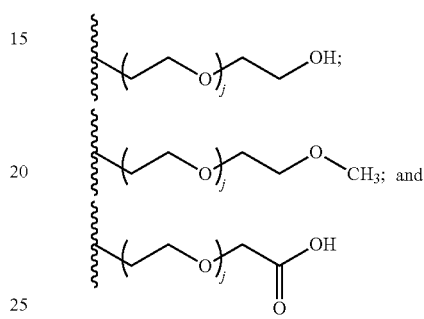

in which j is preferably a number from 1 to 100, inclusive. Other functionalized polyethers are known to those of skill in the art, and many are commercially available from, for example, Shearwater Polymers, Inc. (Alabama).

In another preferred embodiment, the linker includes a reactive group for conjugating said compound to a member selected from the group consisting of molecules and surfaces. Representative useful reactive groups are discussed in greater detail in the succeeding section. Additional information on useful reactive groups is known to those of skill in the art. See, for example, Hermanson, BIOCONJUGATE TECHNIQUES, Academic Press, San Diego, 1996.

In yet another preferred embodiment, the linker attached to one or more of $R^1$, $R^3$ and $R^5$ can combine characteristics of one or more of the above-recited groups. Exemplary "bifunctional" linker groups include, but are not limited to, moieties such as sugars (e.g., polyol with reactive hydroxyl), amino acids, amino alcohols, carboxy alcohols, amino thiols, and the like.

In yet another exemplary embodiment, the invention provides a compound having the structure:

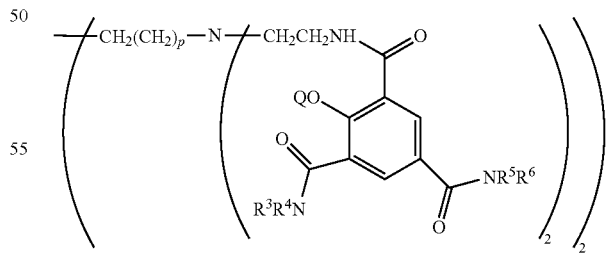

in which p is an integer from 0 to 2. The identities of the various radicals are substantially identical to those discussed for Formula I.

Polymers

In another exemplary embodiment, the invention provides a polymer that includes a subunit according to Formula I. The polymer may be a synthetic polymer (e.g., poly(styrene), poly(acrylamide), poly(lysine), polyethers, polyimines, dendrimers, cyclodextrins, and dextran) or a biopolymer, e.g, polypeptides (e.g., antibody, enzyme, serum protein), saccharide, nucleic acid, antigen, hapten, etc.

In an exemplary embodiment, the polymer has the structure:

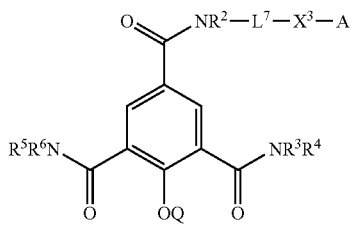

wherein $L^7$ is a member selected from a bond, substituted or unsubstituted alkyl, substituted or unsubstituted heteroalkyl, substituted or unsubstituted heterocycloalkyl and substituted or unsubstituted aryl. $X^3$ is linking member joining $L^7$ to A, and A is a carrier molecule. Presently preferred species for "A," include, but are not limited to biopolymers (peptides, nucleic acids, saccharides, lipids, etc.), poly(amino acids), polyethers, polyimines, polysaccharides, dendrimers, cyclodextrins, pharmaceutical agents.

In an exemplary embodiment, the polymeric backbone is a dendrimer. Thus, the invention provides compounds having a formula:

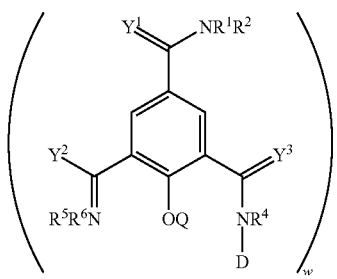

In the formula above, "D" represents the dendrimer; and w is a member selected from integers from 4 to 100, inclusive, and preferably between 8 and 50, inclusive.

The chelating agents of the invention can also form macrocyclic ligands, which are bound to the dendrimer or which incorporate constituents of the dendrimer, e.g., nitrogen or oxygen atoms, into the macrocyclic framework. Such compounds can be generically represented by the formula:

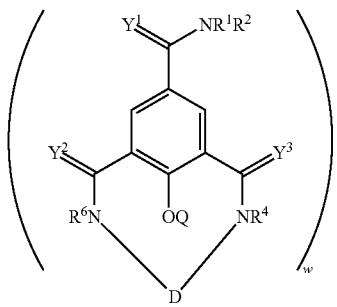

in which D and w are as set forth above. It will be apparent to one of skill that the dendrimer and the ligand in each of these structures can be linked by any type of spacer arm, including, for example an amine, such as the backbone amines of the present invention.

In a preferred embodiment, the dendrimer is a poly(propyleneimine) dendrimer, preferably of generation 2 to generation 10, inclusive.

Cleaveable Groups

The present invention includes compounds that have one or more cleavable group or bond within their structure. Cleaveable groups include bonds that are reversible (e.g., easily hydrolyzed) or partially reversible (e.g., partially or slowly hydrolyzed). Cleavage of the bond generally occurs through biologically- or physiologically-relevant processes under appropriate conditions, e.g., pH, ionic strength, presence of degradative enzyme, etc. In an exemplary embodiment, the cleaveable group is between the dendrimer and the chelating agent. In other embodiments, the cleaveable groups are at other locations within the complex. Other cleavages can also occur, for example, between a spacer and targeting agent and the spacer and the ligand.

In an exemplary embodiment, the ligand of the invention is degraded by enzymes such as non-specific aminopeptidases, esterases, dipeptidyl carboxypeptidases, proteases of the blood clotting cascade, and the like.

Alternatively, cleavage is through a nonenzymatic process. For example, chemical hydrolysis may be initiated by differences in pH experienced by the complex. In such a case, the complex may be characterized by a high degree of chemical lability at physiological pH of 7.4, while exhibiting higher stability at an acidic or basic pH in the delivery vehicle. An exemplary complex, which is cleaved in such a incorporates a N-Mannich base linkage within its framework.

Another exemplary group of cleaveable compounds are those based on non-covalent protein binding groups discussed herein.

The susceptibility of the cleaveable group to degradation can be ascertained through studies of the hydrolytic or enzymatic conversion of the group. Generally, good correlation between in vitro and in vivo activity is found using this method. See, e.g., Phipps et al., *J. Pharm. Sciences* 78:365 (1989). The rates of conversion are readily determined, for example, by spectrophotometric methods or by gas-liquid or high-pressure liquid chromatography. Half-lives and other kinetic parameters may then be calculated using standard techniques. See, e.g., Lowry et al. MECHANISM AND THEORY IN ORGANIC CHEMISTRY, 2nd Ed., Harper & Row, Publishers, New York (1981).

Reactive Functional Groups

As discussed above, certain of the compounds of the invention bear a reactive functional group, such as a component of a linker arm, which can be located at any position on any aryl nucleus or on a chain, such as an alkyl chain, attached to an aryl nucleus, or on the backbone of the chelating agent. These compounds are referred to herein as "reactive ligands." When the reactive group is attached to an alkyl, or substituted alkyl chain tethered to an aryl nucleus, the reactive group is preferably located at a terminal position of the alkyl chain. Reactive groups and classes of reactions useful in practicing the present invention are generally those that are well known in the art of bioconjugate chemistry. Currently favored classes of reactions available with reactive ligands of the invention are those, which proceed under relatively mild conditions. These include, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982.

Useful reactive functional groups include, for example:
(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;
(b) hydroxyl groups, which can be converted to esters, ethers, aldehydes, etc.
(c) haloalkyl groups, wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;
(d) dienophile groups, which are capable of participating in Diels-Alder reactions such as, for example, maleimido groups;
(e) aldehyde or ketone groups, such that subsequent derivatization is possible via formation of carbonyl derivatives such as, for example, imines, hydrazones, semicarbazones or oximes, or via such mechanisms as Grignard addition or alkyllithium addition;
(f) sulfonyl halide groups for subsequent reaction with amines, for example, to form sulfonamides;
(g) thiol groups, which can be converted to disulfides or reacted with acyl halides;
(h) amine or sulfhydryl groups, which can be, for example, acylated, alkylated or oxidized;
(i) alkenes, which can undergo, for example, cycloadditions, acylation, Michael addition, etc;
(j) epoxides, which can react with, for example, amines and hydroxyl compounds; and
(k) phosphoramidites and other standard functional groups useful in nucleic acid synthesis.

The reactive functional groups can be chosen such that they do not participate in, or interfere with, the reactions necessary to assemble the reactive ligand. Alternatively, a reactive functional group can be protected from participating in the reaction by the presence of a protecting group. Those of skill in the art understand how to protect a particular functional group such that it does not interfere with a chosen set of reaction conditions. For examples of useful protecting groups, see, for example, Greene et al., PROTECTIVE GROUPS IN ORGANIC SYNTHESIS, John Wiley & Sons, New York, 1991.

A subset of "reactive functional groups" is "non-covalent protein binding groups," which includes moieties that interact with an intact or denatured polypeptide in an associative manner. The interaction may be either reversible or irreversible in a biological milieu. The incorporation of a "non-covalent protein binding group" into a chelating agent or complex of the invention provides the agent or complex with the ability to interact with a polypeptide in a non-covalent manner. Exemplary non-covalent interactions include hydrophobic-hydrophobic and electrostatic interactions. Exemplary "non-covalent protein binding groups" include anionic groups, e.g., phosphate, thiophosphate, phosphonate, carboxylate, boronate, sulfate, sulfone, thiosulfate, and thiosulfonate. A presently preferred group is sulfonate.

In another exemplary embodiment, the reactive functional group forms a component of a bond, i.e., "linking member" between the linker arm and another species. Thus, the invention provides a compound according to Formula I, wherein a member selected from $R^1$, $R^3$ and $R^5$ has the structure:

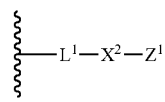

in which $L^1$ is a member selected from substituted or unsubstituted alkyl and substituted or unsubstituted heteroalkyl. The symbol $X^2$ represents a linking member adjoining $L^1$ to $Z^1$; and $Z^1$ is a member selected from carrier molecules and detectable labels.

Targeting Agents

In addition to providing a polymeric "support" or backbone for TIAM and other cheating agents, carrier molecules can be used to target ligands (or complexes) of the invention to a specific region within the body or tissue, or to a selected species or structure in vitro. Selective targeting of an agent by its attachment to a species with an affinity for the targeted region is well known in the art. Both small molecule and polymeric targeting agents are of use in the present invention.

The ligands (or complexes) can be linked to targeting agents that selectively deliver it to a cell, organ or region of the body. Exemplary targeting agents such as antibodies, ligands for receptors, lectins, saccharides, antibodies, and the like are recognized in the art and are useful without limitation in practicing the present invention. Other targeting agents include a class of compounds that do not include specific molecular recognition motifs include macromolecules such as poly(ethylene glycol), polysaccharide, polyamino acids and the like, which add molecular mass to the ligand. The ligand-targeting agent conjugates of the invention are exemplified by the use of a nucleic acid-ligand conjugate. The focus on ligand-oligonucleotide conjugates is for clarity of illustration and is not limiting of the scope of targeting agents to which the ligands (or complexes) of the invention can be conjugated. Moreover, it is understood that "ligand" refers to both the free ligand and its metal complexes.

Exemplary nucleic acid targeting agents include aptamers, antisense compounds, and nucleic acids that form triple helices. Typically, a hydroxyl group of a sugar residue, an amino group from a base residue, or a phosphate oxygen of the nucleotide is utilized as the needed chemical functionality to couple the nucleotide-based targeting agent to the ligand. However, one of skill in the art will readily appreciate that other "non-natural" reactive functionalities can be appended to a nucleic acid by conventional techniques. For example, the hydroxyl group of the sugar residue can be converted to a mercapto or amino group using techniques well known in the art.

The carrier molecules may also be used as a backbone for compounds of the invention that are poly- or multi-valent species, including, for example, species such as dimers, trimers, tetramers and higher homologs of the compounds of the invention or reactive analogues thereof. The poly- and multi-valent species can be assembled from a single species or more than one species of the invention. For example, a dimeric construct can be "homo-dimeric" or "heterodimeric." Moreover, poly- and multi-valent constructs in which a compound of the invention or a reactive analogue thereof, is attached to an oligomeric or polymeric framework (e.g., polylysine, dextran, hydroxyethyl starch and the like) are within the scope of the present invention. The framework is preferably polyfunctional (i.e. having an array of reactive sites for attaching compounds of the invention). Moreover, the framework can be derivatized with a single species of the invention or more than one species of the invention.

Moreover, the properties of the carrier molecule can be selected to afford compounds having water-solubility that is enhanced relative to analogous compounds that are not similarly functionalized. Thus, any of the substituents set forth herein can be replaced with analogous radicals that have enhanced water solubility. For example, it is within the scope of the invention to, for example, replace a hydroxyl group with a diol, or an amine with a quaternary amine, hydroxylamine or similar more water-soluble moiety. In a preferred embodiment, additional water solubility is imparted by substitution at a site not essential for the activity towards the ion channel of the compounds set forth herein with a moiety that enhances the water solubility of the parent compounds. Methods of enhancing the water-solubility of organic compounds are known in the art. Such methods include, but are not limited to, functionalizing an organic nucleus with a permanently charged moiety, e.g., quaternary ammonium, or a group that is charged at a physiologically relevant pH, e.g. carboxylic acid, amine. Other methods include, appending to the organic nucleus hydroxyl- or amine-containing groups, e.g. alcohols, polyols, polyethers, and the like. Representative examples include, but are not limited to, polylysine, polyethyleneimine, poly(ethyleneglycol) and poly(propyleneglycol). Suitable functionalization chemistries and strategies for these compounds are known in the art. See, for example, Dunn, R. L., et al., Eds. POLYMERIC DRUGS AND DRUG DELIVERY SYSTEMS, ACS Symposium Series Vol. 469, American Chemical Society, Washington, D.C. 1991.

Metal Ion Complexes

In another embodiment, the invention provides a luminescent lanthanide ion complex. The chelating group comprises at least one TIAM group, preferably between 2 and 100 TIAM groups, more preferably between 3 and 75 TIAM groups, even more preferably between 4 and 50 TIAM groups and more preferably still, between 5 and 25 TIAM groups. The Tb complex preferably has a quantum yield of at least about 0.1. Even more preferably, the lanthanide ion of the complex is a member selected from europium, terbium and combinations thereof.

Moreover, when the chelating agent includes more than one chelating moiety, the chelating moieties (e.g., TIAM groups) can be interconnected by a backbone of substantially any length and chemical composition, with the proviso that the backbone should orient the chelating moieties and other rings in a manner that is conducive to their complexation of the desired metal ion. That the backbone be stable to the conditions in which the complex is used is also generally preferred. As such, representative backbones include, for example, substituted or unsubstituted alkyl (e.g., conjugated unsaturated systems), substituted or unsubstituted heteroalkyl, substituted or unsubstituted aryl groups, substituted or unsubstituted heteroaryl groups, dendrimers, polyethers, polyamides, polyimines, biopolymers and backbones that are a combination of more than one of these groups. Other useful backbone systems will be apparent to those of skill in the art.

Synthesis

An exemplary synthesis of a compound of the invention, beginning with 3, is shown in Scheme 1. The synthesis of multidentate triamide isophthalamide ligands (abbreviated as TIAMs) begins with 2-hydroxy-benzene-1,3,5-tricarboxylic acid 3. For the purpose of synthesizing water-soluble, octadentate lanthanide chelators, the three carboxyl groups of compound 3 must be differentiated from one another for different amidation reactions. The present method provides a means of differentiating the carboxylic acid positions.

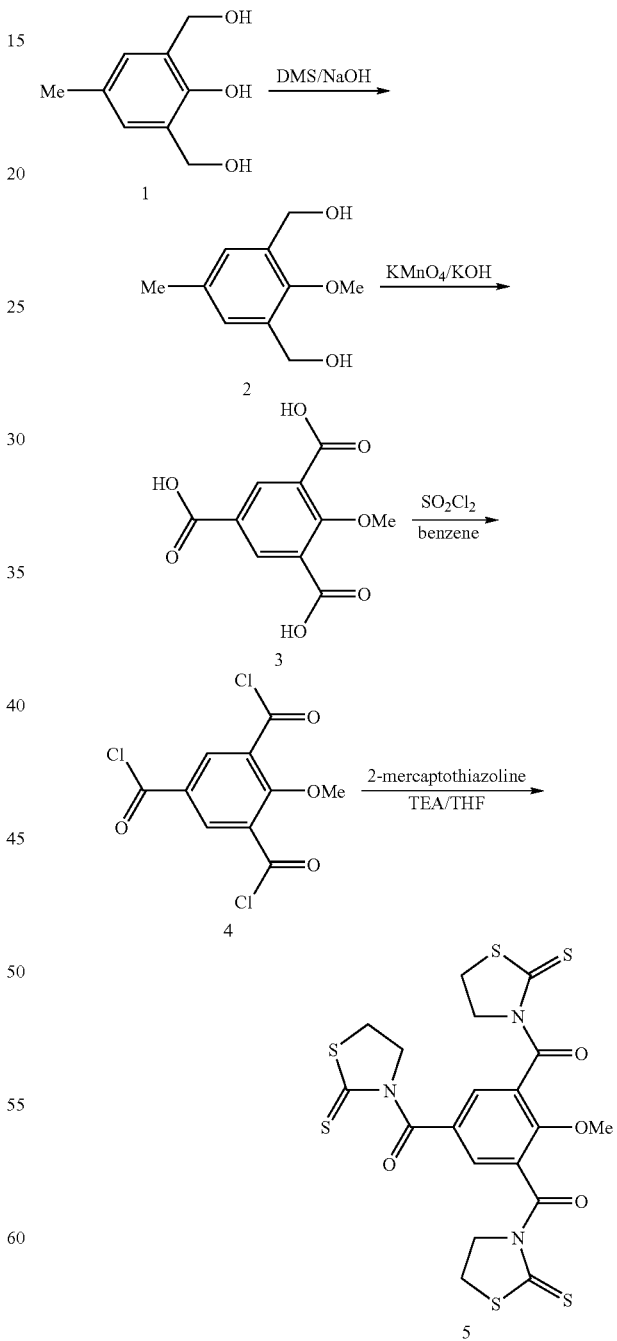

According to Scheme 1, the methyl triol, 1, is selectively O-methylated with DMS/NaOH, providing ether 2. The free hydroxyl moieties are oxidized to carboxylic acids by the action of potassium permanganate, affording mono-protected tri-acid 3. The triacid is converted to the corresponding tri-acid chloride 4. The acid chloride is reacted with 2-mercap-tothiazoline, affording the thiazolide (2-methoxy-3,5-bis-(2-thioxo-thiazolidine-3-carbonyl)-phenyl]-(2-thioxo-thiazolidin-3-yl)-methanone) 5.

The first step of amidation of compound 5 gives the amidation product at the 5-position carboxyl group (compound 6A, 6B, 6C). This step allows the functionalization of the remote 5-position carboxyl group with a linking functional group while not disturbing the coordination sphere of the lanthanide ions. The further amidation reactions occur at the 3-position carboxyl group, to give the mono-thiazolides 7A, 7B, 7C. The monothiazolides are the key processors, they can be coupled with polyamine backbone to form the protected chelators (Scheme 2).

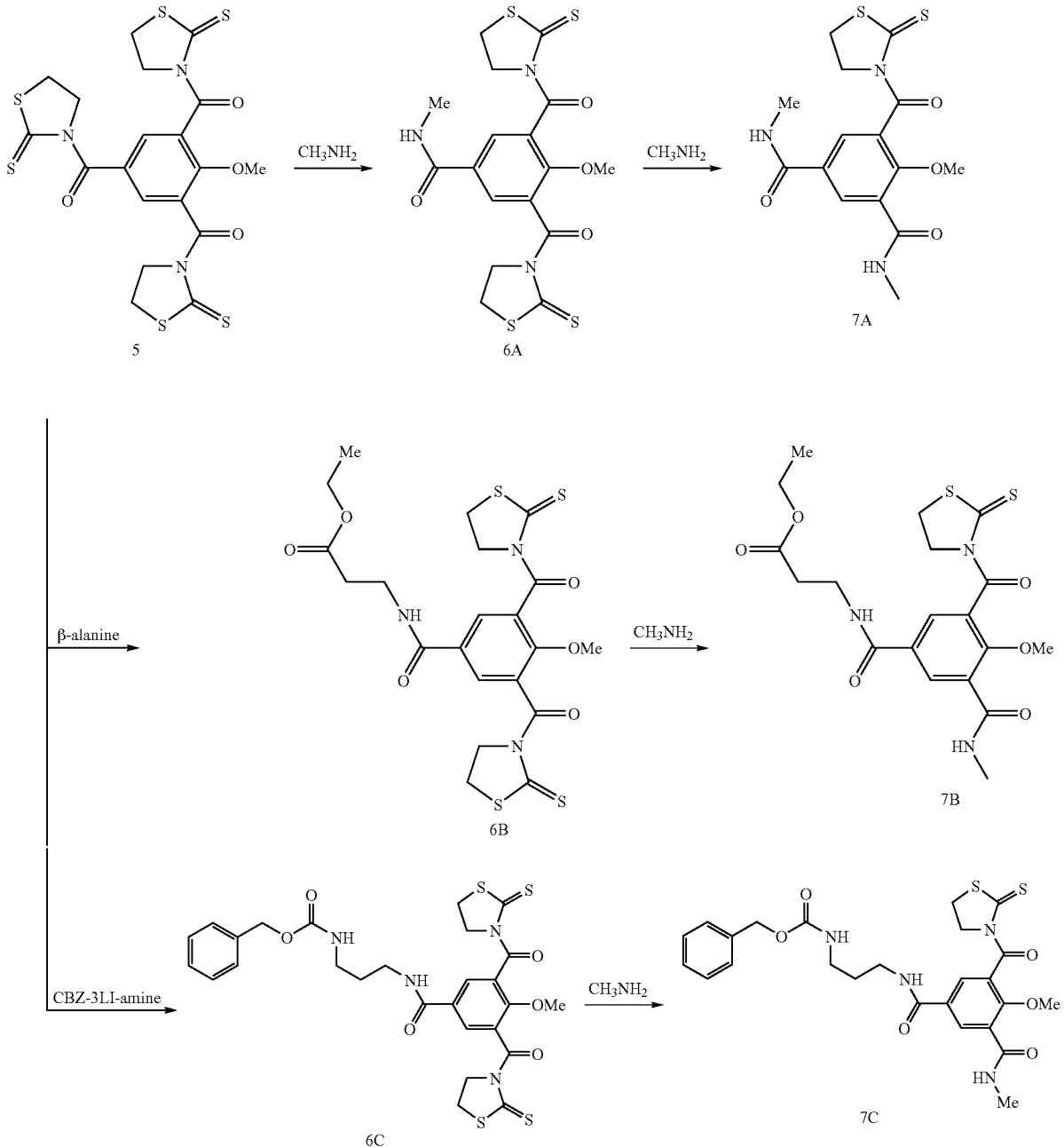

The monothiazolide species (7A, 7B, 7C, etc.) can be combined with various polyamine scaffolds, e.g., a tetra-primary amine such as H(2,2)amine, to form the protected octadentate ligands (8A, 8B, 8C etc.). Deprotection of compounds 8A-8I produces the desired products with four linking groups as shown in Scheme 3:

Scheme 3
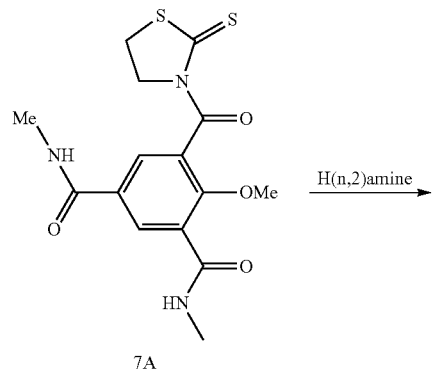
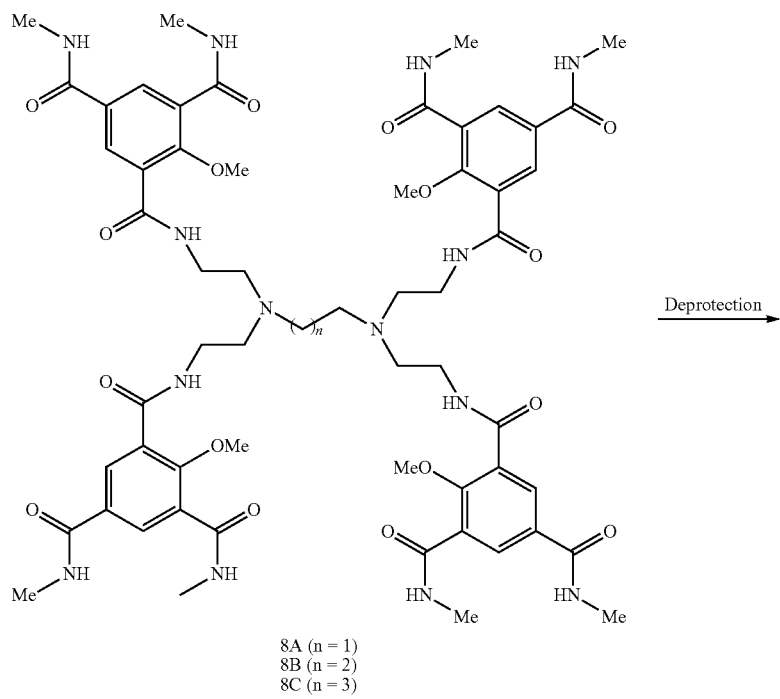
8A (n = 1)
8B (n = 2)
8C (n = 3)

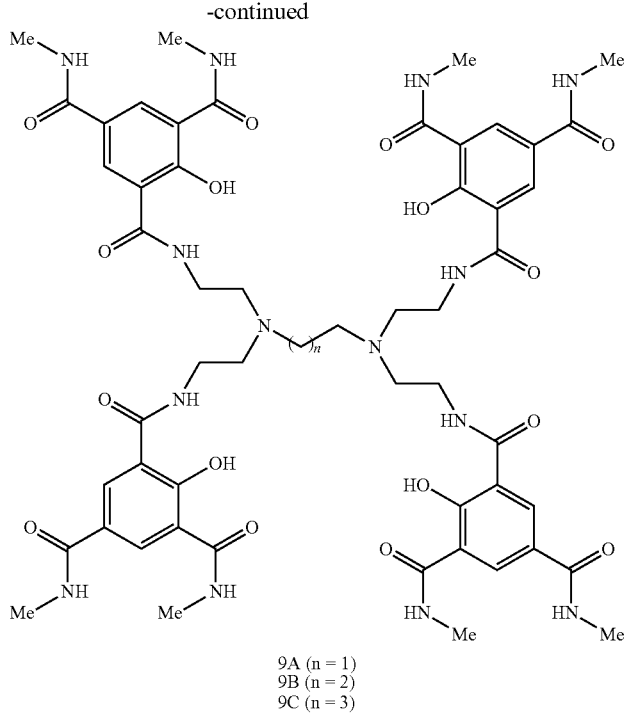
9A (n = 1)
9B (n = 2)
9C (n = 3)
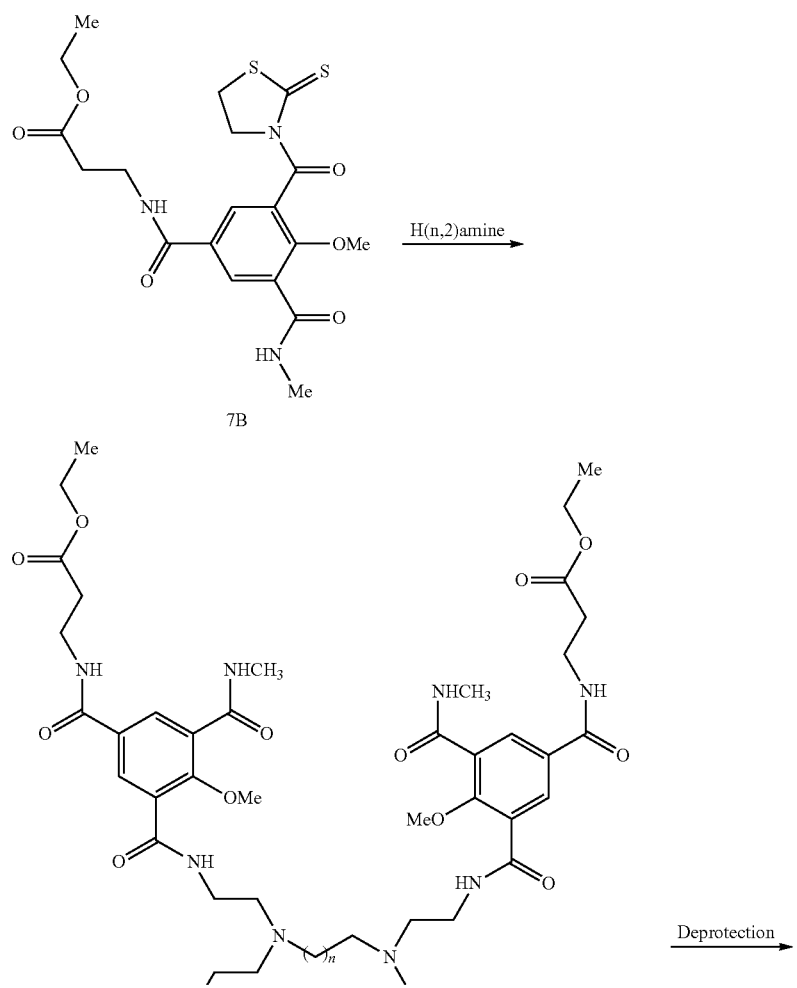

-continued
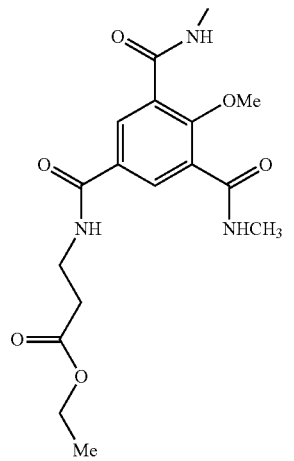
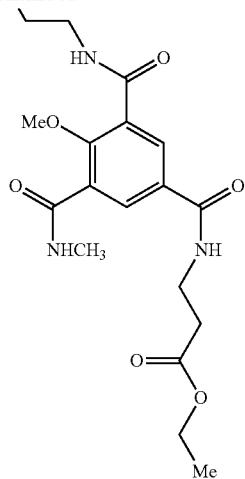
8D (n = 1)
8E (n = 2)
8F (n = 3)
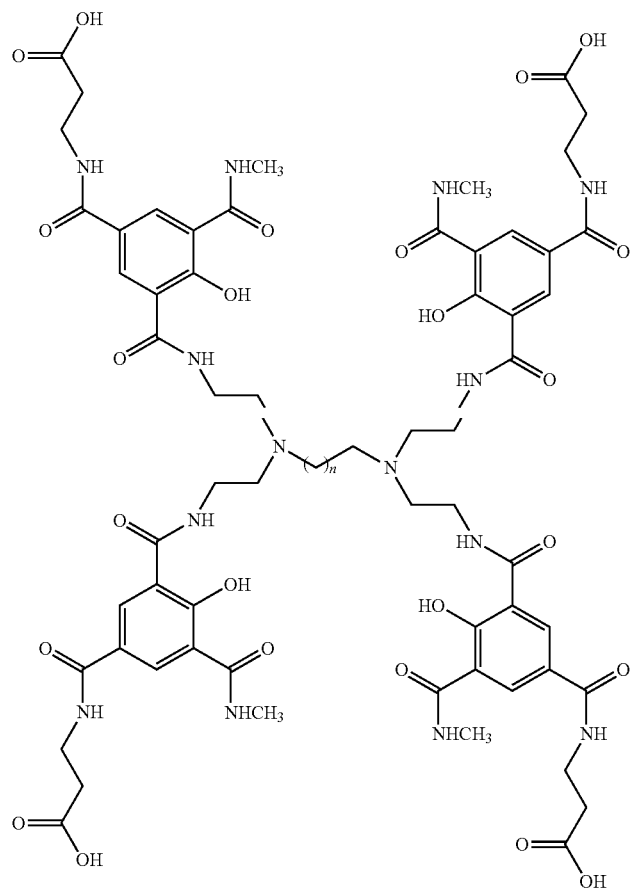
9D (n = 1)
9E (n = 2)
9F (n = 3)

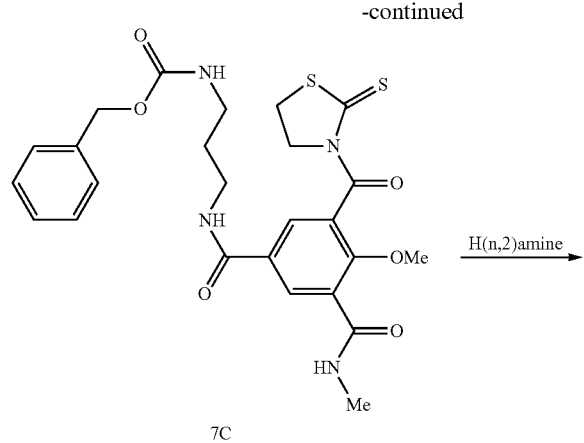
7C
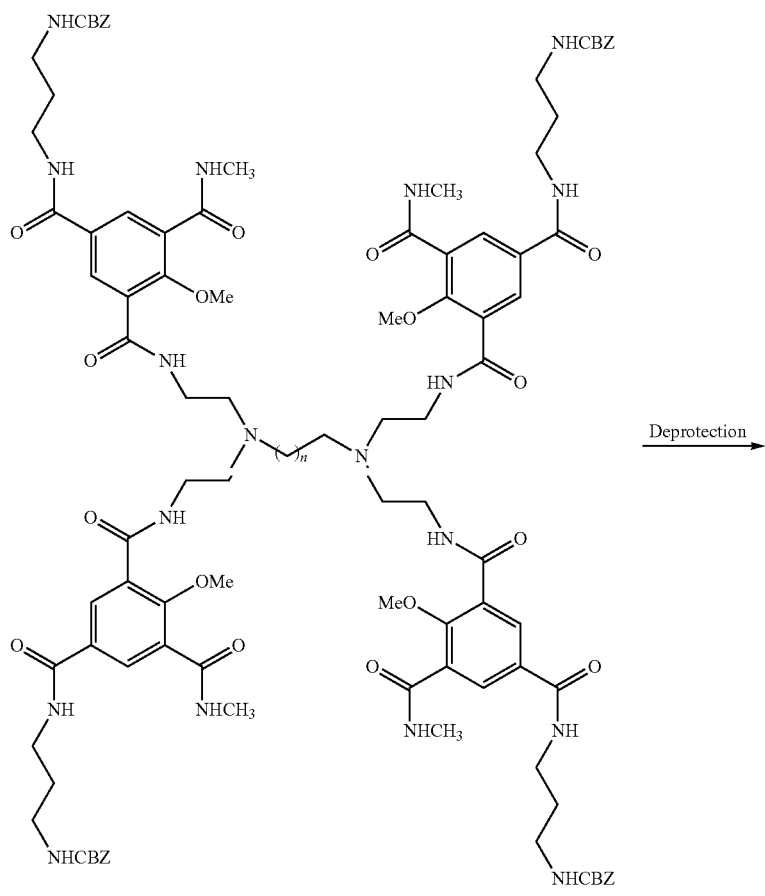
8G (n = 1)
8H (n = 2)
8I (n = 3)

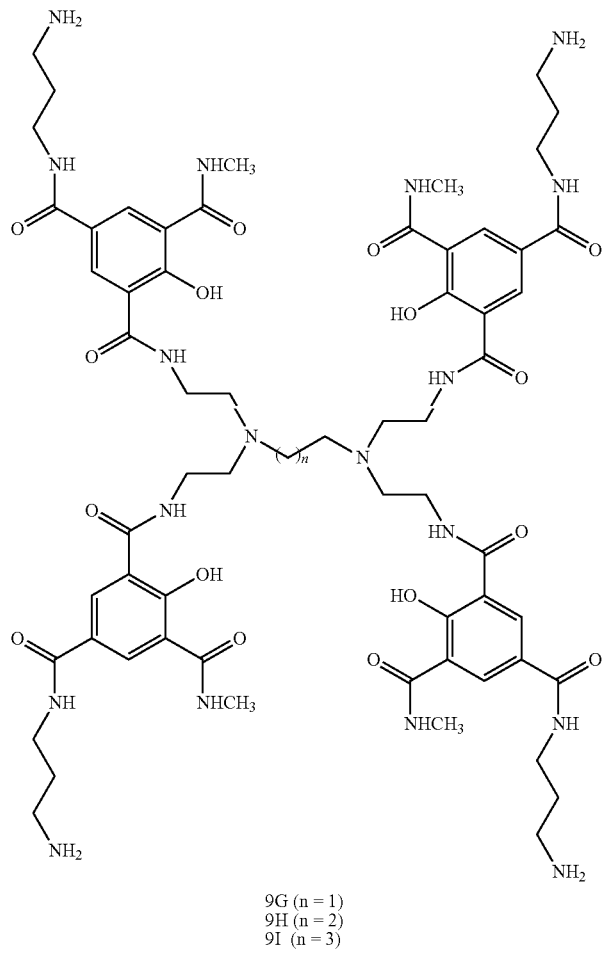

9G (n = 1)
9H (n = 2)
9I (n = 3)

The tetra-functionalized chelators, with four linking functional groups, are easily coupled to molecules, e.g., biomolecules, to be integrated in various applications. In an exemplary embodiment, the invention provides an octadentate chelator having a single linking group, serving as a specific locus of attachment for linking the TIAM to another species.

Thus, the invention also provides ligands having a single linking group. The compounds of the invention with a single linking group are exemplified by the octadentate chelator prepared according to Scheme 4. An exemplary route to the mono-functionalized ligands of the invention involves preparation of a partially functionalized intermediate H(2,2)-amine (or other tetra-amine) precursor, in which only three of the four primary amine moieties were functionalized (10A-10C). The selective functionalization is accomplished by reaction of 7A with a tetra-amine under high dilution conditions (Scheme 4).

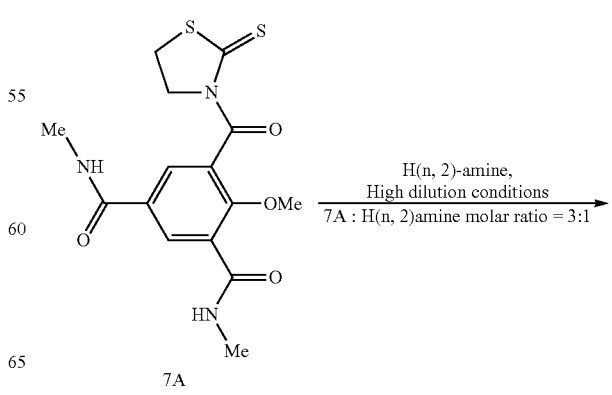

Scheme 4

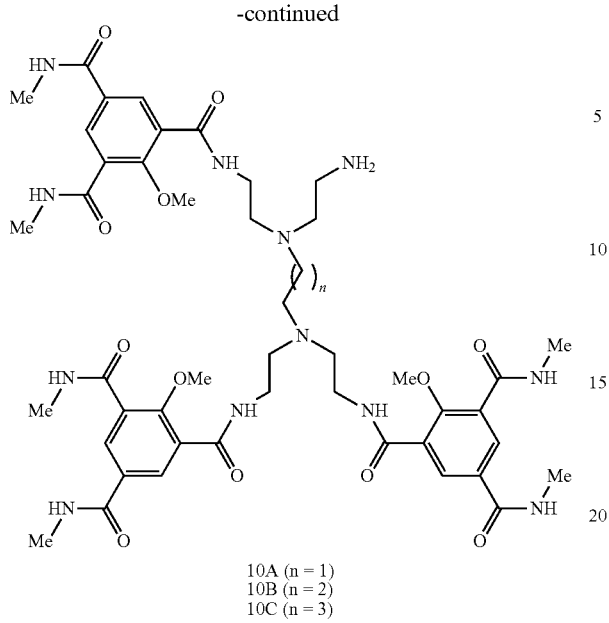
10A (n = 1)
10B (n = 2)
10C (n = 3)
The intermediate 10A, 10B, 10C is combined with a selected monothiazolide (e.g., 7B, 7C or other) to form the desired multidentate precursor. The mono-functionalized octadentate chelator is obtained after deprotection. (Scheme 5)
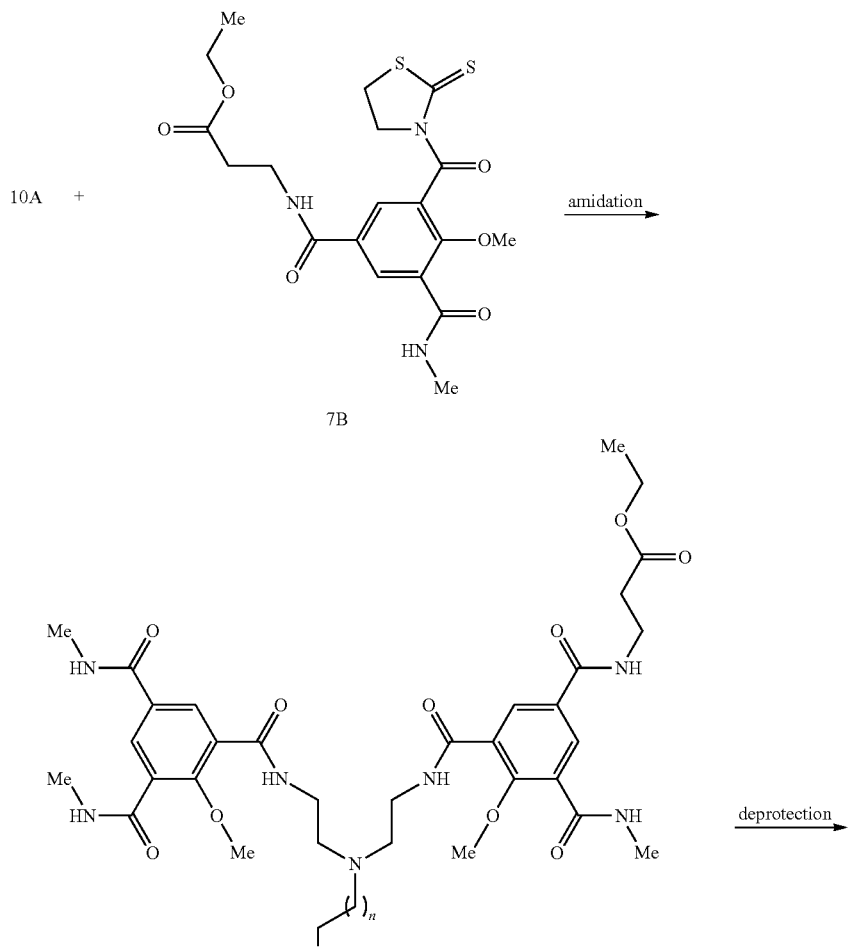
Scheme 5

-continued
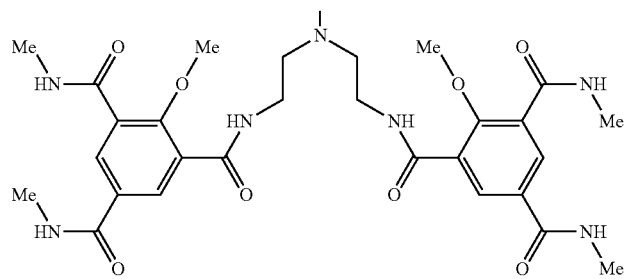
11A (n = 1)
11B (n = 2)
11C (n = 3)
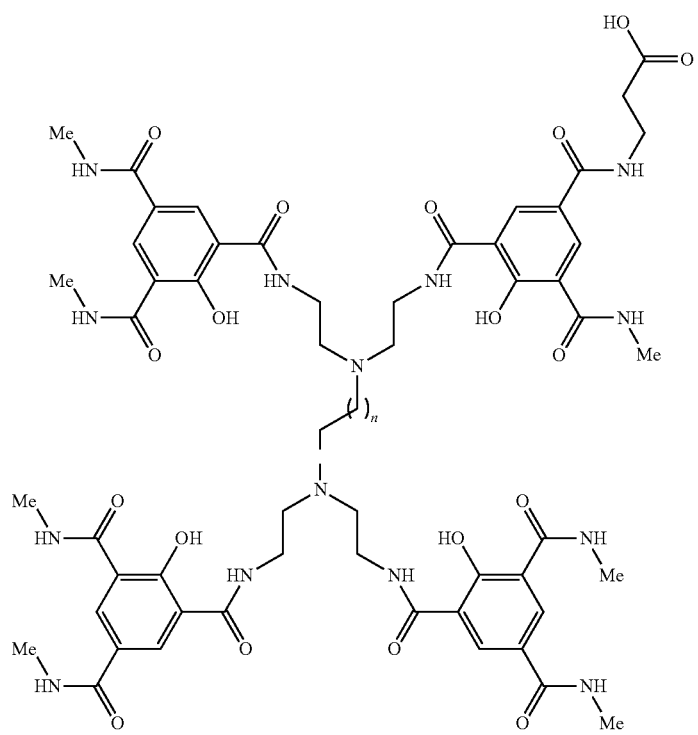
12A (n = 1)
12B (n = 2)
12C (n = 3)
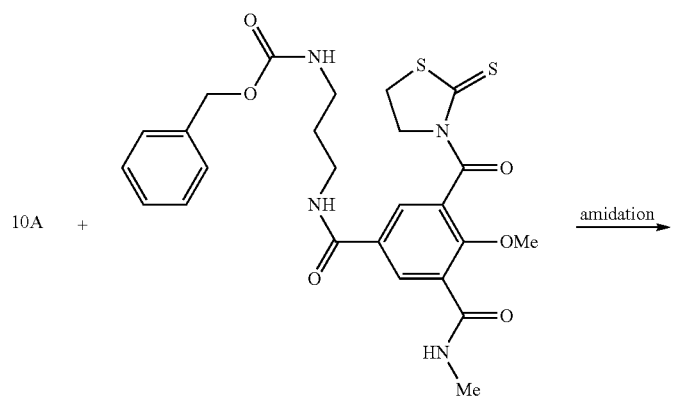
10A +   7C   →  amidation -continued
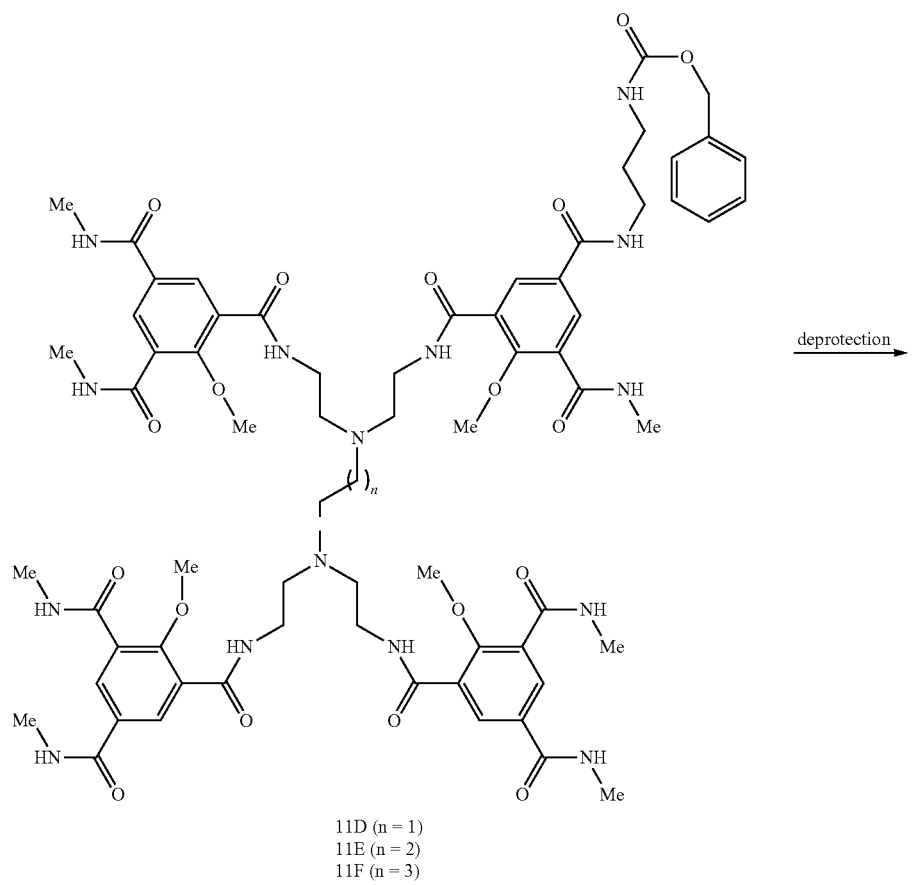
11D (n = 1)
11E (n = 2)
11F (n = 3)
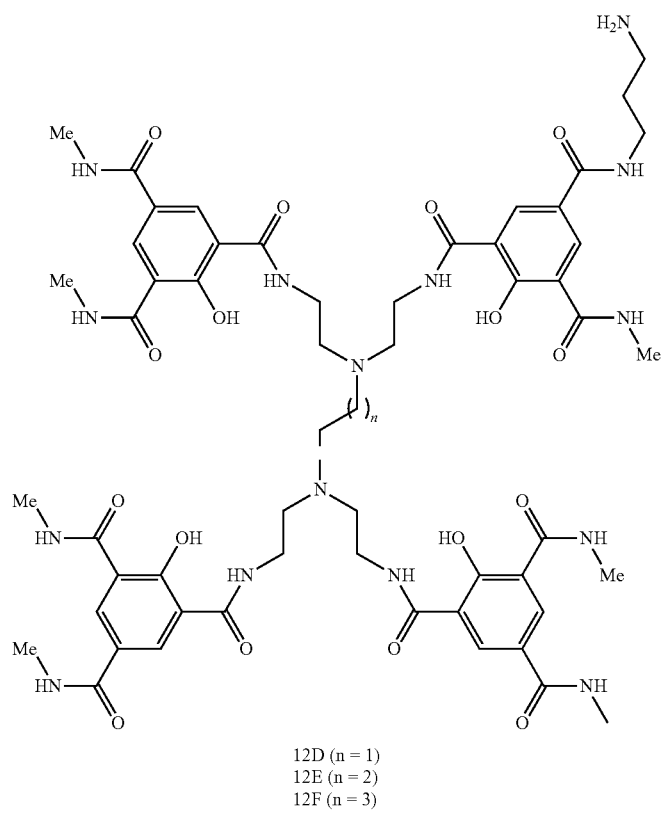
12D (n = 1)
12E (n = 2)
12F (n = 3)

The invention also provides highly water-soluble ligands and their metal ion complexes. An exemplary ligand of the invention includes a poly(ethylene glycol) (PEG) or other ether moiety, which dramatically increases the water solubility of the resulting ligand relative to the precursor without PEG. As shown in Scheme 6, the perbenzylated intermediate 14 is selectively debenzylated by cleaving the benzyl ester groups under hydrolytic conditions, affording 15. The corresponding acid chloride 16 is reacted with 2-mearcaptothiazoline to form the trithiazolide 17.

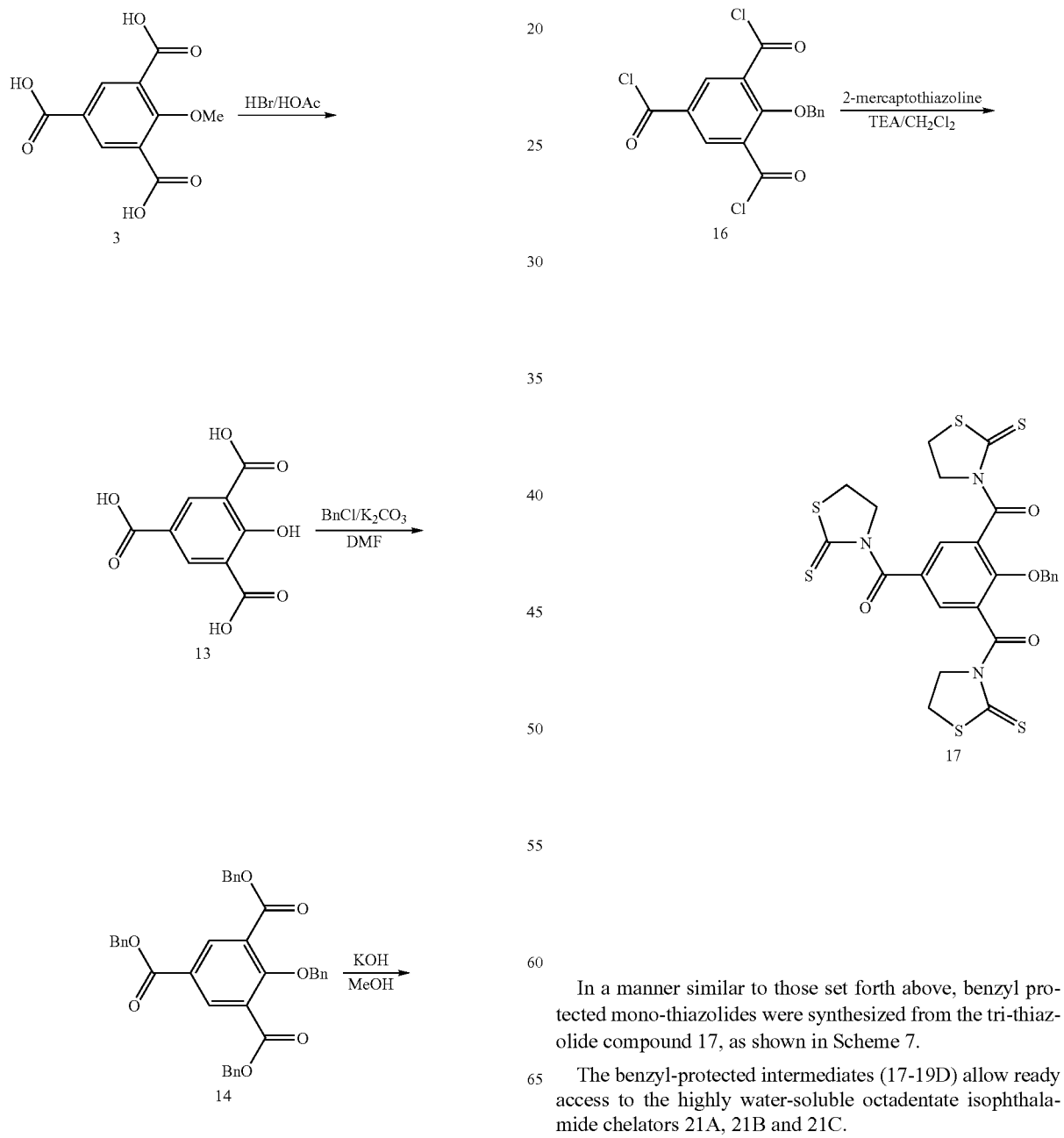

In a manner similar to those set forth above, benzyl protected mono-thiazolides were synthesized from the tri-thiazolide compound 17, as shown in Scheme 7.

The benzyl-protected intermediates (17-19D) allow ready access to the highly water-soluble octadentate isophthalamide chelators 21A, 21B and 21C.

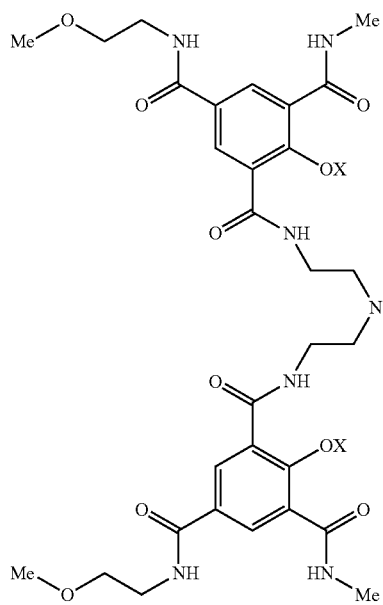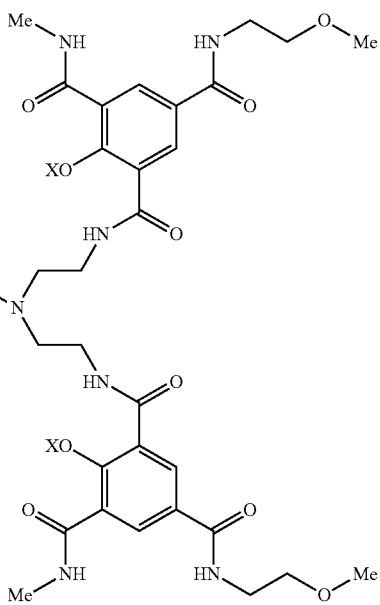
20A (n = 1, X = Bn)  21A (n = 1, X = H)
20B (n = 2, X = Bn)  21B (n = 2, X = H)
20C (n = 3, X = Bn)  21C (n = 3, X = H)
Scheme 7
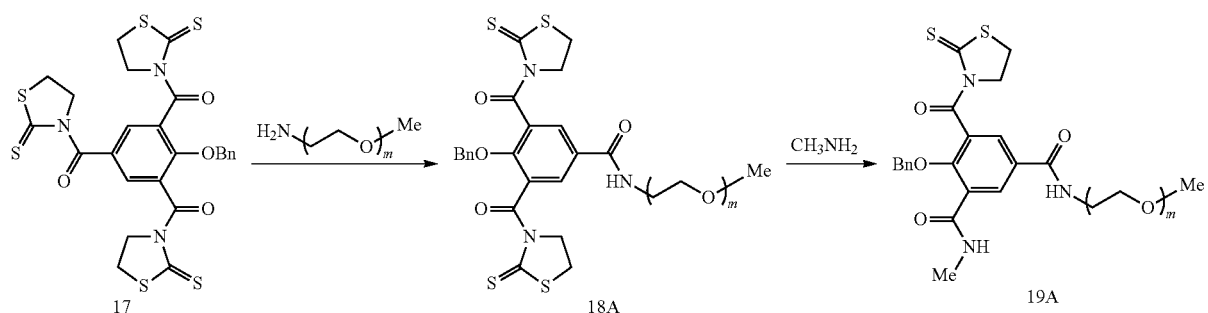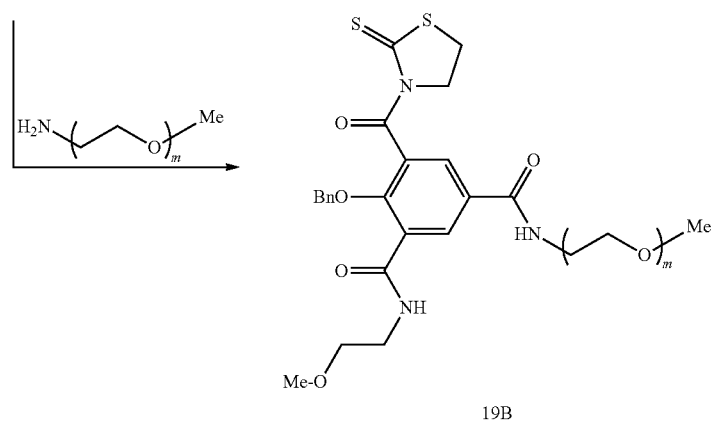

-continued
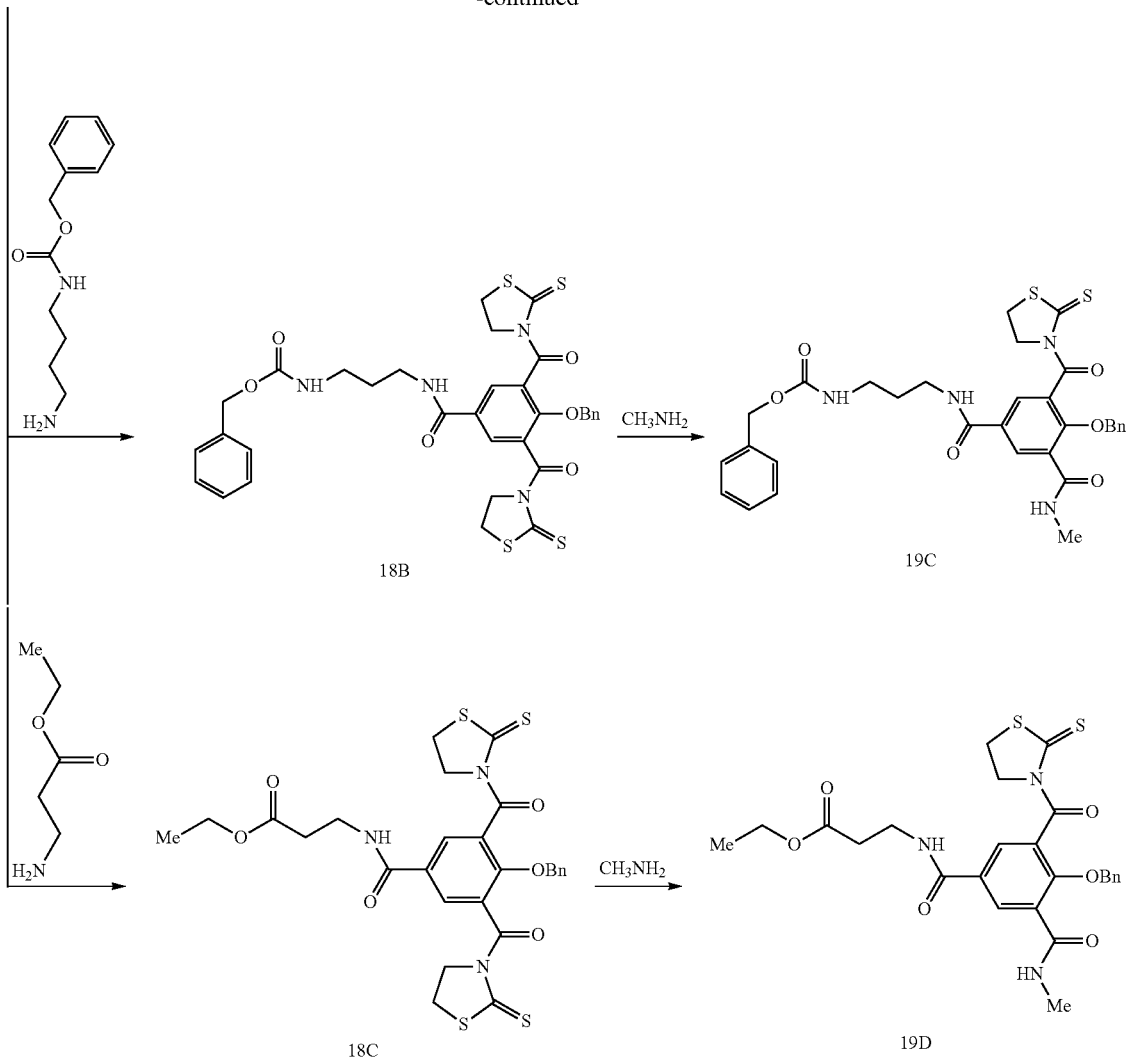
By using a strategy similar to that of the synthesis of 10A, the partially functionalized benzyl-protected H(n,2)-monoamine precursors (21A, 21B) was prepared:
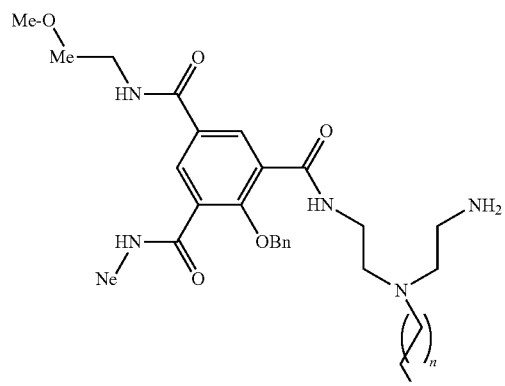

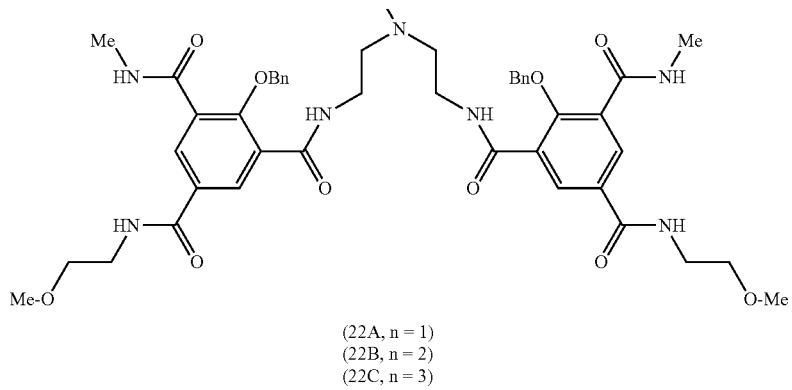
(22A, n = 1)
(22B, n = 2)
(22C, n = 3)
The invention also provides ligands having a water-solubilizing group in addition to a sole linking group. Exemplary compounds accessible by the route set forth above include the highly water soluble chelators (23, 24) bearing only one primary amine or carboxylic acid moiety:
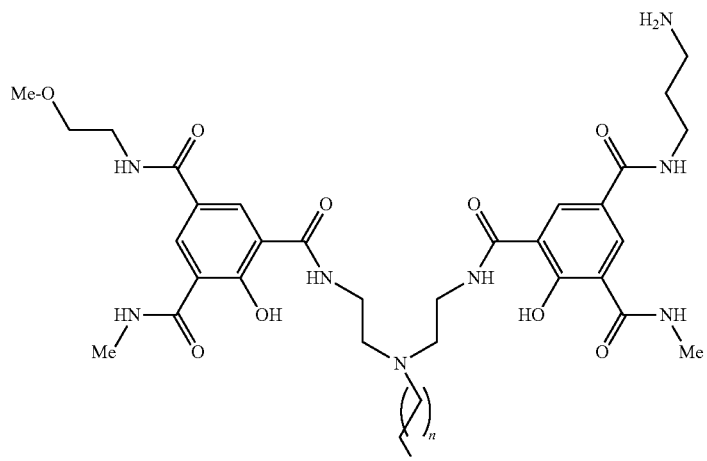
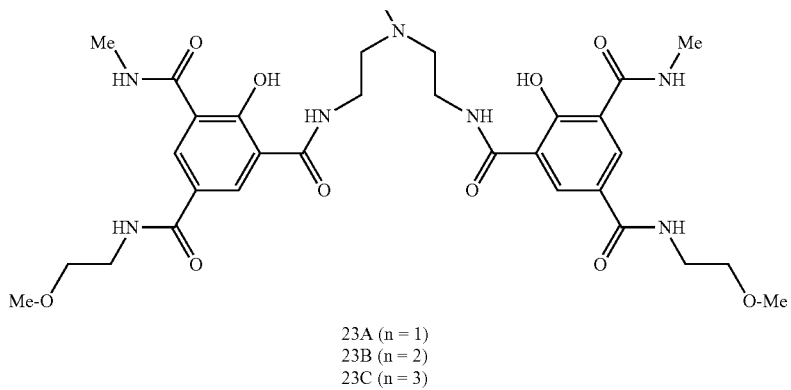
23A (n = 1)
23B (n = 2)
23C (n = 3)

-continued

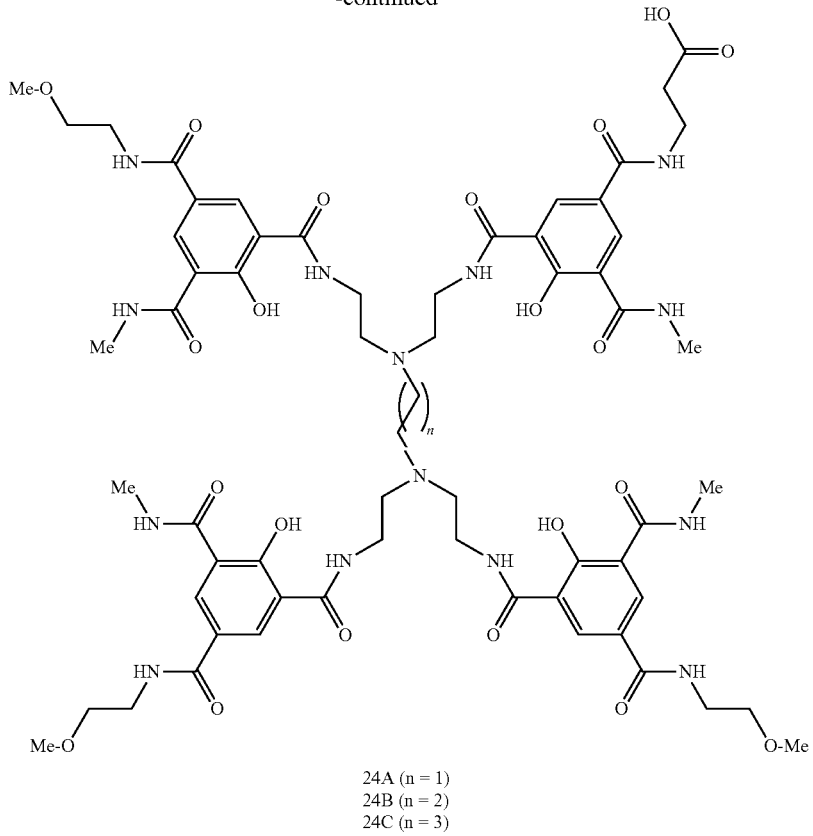

24A (n = 1)
24B (n = 2)
24C (n = 3)

With the synthetic methodology discussed above, macrocyclic compounds that include TIAMs can be prepared. The macrocycles are exemplified by the macrotricycles (described below). The macrocyclic chelators provide coordinated lanthanide ions with encapsulated coordination environment. Moreover, the macrocycles include a locus of attachment, allowing the macrocycles to be tethered to a carrier or other molecule.

After the ligand is formed and purified, the fluorescent lanthanide complex is synthesized by any of a wide range of art-recognized methods, including, for example, by incubating a salt of the chelate with a lanthanide salt such as the lanthanide trihalide, triacetate, and the like.

The compounds of the invention, in their unconjugated form are useful as probes, indicators, separation media, and the like. Moreover, the compounds of the invention can be (25)

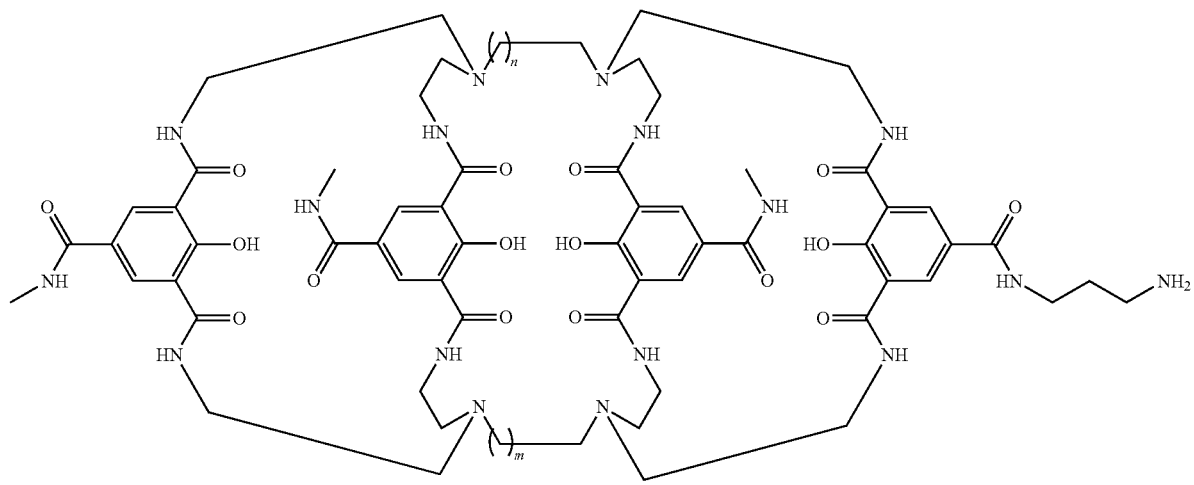

conjugated to a wide variety of compounds to create specific labels, probes, diagnostic and/or therapeutic reagents, etc. Examples of species to which the compounds of the invention can be conjugated include, for example, biomolecules such as proteins (e.g., antibodies, enzymes, receptors, etc.), nucleic acids (e.g., RNA, DNA, etc.), bioactive molecules (e.g., drugs, toxins, etc.); solid substrates such as glass or polymeric beads, sheets, fibers, membranes (e.g. nylon, nitrocellulose), slides (e.g. glass, quartz) and probes; etc.

Assays and TIAM-Bearing Probes

In another preferred embodiment, the present invention provides a chelating agent or complex that is tethered to another molecule, such as a probe molecule and assays using these probes.

Assays

The following discussion is generally relevant to the assays described herein. This discussion is intended to illustrate the invention by reference to certain preferred embodiments and should not be interpreted as limiting the scope of probes and assay types in which the compounds of the invention find use. Other assay formats utilizing the compounds of the invention will be apparent to those of skill in the art.

Assays based on specific binding reactions are used for detecting a wide variety of substances such as drugs, hormones, enzymes, proteins, antibodies, and infectious agents in various biological fluids and tissue samples. In general, the assays consist of an analyte, a recognition moiety for the analyte, and a detectable label. Competitive assay modalities generally utilize a binding partner in addition to these components. In an exemplary embodiment, the binding partner is a molecule that interacts with a recognition moiety to form a complex that is inherently less stable than a similar complex formed between the recognition moiety and the analyte, and is subsequently displaced by the incoming analyte.

Because the results of specific binding interactions are frequently not directly observable, a variety of fluorescent labels have been devised for determining the presence of an interaction. The fluorophores of the invention are detected by use of fluorescence spectroscopy or by the naked eye. An introduction to labels, labeling procedures and detection of labels, such as are useful in practicing the present invention, is found in Polak et al., INTRODUCTION TO IMMUNOCYTOCHEMISTRY, 2$^{nd}$ Ed., Springer Verlag, NY, (1977), and in Haugland, HANDBOOK OF FLUORESCENT PROBES AND RESEARCH CHEMICALS, a combined handbook and catalogue Published by Molecular Probes, Inc., Eugene, Oreg. (1996)

In certain embodiments, the assay is a competitive assay. In practice, the components of the assay (i.e., recognition moiety, binding partner and analyte) can have substantially any chemical structure, however in a preferred embodiment, the recognition moiety, the binding partner and the analyte are members independently selected from the group consisting of small molecular bioactive agents, biomolecules and combinations thereof. When a component of the assay is a biomolecule, the biomolecule is preferably a member selected from the group consisting of haptens, antibodies, antigens, carbohydrates, nucleic acids, peptides, enzymes and receptors.

In a competitive assay format, one or more than one of the components is labeled with a compound of the invention. For example, in one embodiment, the binding partner is labeled with a compound of the invention and its displacement from an immobilized recognition moiety is detected by the appearance of fluorescence in a liquid phase of the assay. In another competitive assay format, an immobilized enzyme is complexed with a substrate conjugated to a compound of the invention. The complex is then contacted with a putative antagonist. The displacement of fluorescence from the immobilized enzyme into a liquid phase of the assay is indicative of displacement of the substrate by the putative antagonist. These embodiments are offered by way of example only and it will be plain to one of skill in the art that many other competitive assay formats can utilize and benefit from the compounds of the invention.

In addition to ascertaining a binding event, it is frequently desired to quantitate the magnitude of the affinity between two or more binding partners. Thus, it is also within the scope of the present invention to utilize the compounds disclosed herein as a support for such assays.

Most typically, the amount of analyte present is measured by quantitating the amount of label fixed to a binding partner, analyte or recognition moiety following a binding event. Means of detecting and quantitating fluorescent labels are well known to those of skill in the art.

In another preferred embodiment, the affinity between two or more assay constituents is measured by quantifying a population selected from the group consisting of the analyte-recognition moiety complex, free analyte, free binding partner, binding partner-recognition moiety complex and combinations thereof.

The format of an assay for extracting affinity data for two molecules can be understood by reference to an embodiment in which a ligand that is known to bind to a receptor is displaced by an antagonist to that receptor. Other variations on this format will be apparent to those of skill in the art. The competitive format is well known to those of skill in the art. See, for example, U.S. Pat. Nos. 3,654,090 and 3,850,752.

The binding of an antagonist to a receptor can be assayed by a competitive binding method using a ligand for that receptor and the antagonist. The binding assay can be performed, for example, in a 96-well filtration plate assembly (Millipore Corporation, Bedford, Mass.). One of the three binding partners (i.e., the ligand, antagonist or receptor) is generally bound to the well or to a particulate material contained within the well.

Competition binding data can be analyzed by a number of techniques, including nonlinear least-squares curve fitting procedure. When the ligand is an antagonist for the receptor, this method provides the IC50 of the antagonist (concentration of the antagonist which inhibits specific binding of the ligand by 50% at equilibrium). The IC50 is related to the equilibrium dissociation constant (Ki) of the antagonist based on the Cheng and Prusoff equation: $Ki=IC50/(1+L/Kd)$, where L is the concentration of the ligand used in the competitive binding assay, and Kd is the dissociation constant of the ligand as determined by Scatchard analysis. These assays are described, among other places, in Maddox et al., *J Exp Med.*, 158: 1211 (1983); Hampton et al., SEROLOGICAL METHODS, A LABORATORY MANUAL, APS Press, St. Paul, Minn., 1990.

The assays of the invention can be practiced with some or all components in solution. Alternatively, one or more components can be substantially insoluble in the assay medium. In a preferred embodiment, one or more members selected from the group consisting of the recognition moiety, the binding partner and the analyte are attached to a surface. Useful surface include, but are not limited to, glass or polymeric beads, sheets, fibers, membranes (e.g. nylon, nitrocellulose), slides (e.g. glass, quartz) and the like.

The assay can be performed in a large variety of ways. It is within the abilities of one of skill in the art to choose, for example, when to form the fluorescent complex by chelating the lanthanide, which assay component the chelate should be attached to and the like. In a preferred embodiment, the fluorescent complex is formed prior to displacing the binding partner from the binding partner-recognition moiety complex. In another preferred embodiment, the fluorescent complex is formed after displacing the binding partner from the binding partner-recognition moiety complex.

Following the displacement of the binding partner from the binding partner-recognition moiety complex, the remaining steps of the assay can be performed on the mixture that is formed by the displacement or one or more of the components of the mixture can be removed. In a preferred embodiment, the method further comprises separating the free binding partner from a member of the group consisting of the recognition-binding partner pair, the analyte-recognition moiety pair and combinations thereof.

In a preferred embodiment, the assays of the invention are immunological assays. Immunological assays involve reactions between immunoglobulins (antibodies), which are capable of binding with specific antigenic determinants of various compounds and materials (antigens). Other types of reactions include binding between avidin and biotin, protein A and immunoglobulins, lectins and sugar moieties and the like. See, for example, U.S. Pat. No. 4,313,734, issued to Leuvering; U.S. Pat. No. 4,435,504, issued to Zuk; U.S. Pat. Nos. 4,452,901 and 4,960,691, issued to Gordon; and U.S. Pat. No. 3,893,808, issued to Campbell.

These assay techniques provide the ability to detect both the presence and amount of small quantities of analytes and are useful in, for example medical diagnostics and forensic applications. In the methods of the present invention, the analyte or its binding to the recognition moiety is generally detected by the use of a fluorescent label according to the invention.

Immunological assays are of three general types. In an exemplary competitive binding assay, labeled reagents and unlabeled analyte compounds compete for binding sites on a binding material. After an incubation period, unbound materials are washed off and the amount of labeled reagent bound to the site is compared to reference amounts for determination of the analyte concentration in the sample solution.

A second type of immunological assay is known as a sandwich assay and generally involves contacting an analyte sample solution to a surface comprising a first binding material immunologically specific for that analyte. A second solution comprising a binding material bearing a compound of the invention of the same type (antigen or antibody) as the first binding material is then added to the assay. The labeled binding material will bind to any analyte that is bound to the first binding material. The assay system is then subjected to a wash step to remove labeled binding material that failed to bind with the analyte and the amount of labeled material remaining is ordinarily proportional to the amount of bound analyte.

A third type of immunological assay technique involves agglutination reaction techniques and is exemplified by well-known assays for blood antigens and serum types. Immunological cross-reactivity between antibodies within serum and antigens presented on red blood cell surfaces is indicated by the formation of a three dimensional cross-linked network of red blood cells and antibodies. The agglutination of the serum/red blood cell mixture results in the formation of a pellet which can be visible to the naked eye, via the fluorescence of a compound of the invention attached to one or more components of the assay.

These assay procedures, enumerated above, were originally performed according to liquid phase immunochemistry techniques wherein enzymes and radiolabeled reactions were carried out in liquid solution in apparatus such as microtiter plates. More recently, techniques and procedures have been adapted for carrying out "solid" phase assays wherein enzymatic and immunological reactions are carried out in solution on immobilizing substrates.

These types of assays, generally designated immunochromatographic immunoassays, can be developed in any number of formats employing principals of competitive, sandwich, or agglutination types of assays. They can also involve either flow across or flow along the immobilizing substrate. In general, the sandwich assays have the greatest utility for detection of large protein analytes or antibodies. The flow-across type of assays have been used most extensively in sandwich type assays.

In a typical noncompetitive immunochromatographic assay, a test sample of a biological fluid such as blood, serum, plasma, saliva, urine, etc. must be in a sufficient volume and have a sufficient concentration of analyte to allow for sufficient interaction to occur between the analyte of interest, the labeled particles and the capturing solid phase. In order to increase the reaction kinetics, the concentration of particle labeled member of a binding pair and the concentration of binding pair at the surface of the porous membrane or capturing particles is optimized to produce as much specific binding as possible and at the same time minimize any non-specific binding. The concentration of the particle labeled member must be of a concentration that does not produce prozone phenomena throughout the range of analyte concentrations that are of interest. Such concentration optimization is well within the abilities of one of skill.

Immunochromatographic assays can be in the form of strips or layers of the multilayered materials of the invention employing a hydrophobic support (e.g., Mylar, polystyrene, polypropylene, glass, etc.) wherein one or more compounds of the invention or moieties functionalized with a compound of the invention is either fixed directly or indirectly with a binder such as glue to the support. If it is desired, hydrophobic supports and housings can be employed to reduce evaporation of the fluid phase while the immunoreactants are being brought into contact with each other.

In an exemplary non-competitive assay in accordance with this aspect of the invention, an analyte is solubilized, deposited and bound onto the particulate material. The particulate material is then hydrated and sequentially exposed to primary antibodies and enzyme-conjugated secondary antibodies specific for the primary antibodies, with washing steps in between where appropriate. Enzyme levels are then determined by, for instance, substrate conversion protocols well known in the art, and the amount of primary antibodies can thus be measured by reference to a standard run in parallel.

Additionally, a binding domain of a receptor, for example, can serve as the focal point for a drug discovery assay, where, for example, the receptor is immobilized, and incubated both with agents (i.e., ligands) known to interact with the binding domain thereof, and a quantity of a particular drug or inhibitory agent under test. One of the incubation components is labeled with a compound of the invention. The extent to which the drug binds with the receptor and thereby inhibits receptor-ligand complex formation can then be measured. Such possibilities for drug discovery assays are contemplated herein and are considered within the scope of the present invention. Other focal points and appropriate assay formats will be apparent to those of skill in the art.

The compounds and methods of the invention can also be used to sequence nucleic acids and peptides. Fluorescent-labeled oligonucleotide primers have been used in place of radiolabeled primers for sensitive detection of DNA fragments (U.S. Pat. No. 4,855,225 to Smith et al.). Additionally, DNA sequencing products can be labeled with fluorescent dideoxynucleotides (U.S. Pat. No. 5,047,519 to Prober et al.) or by the direct incorporation of a fluorescent labeled deoxynucleotide (Voss et al. *Nucl. Acids Res.* 17:2517 (1989)). The compounds of the invention are useful in both of these formats. As currently practiced, fluorescent sequencing reactions circumvent many of the problems associated with the use of radionuclides.

As discussed above, the fluorescent complex can be formed at substantially any step of the assay. This is equally true in those embodiments, wherein one or more components of the assay mixture are removed following the displacement of the binding partner. In a preferred embodiment, the fluorescent complex is formed following the separation.

Compounds of the invention can be used to indicate the presence and amount of an enzyme in a mixture. For example, in certain embodiments, Q is an enzymatically labile group and the presence of the labile group on the phenolic oxygen of the TIAM group will prevent the formation of a stable complex of a lanthanide ion. This situation is reversed, and a stable lanthanide complex is formed, when the TIAM chelate is contacted with an enzyme that is capable of cleaving the labile group, thus, freeing the phenolic oxygen anion. Similar to the embodiments discussed above, the assay mixture can be contacted with the enzyme at any time during the assay process. Additionally, if a component is separated from the reaction mixture (e.g., the liberated binding partner), the separated component and/or the remaining component can be contacted with the enzyme.

In a preferred embodiment, wherein "Q" is an enzymatically labile group, the method further includes contacting a member selected from the group consisting of the binding partner-recognition moiety complex, the free binding partner and combinations thereof with an enzyme, thereby removing the enzymatically labile group.

An array of enzymatically removable groups is known in the art and it is within the abilities of one of skill in the art to select an appropriate enzymatically labile group for a particular application. In a preferred embodiment, the enzymatically labile group comprises a component of a member selected from the group consisting of phosphate, sulfate, acyl and glycoside groups. Enzymes capable of removing these groups include, for example, esterases, phosphatases, glycosidases and the like.

In another preferred embodiment, the removal of the enzymatically labile group and the subsequent formation of a fluorescent complex is used to detect the presence of an enzyme capable of removing the enzymatically labile group. See, for example, Drevin et al., U.S. Pat. No. 5,252,462, issued Oct. 12, 1993.

Although the compounds of the invention can be tethered to any component of the assay, they will most generally be attached to the binding partner. In this embodiment, the compounds of the invention can be attached to the binding partner through a reactive group on a TIAM moiety, backbone or amide substitutent. Alternatively, they can be attached to the binding partner through a reactive group on the aromatic nucleus of one or more of the TIAM, moieties of the compounds. As discussed above, many suitable reactive groups are known to those of skill in the art and one of skill will be able to both choose and prepare a TIAM-chelate that is appropriately functionalized for a particular application.

It will generally be preferred that the linkage between the TIAM-chelates and the binding partner be stable under the conditions of the assay. Many stable linkages can be formed between the binding partner and the TIAM chelate including, for example, amides, amines, ethers, ureas, and the like. In a preferred embodiment, the linkage between the binding partner and a compound of the invention is a member selected from the group consisting of amide, thioamide, thoiurea and carbamate linkages. Suitable reactive groups and linkages are discussed in greater detail above.

In general, to determine the concentration of a target molecule, such as, for example, a nucleic acid, it is preferable to first obtain reference data in which constant amounts of probe and nucleic acid ligand are contacted with varying amounts of target. The fluorescence emission of each of the reference mixtures is used to derive a graph or table in which target concentration is compared to fluorescence emission. For example, a probe that: a) hybridizes to a target-free nucleic acid ligand; and b) has a stem-loop architecture with the 5' and 3' termini being the sites of fluorescent group labeling, could be used to obtain such reference data. Such a probe gives a characteristic emission profile in which the fluorescence emission decreases as the target concentration increases in the presence of a constant amount of probe and nucleic acid ligand. Then, a test mixture with an unknown amount of target is contacted with the same amount of first nucleic acid ligand and second probe, and the fluorescence emission is determined. The value of the fluorescence emission is then compared with the reference data to obtain the concentration of the target in the test mixture.

Multiplex Analyses

In another preferred embodiment, the quenchers of the invention are utilized as a component of one or more probes used in an assay designed to detect multiple species in a mixture. An assay used to detect two or more species by using at least two probes bearing different fluorophores is referred to herein as a "multiplex analysis."

Probes that include the compounds of the invention are also useful in performing multiplex-type analyses and assays. In a typical multiplex analysis, two or more distinct species (or regions of one or more species) are detected using two or more probes, wherein each of the probes is labeled with a different fluorophore. Preferred multiplex analyses relying on fluorescent energy transfer ideally meet several criteria. The fluorescent species should be bright and spectrally well resolved and the energy transfer between the fluorescent species and the acceptor should be efficient.

Because of the ready availability of complexes of the invention that have different emission characteristics, the compounds of the invention are particularly well suited for use in multiplex applications. Access to complexes having a range of absorbance characteristics allows for the design of FET probes in which the acceptor absorbance properties and the TIAM emission properties are matched, thereby providing a useful level of spectral overlap.

The simultaneous use of two or more probes using FET is known in the art. For example, multiplex assays using nucleic acid probes with different sequence specificities have been described. Fluorescent probes have been used to determine whether an individual is homozygous wild-type, homozygous mutant or heterozygous for a particular mutation. For example, using one quenched-fluorescein molecular beacon that recognizes the wild-type sequence and another rhodamine-quenched molecular beacon that recognizes a mutant allele, it is possible to genotype individuals for the O-chemokine receptor (Kostrikis et al. *Science* 279:1228-1229 (1998)). The presence of only a fluorescein signal indicates that the individual is wild-type, and the presence of rhodamine signal only indicates that the individual is a homozygous mutant. The presence of both rhodamine and fluorescein signal is diagnostic of a heterozygote. Tyagi et al. *Nature Biotechnology* 16: 49-53 (1998)) have described the simultaneous use of four differently labeled molecular beacons for allele discrimination, and Lee et al., *BioTechniques* 27: 342-349 (1999) have described seven color homogenous detection of six PCR products.

The TIAMs of the present invention can be used in multiplex assays designed to detect and/or quantify substantially any species, including, for example, whole cells, viruses, proteins (e.g., enzymes, antibodies, receptors), glycoproteins, lipoproteins, subcellular particles, organisms (e.g., Salmonella), nucleic acids (e.g., DNA, RNA, and analogues thereof), polysaccharides, lipopolysaccharides, lipids, fatty acids, non-biological polymers and small bioactive molecules (e.g., toxins, drugs, pesticides, metabolites, hormones, alkaloids, steroids).

Donor and Acceptor Moieties

One of the advantages of the compounds of the invention is that they can be used with a wide range of energy donor and acceptor molecules to construct fluorescence energy transfer probes. An array of fluorophores useful in conjunction with the TIAMs of the invention is known to those of skill in the art. See, for example, Cardullo et al., *Proc. Natl. Acad. Sci. USA* 85: 8790-8794 (1988); Dexter, D. L., *J. of Chemical Physics* 21: 836-850 (1953); Hochstrasser et al., *Biophysical Chemistry* 45: 133-141 (1992); Selvin, P., *Methods in Enzymology* 246: 300-334 (1995); Steinberg, I. *Ann. Rev. Biochem.*, 40: 83-114 (1971); Stryer, L. *Ann. Rev. Biochem.*, 47: 819-846 (1978); Wang et al., *Tetrahedron Letters* 31: 6493-6496 (1990); Wang et al., *Anal. Chem.* 67: 1197-1203 (1995).

A non-limiting list of exemplary donors that can be used in conjunction with the quenchers of the invention is provided in Table 2.

TABLE 2

| Suitable moieties that can be selected as donors or acceptors in FET pairs |
|---|
| 4-acetamido-4'-isothiocyanatostilbene-2,2'disulfonic acid |
| acridine and derivatives: |
|     acridine |
|     acridine isothiocyanate |
| 5-(2'-aminoethyl)aminonaphthalene-1-sulfonic acid (EDANS) |
| 4-amino-N-[3-vinylsulfonyl)phenyl]naphthalimide-3,5 disulfonate |
| N-(4-anilino-1-naphthyl)maleimide |
| anthranilamide |
| BODIPY |
| Brilliant Yellow |
| coumarin and derivatives: |
|     coumarin |
|         7-amino-4-methylcoumarin (AMC, Coumarin 120) |
|         7-amino-4-trifluoromethylcouluarin (Coumaran 151) |
| cyanine dyes |
| cyanosine |
| 4',6-diaminidino-2-phenylindole (DAPI) |
| 5',5''-dibromopyrogallol-sulfonaphthalein (Bromopyrogallol Red) |
| 7-diethylamino-3-(4'-isothiocyanatophenyl)-4-methylcoumarin |
| diethylenetriamine pentaacetate |
| 4,4'-diisothiocyanatodihydro-stilbene-2,2'-disulfonic acid |
| 4,4'-diisothiocyanatostilbene-2,2'-disulfonic acid |
| 5-[dimethylamino]naphthalene-1-sulfonyl chloride (DNS, dansylchloride) |
| 4-(4'-dimethylaminophenylazo)benzoic acid (DABCYL) |
| 4-dimethylaminophenylazophenyl-4'-isothiocyanate (DABITC) |
| eosin and derivatives: |
|     eosin |
|     eosin isothiocyanate |
| erythrosin and derivatives: |
|     erythrosin B |
|     erythrosin isothiocyanate |
| ethidium |
| fluorescein and derivatives: |
|     5-carboxyfluorescein (FAM) |
|     5-(4,6-dichlorotriazin-2-yl)aminofluorescein(DTAF) |
|     2',7'-dimethoxy-4'5'-dichloro-6-carboxyfluorescein (JOE) |
|     fluorescein |
|     fluorescein isothiocyanate |
|     QFITC (XRITC) |
| fluorescamine |
| IR144 |
| IR1446 |

TABLE 2-continued

| Suitable moieties that can be selected as donors or acceptors in FET pairs |
|---|
| Malachite Green isothiocyanate |
| 4-methylumbelliferone |
| ortho cresolphthalein |
| nitrotyrosine |
| pararosaniline |
| Phenol Red |
| B-phycoerythrin |
| o-phthaldialdehyde |
| pyrene and derivatives: |
|     pyrene |
|     pyrene butyrate |
|     succinimidyl 1-pyrene butyrate |
| quantum dots |
| Reactive Red 4 (Cibacron ™ Brilliant Red 3B-A) |
| rhodamine and derivatives: |
|     6-carboxy-X-rhodamine (ROX) |
|     6-carboxyrhodamine (R6G) |
|     lissamine rhodamine B sulfonyl chloride rhodamine (Rhod) |
|     rhodamine B |
|     rhodamine 123 |
|     rhodamine X isothiocyanate |
|     sulforhodamine B |
|     sulforhodamine 101 |
| sulfonyl chloride derivative of sulforhodamine 101 (Texas Red) |
| N,N,N',N'-tetramethyl-6-carboxyrhodamine(TAMRA) |
| tetramethyl rhodamine |
|     tetramethyl rhodamine isothiocyanate (TRITC) |
| riboflavin |
| rosolic acid |
| lanthanide chelate derivatives |

There is a great deal of practical guidance available in the literature for selecting appropriate donor-acceptor pairs for particular probes, as exemplified by the following references: Pesce et al., Eds., FLUORESCENCE SPECTROSCOPY (Marcel Dekker, New York, 1971); White et al., FLUORESCENCE ANALYSIS: A PRACTICAL APPROACH (Marcel Dekker, New York, 1970); and the like. The literature also includes references providing exhaustive lists of fluorescent and chromogenic molecules and their relevant optical properties, for choosing reporter-quencher pairs (see, for example, Berlman, HANDBOOK OF FLUORESCENCE SPECTRA OF AROMATIC MOLECULES, 2nd Edition (Academic Press, New York, 1971); Griffiths, COLOUR AND CONSTITUTION OF ORGANIC MOLECULES (Academic Press, New York, 1976); Bishop, Ed., INDICATORS (Pergamon Press, Oxford, 1972); Haugland, HANDBOOK OF FLUORESCENT PROBES AND RESEARCH CHEMICALS (Molecular Probes, Eugene, 1992) Pringsheim, FLUORESCENCE AND PHOSPHORESCENCE (Interscience Publishers, New York, 1949); and the like. Further, there is extensive guidance in the literature for derivatizing reporter and quencher molecules for covalent attachment via readily available reactive groups that can be added to a molecule.

In a FET pair, it is generally preferred that an absorbance band of the acceptor substantially overlap a fluorescence emission band of the donor. When the donor (fluorophore) is a component of a probe that utilizes fluorescence resonance energy transfer (FRET), the donor fluorescent moiety and the quencher (acceptor) of the invention are preferably selected so that the donor and acceptor moieties exhibit fluorescence resonance energy transfer when the donor moiety is excited. One factor to be considered in choosing the fluorophore-quencher pair is the efficiency of fluorescence resonance energy transfer between them. Preferably, the efficiency of FRET between the donor and acceptor moieties is at least 10%, more preferably at least 50% and even more preferably at least 80%. The efficiency of FRET can easily be empirically tested using the methods both described herein and known in the art.

The efficiency of FRET between the donor-acceptor pair can also be adjusted by changing ability of the donor and acceptor to dimerize or closely associate. If the donor and acceptor moieties are known or determined to closely associate, an increase or decrease in association can be promoted by adjusting the length of a linker moiety, or of the probe itself, between the two fluorescent proteins. The ability of donor-acceptor pair to associate can be increased or decreased by tuning the hydrophobic or ionic interactions, or the steric repulsions in the probe construct. Thus, intramolecular interactions responsible for the association of the donor-acceptor pair can be enhanced or attenuated. Thus, for example, the association between the donor-acceptor pair can be increased by, for example, utilizing a donor bearing an overall negative charge and an acceptor with an overall positive charge.

In addition to fluorophores that are attached directly to a probe, the fluorophores can also be attached by indirect means. In this embodiment, a ligand molecule (e.g., biotin) is preferably covalently bound to the probe species. The ligand then binds to another molecules (e.g., streptavidin) molecule, which is either inherently detectable or covalently bound to a signal system, such as a fluorescent compound of the invention, or an enzyme that produces a fluorescent compound by conversion of a non-fluorescent compound. Useful enzymes of interest as labels include, for example, hydrolases, particularly phosphatases, esterases and glycosidases, or oxidotases, particularly peroxidases. Fluorescent compounds include fluorescein and its derivatives, rhodamine and its derivatives, dansyl, umbelliferone, etc., as discussed above. For a review of various labeling or signal producing systems that can be used, see, U.S. Pat. No. 4,391,904.

Presently preferred fluorophores of use in conjunction with the complexes of the invention, include, for example, xanthene dyes, including fluoresceins, and rhodamine dyes. Many suitable forms of these compounds are widely available commercially with substituents on their phenyl moieties, which can be used as the site for bonding or as the bonding functionality for attachment to an nucleic acid. Another group of preferred fluorescent compounds are the naphthylamines, having an amino group in the alpha or beta position. Included among such naphthylamino compounds are 1-dimethylaminonaphthyl-5-sulfonate, 1-anilino-8-naphthalene sulfonate and 2-p-touidinyl-6-naphthalene sulfonate. Other donors include 3-phenyl-7-isocyanatocoumarin, acridines, such as 9-isothiocyanatoacridine and acridine orange; N-(p-(2-benzoxazolyl)phenyl)maleimide; benzoxadiazoles, stilbenes, pyrenes, and the like.

For clarity of illustration, the discussion below focuses on attaching the complexes of the invention and other fluorophores to nucleic acids. The focus on nucleic acid probes is not intended to limit the scope of probe molecules to which the complexes of the invention can be attached. Those of skill in the art will appreciate that the complexes of the invention can also be attached to small molecules (e.g., small molecular bioactive agents), proteins, peptides, synthetic polymers, solid supports and the like using standard synthetic chemistry or modifications thereof. Further simplifying the discussion is the focus on the use of the compounds of the invention as an energy donor in a FET or FRET pair. It will be appreciated that the TIAM complexes of the invention can be used as either the energy donor or acceptor moiety.

In an exemplary embodiment, in which the probe is a nucleic acid probe, the acceptor molecule is a rhodamine dye. The rhodamine moiety is preferably attached to either the 3'- or the 5'-terminus of the nucleic acid, although internal sites are also accessible for derivitization with donor or accpetor moieties and have utility for selected purposes. Whichever terminus the rhodamine derivative is attached to, the complex of the invention will generally be attached to its antipode, or at a position internal to the nucleic acid chain. The rhodamine acceptor is preferably introduced using a commercially available amidite. Different donor groups of the invention are also preferably introduced using a reactive derivative (e.g., amidite) of the donor. Alternatively, donor groups comprising reactive groups (e.g., isothiocyanates, active esters, etc.) can be introduced via reaction with a reactive moiety on a tether or linker arm attached to the nucleic acid (e.g., hexylamine).

In yet another preferred embodiment, the donor moiety can be attached at the 3'-terminus of a nucleic acid by the use of a derivatized synthesis support. For example, a complexing agent of the invention is tethered to a solid support that is derivatized with an analogue of the complex. Such derivatized supports are well known in the art and are exemplified by a TAMRA (tetramethylrhodamine carboxylic acid) derivative that is attached to a nucleic acid 3'-terminus using a commercially available solid support that is derivatized with an analogue of the TAMRA fluorophore (Biosearch Technologies, Inc.)

In view of the well-developed body of literature concerning the conjugation of small molecules to nucleic acids, many other methods of attaching donor/acceptor pairs to nucleic acids will be apparent to those of skill in the art. For example, rhodamine and fluorescein dyes are conveniently attached to the 5'-hydroxyl of an nucleic acid at the conclusion of solid phase synthesis by way of dyes derivatized with a phosphoramidite moiety (see, for example, Woo et al., U.S. Pat. No. 5,231,191; and Hobbs, Jr., U.S. Pat. No. 4,997,928).

More specifically, there are many linking moieties and methodologies for attaching groups to the 5'- or 3'-termini of nucleic acids, as exemplified by the following references: Eckstein, editor, Nucleic Acids and Analogues: A Practical Approach (IRL Press, Oxford, 1991); Zuckerman et al., *Nucleic Acids Research*, 15: 5305-5321 (1987) (3'-thiol group on nucleic acid); Sharma et al., *Nucleic Acids Research*, 19: 3019 (1991) (3'-sulfhydryl); Giusti et al., *PCR Methods and Applications*, 2: 223-227 (1993) and Fung et al., U.S. Pat. No. 4,757,141 (5'-phosphoamino group via Aminolink™ II available from P.E. Biosystems, CA.) Stabinsky, U.S. Pat. No. 4,739,044 (3-aminoalkylphosphoryl group); Agrawal et al., *Tetrahedron Letters*, 31: 1543-1546 (1990) (attachment via phosphoramidate linkages); Sproat et al., *Nucleic Acids Research*, 15: 4837 (1987) (5-mercapto group); Nelson et al., *Nucleic Acids Research*, 17: 7187-7194 (1989) (3'-amino group), and the like.

Means of detecting fluorescent labels are well known to those of skill in the art. Thus, for example, fluorescent labels are detected by exciting the fluorophore with the appropriate wavelength of light and detecting the resulting fluorescence. The fluorescence can be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product.

Recognition Moieties

As used herein, the term "recognition moiety" refers to molecules that can interact with an analyte via either attractive or repulsive mechanisms. In a preferred embodiment, a recognition moiety is conjugated to a compound of the invention. In another exemplary embodiment, the analyte and the recognition moiety form an intimately associated pair by, for example, covalent bonding, ionic bonding, ion pairing, van der Waals association and the like. In another exemplary embodiment, the analyte and recognition moiety interact by a repulsive mechanism such as incompatible steric characteristics, charge-charge repulsion, hydrophilic-hydrophobic interactions and the like. It is understood that there is overlap between the generic terms "recognition moiety" and "analyte." In a particular application, a species may be an analyte, while in a different application, the species serves as a recognition moiety. In certain embodiments, the compounds of the invention serve as recognition moieties (e.g., when the analyte is a metal ion).

Recognition moieties can be selected from a wide range of small bioactive molecules (e.g., drugs, pesticides, toxins, etc.), organic functional groups (e.g., amines, carbonyls, carboxylates, etc.), biomolecules, metals, metal chelates and organometallic compounds.

The above enumerated, and other molecules, can be attached to the compounds of the invention, to solid substrates and the like by methods well-known to those of skill in the art. Ample guidance can be found in literature devoted to, for example, the fields of bioconjugate chemistry and drug delivery. For example, one of skill, faced with a drug comprising an available amine will be able to choose from among a variety of amine derivatizing reactions, locate an appropriately functionalized partner (e.g., a carboxylic acid terminated thiol) for the organic layer and react the partners under conditions chosen to effect the desired coupling (e.g., dehydrating agents, e.g., dicyclohexylcarbodiimide). See, for example, MODIFICATION OF PROTEINS: FOOD, NUTRITIONAL, AND PHARMACOLOGICAL ASPECTS, Feeney et al., Eds., American Chemical Society, Washington, D.C., 1982, pp. 370-387; POLYMERIC DRUGS AND DRUG DELIVERY SYSTEMS, Dunn et al., Eds., American Chemical Society, Washington, D.C., 1991.

In other exemplary embodiments, the recognition moiety is a biomolecule such as a protein, nucleic acid, peptide or an antibody. Biomolecules useful in practicing the present invention can be derived from any source. The biomolecules can be isolated from natural sources or can be produced by synthetic methods. Proteins can be natural proteins or mutated proteins. Mutations can be effected by chemical mutagenesis, site-directed mutagenesis or other means of inducing mutations known to those of skill in the art. Proteins useful in practicing the instant invention include, for example, enzymes, antigens, antibodies and receptors. Antibodies can be either polyclonal or monoclonal. Peptides and nucleic acids can be isolated from natural sources or can be wholly or partially synthetic in origin.

In those embodiments wherein the recognition moiety is a protein or antibody, the protein can be tethered to a compound of the invention, solid support or a crosslinking agent by any reactive peptide residue available on the surface of the protein. In preferred embodiments, the reactive groups are amines or carboxylates. In particularly preferred embodiments, the reactive groups are the □-amine groups of lysine residues.

Recognition moieties which are antibodies can be used to recognize analytes which are proteins, peptides, nucleic acids, saccharides or small bioactive materials, such as drugs, herbicides, pesticides, industrial chemicals and agents of war. Methods of raising antibodies for specific molecules are well-known to those of skill in the art. See, U.S. Pat. No. 5,147,786, issued to Feng et al. on Sep. 15, 1992; No. 5,334,528, issued to Stanker et al. on Aug. 2, 1994; No. 5,686,237, issued to Al-Bayati, M. A. S. on Nov. 11, 1997; and No. 5,573,922, issued to Hoess et al. on Nov. 12, 1996. Methods for attaching antibodies agents to surfaces are also known in the art. See, Delamarche et al. *Langmuir,* 12: 1944-1946 (1996).

A recognition moiety can be conjugated to a compound of the invention by any of a large number of art-known attachment methods, as discussed above. In one embodiment, the recognition moiety is tethered directly to the hydroxyisophthamidyl chelate through a group on the aromatic hydroxyisophthamidyl nucleus, backbone or amide substituent. In another exemplary embodiment, a reactive bifunctional crosslinking agent is attached reactive group on a chelating agent or complex of the invention and the resulting conjugate is subsequently bound to the recognition moiety via the reactive group on the crosslinking component and a group of complementary reactivity on the recognition moiety. Many useful crosslinking agents can be purchased commercially (Pierce Rockford, Ill.) or can be synthesized using techniques known in the art. Alternatively, the recognition moiety and cross-linking agent are coupled prior to attaching the hydroxyisophthamidyl chelate to the recognition moiety.

Analytes

The materials and methods of the present invention can be used to detect any analyte, or class of analytes, which interact with a recognition moiety in a detectable manner. The interaction between the analyte and recognition moiety can be any physicochemical interaction, including covalent bonding, ionic bonding, hydrogen bonding, van der Waals interactions, repulsive electronic interactions, attractive electronic interactions and hydrophobic/hydrophilic interactions.

In an exemplary embodiment, the interaction is an ionic interaction. In this embodiment, an acid, base, metal ion or metal ion-binding ligand is the analyte. In a still further exemplary embodiment, the interaction is a hydrogen bonding interaction, e.g., the hybridization of a nucleic acid to a nucleic acid having a complementary sequence is detected. In another exemplary embodiment, the interaction is between an enzyme or receptor and a small molecule or peptide, which binds thereto.

In another embodiment, the analyte competes for the recognition moiety with another agent, which has been bound to the recognition moiety prior to introducing the analyte of interest. In this embodiment, it is the process or result of the analyte displacing the pre-bound agent, which causes the detectable levels of fluorescence from the compound of the invention. Suitable combinations of recognition moieties and analytes will be apparent to those of skill in the art.

In presently preferred embodiments, the analyte is a member selected from the group consisting of acids, bases, organic ions, inorganic ions, pharmaceuticals, herbicides, pesticides and biomolecules. Each of these agents, where practicable, can be detected as a vapor or a liquid. These agents can be present as components in mixtures of structurally unrelated compounds, racemic mixtures of stereoisomers, non-racemic mixtures of stereoisomers, mixtures of diastereomers, mixtures of positional isomers or as pure compounds. Within the scope of the invention is a device and a method to detect a particular analyte of interest without interference from other substances within a mixture.

Organic ions, which are substantially non-acidic and non-basic (e.g., quaternary alkylammonium salts), can be detected by a labeled recognition moiety of the invention. For example, a TIAM-labeled recognition moiety with ion exchange properties is useful in the present invention. A specific example is the exchange of a cation such as dodecyltrimethylammonium cation for a metal ion such as sodium. Recognition moieties that form inclusion complexes with organic ions are also of use. For example, crown ethers and cryptands can be used to form inclusion complexes with organic ions such as quaternary ammonium cations.

Inorganic ions such as metal ions and complex ions (e.g., $SO_4^{-2}$, $PO_4^{-3}$) can also be detected using the TIAMs and methods of the invention. Metal ions can be detected, for example, by their complexation or chelation by TIAMs or chelating agents bound to a compound of the invention. In this embodiment, the recognition moiety can be a simple monovalent moiety (e.g., carboxylate, amine, thiol) or can be a more structurally complex agent (e.g., ethylenediaminepentaacetic acid, crown ethers, aza crowns, thia crowns).

Complex inorganic ions can be detected by their ability to compete with the complexes of the invention for bound metal ions in ligand-metal complexes. When a TIAM ligand forms a metal-complex having a thermodynamic stability constant, which is less than that of the complex between the metal and the complex ion, the complex ion will cause the dissociation of the metal ion from the immobilized ligand. If the metal ion is the complexed lanthanide, the fluorescence will be decreased. Methods of determining stability constants for compounds formed between metal ions and ligands are well known to those of skill in the art. Using these stability constants, chelates that are specific for particular ions can be manufactured. See, Martell, A. E., Motekaitis, R. J., D*ETERMINATION AND* U*SE OF* S*TABILITY* C*ONSTANTS*, 2d Ed., VCH Publishers, New York 1992.

In a preferred embodiment, the affinity of an analyte for a particular metal ion is exploited by using a compound of the invention that includes that particular metal ion. The metal ion generally must have available at least one empty coordination site to which the analyte can bind. Alternatively, at least one bond between the metal and the metal-immobilizing agent must be sufficiently labile in the presence of the analyte to allow the displacement of at least one bond of the immobilizing reagent by the analyte. The interaction between the analyte and the metal ion can be detected using a number of art-recognized techniques, including, for example, UV/Vis and fluorescence spectroscopy.

Other combinations of analytes and recognition moieties will be apparent to those of skill in the art.

Probes

The invention provides probes including TIAM moieties conjugated to, for example, a target species, a ligand for a target species (e.g., nucleic acid, peptide, etc.), a small molecule (e.g., drug, pesticide, etc.), and the like. The probes may also be doubly labeled, with a TIAM and a second fluorophore. The TIAM may modify the fluorescence of the second fluorophores or vice-versa. Furthermore, in each of the methods described in this section, a change in fluorescence is detected as an indication of the presence of the target, and that change in fluorescence is preferably detected in-real time. For clarity of illustration, the TIAMs of the invention, when incorporated into FET or FRET probes are generally referred to as the component that generates fluorescence, and the "fluorophores," or non-TIAM agent is referred to as an acceptor or quencher. It will be appreciated that the invention encompasses probes in which the TIAM acts as the quencher.

Nucleic Acid Probes

The ligands of the invention are useful in conjunction with nucleic-acid probes and they can be used as components of detection agents in a variety of DNA amplification/quantification strategies including, for example, 5'-nuclease assay, Strand Displacement Amplification (SDA), Nucleic Acid Sequence-Based Amplification (NASBA), Rolling Circle Amplification (RCA), as well as for direct detection of targets in solution phase or solid phase (e.g., array) assays. Furthermore, the TIAM-derivatized nucleic acids can be used in probes of substantially any format, including, for example, format selected from molecular beacons, scorpion probes, sunrise probes, light up probes and TaqMan□ probes.

Thus in a further aspect, the present invention provides a method for detecting a nucleic acid target sequence. The method includes: (a) contacting the target sequence with a detector nucleic acid; (b) hybridizing the target binding sequence to the target sequence, thereby altering the conformation of the detector nucleic acid, causing a change in a fluorescence parameter; and (c) detecting the change in the fluorescence parameter, thereby detecting the nucleic acid target sequence.

In an exemplary embodiment, the method for detecting a target nucleic acid sequence includes: (a) contacting the target sequence with a detector oligonucleotide that includes a single-stranded target binding sequence. The detector includes a complex of the invention attached thereto and a quencher of light energy having an absorbance band overlapping an emission band of the complex. Moreover, the detector nucleic acid conformation allows fluorescence energy transfer between the complex and the quencher when said complex is excited. In the second step, (b), the target binding sequence is hybridized to the target sequence, thereby altering the conformation of the detector oligonucleotide, causing a change in a fluorescence parameter of the complex, which is detected. The change in the fluorescence parameter is optionally compared with a reference fluorescence property for the nucleic acid construct, wherein the presence of a double stranded oligonucleotide in the sample alters the light energy transfer, resulting in a change in the fluorescence property.

In another aspect, the invention provides a further method for detecting the presence of a nucleic acid target sequence. The method includes: (a) hybridizing to the target sequence a detector nucleic acid comprising a single-stranded target binding sequence and an intramolecularly associated secondary structure 5' to the target binding sequence, wherein at least a portion of the target sequence forms a single stranded tail which is available for hybridization to the target sequence; (b) in a primer extension reaction, synthesizing a complementary strand using the intramolecularly associated secondary structure as a template, thereby dissociating the intramolecularly associated secondary structure and producing a change in a fluorescence parameter; and (c) detecting the change in the fluorescence parameter, thereby detecting the nucleic acid target sequence.

In the methods described in this section, the detector nucleic acid can assume substantially any intramolecularly associated secondary structure, but this structure is preferably a member selected from hairpins, stem-loop structures, pseudoknots, triple helices and conformationally assisted structures. Moreover, the intramolecularly base-paired secondary structure preferably comprises a portion of the target binding sequence. Moreover, the intramolecularly associated secondary structure preferably includes a totally or partially single-stranded endonuclease recognition site.

The complementary strand can be prepared by any art-recognized method for preparing such strands, but is preferably synthesized in a target amplification reaction, and more preferably by extension of the target sequence using the detector nucleic acid as a template.

In another aspect, the invention provides a method for detecting amplification of a target sequence. The method includes the use of an amplification reaction including the following steps: (a) hybridizing the target sequence and a detector nucleic acid. The detector nucleic acid includes a single-stranded target binding sequence and an intramolecularly associated secondary structure 5' to the target binding sequence. At least a portion of the target sequence forms a single stranded tail which is available for hybridization to the target sequence; (b) extending the hybridized detector nucleic acid on the target sequence with a polymerase to produce a detector nucleic acid extension product and separating the detector nucleic acid extension product from the target sequence; (c) hybridizing a primer to the detector nucleic acid extension product and extending the primer with the polymerase, thereby linearizing the intramolecularly associated secondary structure and producing a change in a fluorescence parameter; and (d) detecting the change in the fluorescence parameter, thereby detecting the target sequence.

In yet a further aspect, the invention provides a method of ascertaining whether a first nucleic acid and a second nucleic acid hybridize. In this method, the first nucleic acid includes a complex according to the invention. The method includes: (a) contacting the first nucleic acid with the second nucleic acid; (b) detecting an alteration in a fluorescent property of a member selected from the first nucleic acid, the second nucleic acid and a combination thereof, thereby ascertaining whether the hybridization occurs.

A probe bearing both a TIAM complex and a fluorophore can be used or, alternatively, one or more of the nucleic acids can be singly labeled with a TIAM complex or fluorophore. When a nucleic acid singly labeled with a TIAM complex is the probe, the interaction between the first and second nucleic acids can be detected by observing the quenching of the native nucleic acid fluorescence or, more preferably, the quenching of the fluorescence of a TIAM (or fluorophore) attached to the second nucleic acid.

In addition to their general utility in species designed to probe nucleic acid amplification, detection and quantification, the TIAM complexes can be used in substantially any nucleic acid probe format now known or later discovered. For example, the TIAMs of the invention can be incorporated into probe motifs, such as Taqman probes (Held et al., *Genome Res.* 6: 986-994 (1996), Holland et al., *Proc. Nat. Acad. Sci. USA* 88: 7276-7280 (1991), Lee et al., *Nucleic Acids Res.* 21: 3761-3766 (1993)), molecular beacons (Tyagi et al., *Nature Biotechnology* 14:303-308 (1996), Jayasena et al., U.S. Pat. No. 5,989,823, issued Nov. 23, 1999)) scorpion probes (Whitcomb et al., *Nature Biotechnology* 17: 804-807 (1999)), sunrise probes (Nazarenko et al., *Nucleic Acids Res.* 25: 2516-2521 (1997)), peptide nucleic acid (PNA)-based light up probes (Kubista et al., WO 97/45539, December 1997), double-strand specific DNA dyes (Higuchi et al, *Bio/Technology* 10: 413-417 (1992), Wittwer et al, *BioTechniques* 22: 130-138 (1997)) and the like. These and other probe motifs with which the present TIAMs can be used are reviewed in N*ONISOTOPIC* DNA Probe Techniques, Academic Press, Inc. 1992.

The nucleic acids for use in the probes of the invention can be any suitable size, and are preferably in the range of from about 10 to about 100 nucleotides, more preferably from about 10 to about 80 nucleotides and more preferably still, from about 20 to about 40 nucleotides. The precise sequence and length of a nucleic acid probe of the invention depends in part on the nature of the target polynucleotide to which it binds. The binding location and length may be varied to achieve appropriate annealing and melting properties for a particular embodiment. Guidance for making such design choices can be found in many art-recognized references.

Preferably, the 3'-terminal nucleotide of the nucleic acid probe is blocked or rendered incapable of extension by a nucleic acid polymerase. Such blocking is conveniently carried out by the attachment of a donor or acceptor molecule to the terminal 3'-position of the nucleic acid probe by a linking moiety.

The nucleic acid can comprise DNA, RNA or chimeric mixtures or derivatives or modified versions thereof. Both the probe and target nucleic acid can be present as a single strand, duplex, triplex, etc. In addition to being labeled with an molecular energy transfer donor and a molecular energy transfer acceptor moiety, the nucleic acid can be modified at the base moiety, sugar moiety, or phosphate backbone with other groups such as radioactive labels, minor groove binders, intercalating agents an the like.

For example, the nucleic acid can comprise at least one modified base moiety which is selected from the group including, but not limited to, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, $N^6$-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methyl ester, uracil-5-oxyacetic acid (v), 5-methyl-2-thiouracil, 3-(3-amino-3-$N^2$-carboxypropyl) uracil, (acp3)w, and 2,6-diaminopurine.

In another embodiment, the nucleic acid comprises at least one modified sugar moiety selected from the group including, but not limited to, arabinose, 2-fluoroarabinose, xylulose, and hexose.

In yet another embodiment, the nucleic acid comprises at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

Phosphodiester linked nucleic acids bearing probes of the invention can be synthesized by standard methods known in the art, e.g. by use of an automated DNA synthesizer (such as are commercially available from P.E. Biosystems, etc.) using commercially available amidite chemistries. Nucleic acids bearing modified phosphodiester linking groups can be synthesized by methods known in the art. For example, phosphorothioate nucleic acids may be synthesized by the method of Stein et al. (*Nucl. Acids Res.* 16:3209 (1988)), methylphosphonate nucleic acids can be prepared by use of controlled pore glass polymer supports (Sarin et al., *Proc. Natl. Acad. Sci. U.S.A.* 85:7448-7451 (1988)). Other methods of synthesizing both phosphodiester- and modified phosphodiester-linked nucleic acids will be apparent to those of skill in the art.

Nucleic acid probes of the invention can be synthesized by a number of approaches, e.g., Ozaki et al., *Nucleic Acids Research*, 20: 5205-5214 (1992); Agrawal et al., *Nucleic Acids Research*, 18: 5419-5423 (1990); or the like. The nucleic acid probes of the invention are conveniently synthesized on an automated DNA synthesizer, e.g., a P.E. Biosystems, Inc. (Foster City, Calif.) model 392 or 394 DNA/RNA Synthesizer, using standard chemistries, such as phosphoramidite chemistry (see, for example, disclosed in the following references: Beaucage et al., *Tetrahedron*, 48: 2223-2311 (1992); Molko et al., U.S. Pat. No. 4,980,460; Koster et al., U.S. Pat. No. 4,725,677; Caruthers et al., U.S. Pat. Nos. 4,415,732; 4,458,066; and 4,973,679. Alternative chemistries resulting in non-natural backbone groups, such as phosphorothioate, phosphoramidate, and the like, can also be employed.

When the nucleic acids are synthesized utilizing an automated nucleic acid synthesizer, the stabilizing moiety, energy transfer donor and energy transfer acceptor moieties are preferably introduced during automated synthesis. Alternatively, one or more of these moieties can be introduced either before or after the automated synthesis procedure has commenced. In another exemplary embodiment, one or more of these moieties is introduced after the automated synthesis is complete.

The quencher moiety is preferably separated from the TIAM complex by at least about 10 nucleotides, and more preferably by at least about 15 nucleotides. The quencher moiety is preferably attached to either the 3'- or 5'-terminal nucleotides of the probe. The TIAM complex is also preferably attached to either the 3'- or 5'-terminal nucleotides of the probe. More preferably, the donor and acceptor moieties are attached to the 3'- and 5'- or 5'- and 3'-terminal nucleotides of the probe, respectively.

Once the desired nucleic acid is synthesized, it is preferably cleaved from the solid support on which it was synthesized and treated, by methods known in the art, to remove any protecting groups present (e.g., 60° C., 5 h, concentrated ammonia). In those embodiments in which a base-sensitive group is attached to the nucleic acids (e.g., TAMRA), the deprotection will preferably use milder conditions (e.g., butylamine:water 1:3, 8 hours, 70° C.). Deprotection under these conditions is facilitated by the use of quick deprotect amidites (e.g., dC-acetyl, dG-dmf).

Following cleavage from the support and deprotection, the nucleic acid is purified by any method known in the art, including chromatography, extraction and gel purification. In a preferred embodiment, the nucleic acid is purified using HPLC. The concentration and purity of the isolated nucleic acid is preferably determined by measuring the optical density at 260 nm in a spectrophotometer.

Peptide Probes

Peptides, proteins and peptide nucleic acids that are labeled with a fluorophore and a complex of the invention can be used in both in vivo and in vitro enzymatic assays.

Thus, in another aspect, the present invention provides a method for determining whether a sample contains an enzyme. The method comprises: (a) contacting the sample with a peptide construct that includes a peptide sequence, having a cleavage site for the enzyme; a TIAM covalently bound to the peptide; and a quencher of light energy, which is also covalently bound to said peptide sequence. The quencher has an absorbance band overlapping an emission band of the TIAM. The peptide sequence conformation allows light energy transfer between the TIAM and the quencher when the TIAM is excited. The TIAM is excited by light of an appropriate wavelength and a fluorescence property of the sample is determined. The activity of the enzyme in the sample alters the light energy transfer, resulting in a change in a fluorescence property. The fluorescence property is optionally compared with a reference fluorescence property for the peptide construct.

When the probe is used to detect an enzyme, such as a degradative enzyme (e.g., protease), and a degree of fluorescence resonance energy transfer that is lower than an expected amount is observed, this is generally indicative of the presence of an enzyme. The degree of fluorescence resonance energy transfer in the sample can be determined, for example, as a function of the amount of fluorescence from the donor moiety, the amount of fluorescence from the acceptor moiety, the ratio of the amount of fluorescence from the donor moiety to the amount of fluorescence from the acceptor moiety or the excitation state lifetime of the donor moiety.

The assay also is useful for determining the amount of enzyme in a sample by determining the degree of fluorescence resonance energy transfer at a first and second time after contact between the enzyme and the tandem construct, and determining the difference in the degree of fluorescence resonance energy transfer. The difference in the degree of fluorescence resonance energy transfer reflects the amount of enzyme in the sample.

The assay methods also can also be used to determine whether a compound alters the activity of an enzyme, i.e., screening assays. Thus, in a further aspect, the invention provides methods of determining the affect on an enzyme of the presence of a selected species in an analysis mixture. The method includes contacting a sample comprising the enzyme and the species with a peptide construct as described above. The TIAM is excited and a fluorescence property of the sample is determined. The fluorescence property is optionally compared with a reference fluorescence property for the peptide construct.

In a typical embodiment, the fluorescence property of the peptide construct before and after the addition of the species to the analysis mixture will be compared to determine the affect of the species on the enzyme. Thus, the amount of enzyme activity in the sample is determined as a function of the degree of fluorescence resonance energy transfer in the sample and the amount of activity in the sample is compared with a standard activity for the same amount of the enzyme. A difference between the amount of enzyme activity in the sample and the standard activity indicates that the species alters the activity of the enzyme.

Representative enzymes with which the present invention can be practiced include, for example, trypsin, enterokinase, HIV-1 protease, prohormone convertase, interleukin-1b-converting enzyme, adenovirus endopeptidase, cytomegalovirus assemblin, leishmanolysin, □-secretase for amyloid precursor protein, thrombin, renin, angiotensin-converting enzyme, cathepsin-D and a kininogenase, and proteases in general.

Proteases play essential roles in many disease processes such as Alzheimer's, hypertension, inflammation, apoptosis, and AIDS. Compounds that block or enhance their activity have potential as therapeutic agents. Because the normal substrates of peptidases are linear peptides and because established procedures exist for making non-peptidic analogs, compounds that affect the activity of proteases are natural subjects of combinatorial chemistry. Screening compounds produced by combinatorial chemistry requires convenient enzymatic assays.

The most convenient assays for proteases are based on fluorescence resonance energy transfer from a donor fluorophore to an acceptor placed at opposite ends of a short peptide chain containing the potential cleavage site (see, Knight C. G., *Methods in Enzymol.* 248:18-34 (1995)). Proteolysis separates the fluorophore and acceptor, resulting in increased intensity in the emission of the donor fluorophore. Existing protease assays use short peptide substrates incorporating unnatural chromophoric amino acids, assembled by solid phase peptide synthesis.

Assays of the invention are also useful for determining and characterizing substrate cleavage sequences of proteases or for identifying proteases, such as orphan proteases. In one embodiment the method involves the replacement of a defined linker moiety amino acid sequence with one that contains a randomized selection of amino acids. A library of fluorescent TIAM-bearing probes, wherein the fluorophore and the TIAM complex are linked by a randomized peptide linker moiety can be generated using recombinant engineering techniques or synthetic chemistry techniques. Screening the members of the library can be accomplished by measuring a signal related to cleavage, such as fluorescence energy transfer, after contacting the cleavage enzyme with each of the library members of the tandem fluorescent peptide construct. A degree of fluorescence resonance energy transfer that is lower than an expected amount indicates the presence of a linker sequence that is cleaved by the enzyme. The degree of fluorescence resonance energy transfer in the sample can be determined, for example, as a function of the amount of fluorescence from the donor moiety, the amount of fluorescence from the acceptor donor moiety, or the ratio of the amount of fluorescence from the donor moiety to the amount of fluorescence from the acceptor moiety or the excitation state lifetime of the donor moiety.

In the tandem constructs of the invention, the donor and acceptor moieties are connected through a linker moiety. The linker moiety, preferably, includes a peptide moiety, but can be another organic molecular moiety, as well. In a preferred embodiment, the linker moiety includes a cleavage recognition site specific for an enzyme or other cleavage agent of interest. A cleavage site in the linker moiety is useful because when a tandem construct is mixed with the cleavage agent, the linker is a substrate for cleavage by the cleavage agent. Rupture of the linker moiety results in separation of the fluorophore and the TIAM complex of the invention. The separation is measurable as a change in FRET.

When the cleavage agent of interest is a protease, the linker can comprise a peptide containing a cleavage recognition sequence for the protease. A cleavage recognition sequence for a protease is a specific amino acid sequence recognized by the protease during proteolytic cleavage. Many protease cleavage sites are known in the art, and these and other cleavage sites can be included in the linker moiety. See, e.g., Matayoshi et al. *Science* 247: 954 (1990); Dunn et al. *Meth. Enzymol.* 241: 254 (1994); Seidah et al. *Meth. Enzymol.* 244: 175 (1994); Thornberry, *Meth. Enzymol.* 244: 615 (1994); Weber et al. *Meth. Enzymol.* 244: 595 (1994); Smith et al. *Meth. Enzymol.* 244: 412 (1994); Bouvier et al. *Meth. Enzymol.* 248: 614 (1995), Hardy et al., in AMYLOID PROTEIN PRECURSOR IN DEVELOPMENT, AGING, AND ALZHEIMER'S DISEASE, ed. Masters et al. pp. 190-198 (1994).

Solid Support Immobilized TIAM Analogues

The TIAMs of the invention can be immobilized on substantially any polymer, biomolecule, and solid or semi-solid material having any useful configuration. Moreover, any conjugate comprising one or more TIAMs can be similarly immobilized. When the support is a solid or semi-solid, examples of preferred types of supports for immobilization of the nucleic acid probe include, but are not limited to, controlled pore glass, glass plates, polystyrene, avidin coated polystyrene beads, cellulose, nylon, acrylamide gel and activated dextran. These solid supports are preferred because of their chemical stability, ease of functionalization and well-defined surface area. Solid supports such as, controlled pore glass (CPG, 500 Å, 1000 Å) and non-swelling high cross-linked polystyrene (1000 Å) are particularly preferred.

According to the present invention, the surface of a solid support is functionalized with a TIAM complex of the invention or a species including a TIAM complex. For clarity of illustration, the following discussion focuses on attaching a reactive TIAM ligand or complex to a solid support. The following discussion is also broadly relevant to attaching a species that includes within its structure a reactive TIAM to a solid support, and the attachment of such species and reactive TIAM analogues to other molecules and structures.

In an exemplary embodiment, the TIAM is attached to a solid support by forming a bond between a reactive group on the TIAM and a reactive group on the surface of the solid support or a linker attached to the solid support, thereby derivatizing the solid support with one or more TIAM analogues. The bond between the solid support and the TIAM is preferably a covalent bond, although ionic, dative and other such bonds are useful as well. Reactive groups which can be used in practicing the present invention are discussed in detail above and include, for example, amines, hydroxyl groups, carboxylic acids, carboxylic acid derivatives, alkenes, sulfhydryls, siloxanes, etc.

A large number of solid supports appropriate for practicing the present invention are available commercially and include, for example, peptide synthesis resins, both with and without attached amino acids and/or peptides (e.g., alkoxybenzyl alcohol resin, aminomethyl resin, aminopolystyrene resin, benzhydrylamine resin, etc. (Bachem)), functionalized controlled pore glass (BioSearch Technologies, Inc.), ion exchange media (Aldrich), functionalized membranes (e.g., □COOH membranes; Asahi Chemical Co., Asahi Glass Co., and Tokuyama Soda Co.), and the like.

Moreover, for applications in which an appropriate solid support is not commercially available, a wide variety of reaction types are available for the functionalization of a solid support surface. For example, supports constructed of a plastic such as polypropylene, can be surface derivatized by chromic acid oxidation, and subsequently converted to hydroxylated or aminomethylated surfaces. The functionalized support is then reacted with a TIAM of complementary reactivity, such as a TIAM active ester, acid chloride or sulfonate ester, for example. Supports made from highly crosslinked divinylbenzene can be surface derivatized by chloromethylation and subsequent functional group manipulation. Additionally, functionalized substrates can be made from etched, reduced polytetrafluoroethylene.

When the support is constructed of a siliceous material such as glass, the surface can be derivatized by reacting the surface Si—OH, SiO—H, and/or Si—Si groups with a functionalizing reagent.

Nucleic Acid Capture Probes

In one embodiment, an immobilized nucleic acid comprising a TIAM is used as a capture probe. The nucleic acid probe can be attached directly to a solid support, for example by attachment of the 3'- or 5'-terminal nucleotide of the probe to the solid support. More preferably, however, the probe is attached to the solid support by a linker (i.e., spacer arm, supra). The linker serves to distance the probe from the solid support. The linker is most preferably from about 5 to about 30 atoms in length, more preferably from about 10 to about 50 atoms in length.

In yet another preferred embodiment, the solid support is also used as the synthesis support in preparing the probe. The length and chemical stability of the linker between the solid support and the first 3'-unit of nucleic acid play an important role in efficient synthesis and hybridization of support bound nucleic acids. The linker arm should be sufficiently long so that a high yield (>97%) can be achieved during automated synthesis. The required length of the linker will depend on the particular solid support used. For example, a six atom linker is generally sufficient to achieve a >97% yield during automated synthesis of nucleic acids when high cross-linked polystyrene is used as the solid support. The linker arm is preferably at least 20 atoms long in order to attain a high yield (>97%) during automated synthesis when CPG is used as the solid support.

Hybridization of a probe immobilized on a solid support generally requires that the probe be separated from the solid support by at least 30 atoms, more preferably at least 50 atoms. In order to achieve this separation, the linker generally includes a spacer positioned between the linker and the 3'-terminus. For nucleic acid synthesis, the linker arm is usually attached to the 3'-OH of the 3'-terminus by an ester linkage which can be cleaved with basic reagents to free the nucleic acid from the solid support.

A wide variety of linkers are known in the art, which may be used to attach the nucleic acid probe to the solid support. The linker may be formed of any compound, which does not significantly interfere with the hybridization of the target sequence to the probe attached to the solid support. The linker may be formed of, for example, a homopolymeric nucleic acid, which can be readily added on to the linker by automated synthesis. Alternatively, polymers such as functionalized polyethylene glycol can be used as the linker. Such polymers are presently preferred over homopolymeric nucleic acids because they do not significantly interfere with the hybridization of probe to the target nucleic acid. Polyethylene glycol is particularly preferred because it is commercially available, soluble in both organic and aqueous media, easy to functionalize, and completely stable under nucleic acid synthesis and post-synthesis conditions.

The linkages between the solid support, the linker and the probe are preferably not cleaved during synthesis or removal of base protecting groups under basic conditions at high temperature. These linkages can, however, be selected from groups that are cleavable under a variety of conditions. Examples of presently preferred linkages include carbamate, ester and amide linkages.

Acrylamide-Immobilized Probes

In another preferred embodiment, a species is within a matrix, such as an acrylamide matrix and the species bears a TIAM, or the presence of the immobilized species is ascertained using a probe bearing a TIAM. In a preferred embodiment, the immobilization is accomplished in conjunction with the "acrydite" process commercialized by Mosaic Technologies (Cambridge, Mass., see, Rehman et al., *Nucleic Acids Research*, 27: 649-655 (1999)). The acrydite method allows immobilization of alkene labeled capture probes within a polymerized polyacrylamide network. When target mixes are run past the immobilized probe band under electrophoresis conditions, the target nucleic acid is captured substantially quantitatively. However, detection of this event currently requires a second probe. In one embodiment, probes bearing a TIAM, and/or a fluorphore, are immobilized in an acrylamide matrix and subsequently contacted with the target mix. By using fluorescent probes as capture probes, signals from target mixes can be directly detected in real time.

Microarrays

The invention also provides microarrays including immobilized TIAMs and compounds functionalized with TIAMs. Moreover, the invention provides methods of interrogating microarrays using probes that are functionalized with TIAMs. The immobilized species and the probes are selected from substantially any type of molecule, including, but not limited to, small molecules, peptides, enzymes nucleic acids and the like.

Nucleic acid microarrays consisting of a multitude of immobilized nucleic acids are revolutionary tools for the generation of genomic information, see, Debouck et al., in supplement to *Nature Genetics*, 21:48-50 (1999). The discussion that follows focuses on the use of TIAMs in conjunction with nucleic acid microarrays. This focus is intended to be illustrative and does not limit the scope of materials with which this aspect of the present invention can be practiced.

Thus, in another preferred embodiment, the compounds of the present invention are utilized in a microarray format. The TIAMs, or species bearing TIAMs can themselves be components of a microarray or, alternatively they can be utilized as a tool to screen components of a microarray.

Thus, in a preferred embodiment, the present invention provides a method of screening a microarray. The method includes contacting the members of the microarray with a TIAM-bearing probe and interrogating the microarray for regions of fluorescence. The fluorescent regions are indicative of the presence of an interaction between the TIAM-bearing probe and a microarray component. In another version of this method, the microarray is interrogated for regions in which fluorescence is quenched, again indicating the presence of an interaction between the TIAM-bearing probe and a component of the microarray.

In another preferred embodiment, the array comprises immobilized TIAM-bearing FET probes as the interrogating species. In this embodiment, the probe "turns on" when hybridized to its target. Such arrays are easily prepared and read, and can be designed to give quantitative data. Arrays comprising TIAM-bearing probes are valuable tools for expression analysis and clinical genomic screening.

In another preferred embodiment, the immobilized TIAM-bearing probe is not a FET probe. A microarray based on such as format can be used to probe for the presence of interactions between an analyte and the immobilized probe by, for example, observing the quenching of analyte fluorescence upon interaction between the probe and analyte.

In a further preferred embodiment, the microarrays comprise n probes that comprise identical or different nucleic acid sequences. Alternatively, the microarray can comprise a mixture of n probes comprising groups of identical and different nucleic acid sequences identical nucleic acid sequences). In a preferred embodiment, n is a number from 2 to 100, more preferably, from 10 to 1,000, and more preferably from 100 to 10,000. In a still further preferred embodiment, the n probes are patterned on a substrate as n distinct locations in a manner that allows the identity of each of the n locations to be ascertained.

In yet another preferred embodiment, the invention also provides a method for preparing a microarray of n TIAM-bearing probes. The method includes attaching TIAM-bearing probes to selected regions of a substrate. A variety of methods are currently available for making arrays of biological macromolecules, such as arrays nucleic acid molecules. See, Lehrach, et al., HYBRIDIZATION FINGERPRINTING IN GENOME MAPPING AND SEQUENCING, GENOME ANALYSIS, Vol. 1, Davies et al, Eds., Cold Springs Harbor Press, pp. 39-81 (1990); Pirrung et al. (U.S. Pat. No. 5,143,854, issued 1992), and also by Fodor et al., (*Science*, 251: 767-773 (1991); Southern et al. (*Genomics*, 13: 1008-1017 (1992); Khrapko, et al., *DNA Sequence*, 1: 375-388 (1991); Kleinfield et al., *J. Neurosci.* 8: 4098-120 (1998); Kumar et al., *Langmuir* 10: 1498-511 (1994); Xia, Y., *J. Am. Chem. Soc.* 117: 3274-75 (1995); Hickman et al., *J. Vac. Sci. Technol.* 12: 607-16 (1994); Kleinfield et al., *J. Neurosci.* 8: 4098-120 (1998); and Mrkish et al. *Ann. Rev. Biophys. Biomol. Struct.* 25: 55-78 (1996).

Kits

In another aspect, the present invention provides kits containing one or more of the TIAMs or TIAM-bearing compositions of the invention. In one embodiment, a kit will include a reactive TIAM derivative and directions for attaching this derivative to another molecule. In another embodiment, the kit include a TIAM-labeled nucleic acid that optionally is also labeled with a second fluorophore or quencher and directions for using this nucleic acid in one or more assay formats. Other formats for kits will be apparent to those of skill in the art and are within the scope of the present invention.

The invention provides kits for practicing the methods noted above. The kits can include any of the compositions noted above, and optionally further include additional components such as instructions to practice the methods, one or more containers or compartments (e.g., to hold the assay components, nucleic acids, antibodies, inhibitors or the like), a robotic armature for mixing kit components or the like.

The invention also provides integrated systems for performing the methods disclosed herein. For example, in the performing assays, in one embodiment, the delivery of individual compounds or compound components is accomplished by means of a robotic armature which transfers fluid from a source to a destination, a controller which controls the robotic armature, a label detector, a data storage unit which records label detection, and an assay component such as a microtiter dish comprising a well. When a labeled compound is used, it is detected by means of the label detector.

A number of robotic fluid transfer systems are available, or can easily be made from existing components. For example, a Zymate XP (Zymark Corporation; Hopkinton, Mass.) automated robot using a Microlab 2200 (Hamilton; Reno, Nev.) pipetting station can be used to transfer parallel samples to 96 well microtiter plates to set up several parallel simultaneous ligation reactions.

Optical Amplification

Optical signals are important for transmitting information. However, when an optical signal is transmitted through an optical fiber, attenuation will always occur to a certain extent, such that it is necessary to amplify the signal after a certain distance (typically in the order of about 50-100 km). Conventionally, for that purpose an electronic amplifier is used. At the amplifier station, the optical signal must then be converted into an electrical signal, which is amplified in an electronic amplifier, after which the amplified electrical signal is converted back into an optical signal. This involves not only the disadvantage that an amplifier station has a rather complicated structure with rather a large number of parts, among which optical/electrical converters and electrical/optical converters, but this also implies that the bandwidth and bit-rate of the overall system is limited by the electronic components. Therefore, optical fiber amplifiers have recently been developed, i.e. amplifiers, which amplify the optical signal directly and do not need a conversion into an electrical signal. Such devices are disclosed in, for example, Yan et al., U.S. Pat. No. 5,982,973, issued Nov. 9, 1999; Kleinerman, U.S. Pat. No. 5,928,222, issued Jul. 27, 1999; Desurvire, *Physics Today,* January 1994, 20-27; Sloof et al., *J. Appl. Phys.* 83: 497 (1998).

Thus, in another embodiment, the present invention provides a substrate for the transmission and amplification of light, said substrate comprising a compound of the invention. The compound of the invention can be incorporated into the substrate in any manner known in the art, including, but not limited to, covalent attachment, coating, doping, and the like.

The substrate can include any material useful for a particular application, including, but not limited to, glass, organic polymers, inorganic polymers and combinations thereof.

Also provided is a method for amplifying light transmitted by the substrate derivatized with a compound of the invention, as described above. The method comprises transmitting light through such a substrate, thereby amplifying the light.

The substrates and methods of the invention can be used in fiber optic devices, sensors (see, for example, Kopelman et al., U.S. Pat. No. 5,627,922; and Pinkel et al., U.S. Pat. No. 5,690,894), fiber optic "refrigerators" and the like.

Medical Applications

The compounds of the invention can also be used to treat malignant tumors via photodynamic therapy (PDT). Additionally, the complexes of the invention be used in vivo and in vitro as chelating agents for: (1) certain paramagnetic metal ions to achieve higher contrast in magnetic resonance imaging (MRI); and (2) radioactive metal ions for tumor imaging in single-photon-emission tomography (SPECT) or position emission tomography (PET) and/or in radioisotope-mediated radiation therapy. Thus, appropriately radiolabeled phthalamide chelates can be imaged noninvasively in nuclear medicine employing SPECT or PET. See, for example, Margerum et al., U.S. Pat. No. 6,010,681; and Woodburn et al., U.S. Pat. No. 6,022,526.

Separations

In another preferred embodiment, the specificity of the compounds of the invention for particular ions in solution is exploited to separate those ions from other solutes, including ions for which a compound of the invention has a lower affinity or specificity. In a preferred embodiment, the TIAMs are used to separate one lanthanide ion from another. Many examples of ion selective or ion specific chelating agents are known in the art. See, for example, Izatt, et al. SYNTHESIS OF MACROCYCLES, Wiley-Interscience, New York, 1987; and Martell et al., DETERMINATION AND USE OF STABILITY CONSTANTS, $2^{nd}$ Ed., VCH Publishers, New York, 1992.

The materials, methods and devices of the present invention are further illustrated by the examples that follow. These examples are offered to illustrate, but not to limit the claimed invention.

EXAMPLES

Materials and Methods

All chemicals were used as obtained without further purification, unless otherwise noted. NMR spectra were determined at 300 MHz, 400 MHz and 500 MHz on superconducting FT spectrometers in the laboratory (University of California, Berkeley, Calif.). Mass spectra were obtained with Atlas MS-12, Consolidated 12-110B or Kratos MS50 spectrometers. Elemental analyses were performed by the Microanalytical Laboratory, at College of Chemistry, UC Berkeley NMR.

Example 1

The synthesis of a 2-methoxy-1,3,5-tris-(2-thioxo-thiazolidine-3-carbonyl)-benzene core for a triamide of the invention is described. Scheme 1 set forth a synthetic scheme corresponding to the present example 1.1 Synthesis of
2,6-bis-hydroxymethyl-4-methyl-1-methoxybenzene
(2)

To a solution of 2,6-bis(hydroxymethyl)-p-cresol (1) (250 g, 1.48 mol), NaOH pellet (90 g, 2.25 mol) in water (2 L), dimethyl sulfate (105 g, 0.84 mol) was added slowly while stirring. The temperature of the reaction mixture was maintained below 40° C. during dimethyl sulfate addition. Copious white precipitate formed upon standing overnight, the white product (150 g) was collected by filtration as the first crop. Dimethyl sulfate (31 g, 0.25 mol) was added to the mother liquor, and the mixture was stirred at room temperature for 5 days. During this time the volume of the mother liquor was reduced to half of its original volume and 70 g of product was collected as the second crop by filtration. Total yield, 220 g (81%).

$^1$H NMR (500 MHz, CDCl$_3$, 25° C.): □2.218 (s, 2H, OH), 2.307 (s, 3H, CH$_3$), 3.806 (s, 3H, CH$_3$), 4.678 (s, br, 4H, CH$_2$), 7.124 (s, 2H, ArH).

$^{13}$C NMR (500 MHz, CDCl$_3$, 25° C.): □55.20, 59.13, 110.78, 128.36, 129.84, 144.83, 152.41.

1.2 Synthesis of 2-methoxy-benzene-1,3,5-tricarboxylic acid (3)

To a mixture of compound 2 (91 g, 0.5 mol) and water (3 L) in a 5 L flask equipped with a mechanical stirrer and heating mantle, sodium hydroxide (10 g, 0.25 mol) was added, giving a clear solution. Potassium permanganate (211 g, 1.34 mol) was added in several batches to the solution over 2 h without heating. The resultant brown slurry was heated to 80° C., and potassium permanganate (158 g, 1 mol) was added in batches with stirring for 4 h. The reaction temperature was raised to 90° C. and the progress of the reaction was monitored by proton NMR (additional potassium permanganate may be added to ensure completion of the oxidation reaction). The slurry was then filtered to remove the large amount of MnO$_2$ and the volume of filtrate was reduced to 500 mL, and acidified with conc. HCl. Pure product was obtained through the gradual crystallization of a snow-white solid, which was collected by filtration. Yield 90 g (75%).

$^1$H NMR (500 MHz, D$_2$O—NaOD, 25° C.): □3.791 (br s, 3H, CH$_3$), 7.749 (s, 2H, ArH).

$^{13}$C NMR (500 MHz, DMSO-d$_6$, 25° C.): □63.43, 124.85, 125.41, 136.42, 162.54, 167.09, 167.53.

1.3 Preparation of 2-methoxy-1,3,5-benzenetricarbonyl trichloride (4)

To a solution of compound 3 (60 g, 0.25 mol) in dry dioxane, thionyl chloride (36 g, 0.3 mol) and a drop of DMF were added with stirring. The mixture was heated to reflux overnight under N$_2$, then all the volatiles were removed by reduced pressure distillation. The residue was co-evaporated twice with dry dioxane. A pale brown oil was obtained. The raw yield was 100%. It was used without further purification.

$^1$H NMR (500 MHz, CDCl$_3$, 25° C.): □4.052 (s, 3H, CH$_3$), 8.665 (s, 2H, ArH).

$^{13}$C NMR (500 MHz, CDCl$_3$, 25° C.): □65.02, 128.21, 130.34, 139.39, 163.06, 163.44, 165.41.

1.4 Synthesis of 2-methoxy-1,3,5-tris-(2-thioxo-thiazolidine-3-carbonyl)-benzene (5)

To a solution of 2-mercaptothiozaline (66 g, 0.55 mol) and 70 mL of triethylamine in dry dichloromethane (400 mL), a solution of compound 4 (73 g, 0.25 mol) in dry dichloromethane (300 mL) was added dropwise with stirring and cooling. The reaction turned yellow immediately. The yellow slurry was stirred overnight and then filtered. The yellow filter cake was washed thoroughly with water, air dried and recrystallized from isopropanol to give 90 g of product. The yellow filtrate was evaporated to dryness, dissolved in CH$_2$Cl$_2$, extracted with 1N HCl and 1N KOH successively, then purified by flash chromatography to give 26 g of product (yield 86%).

$^1$H NMR (500 MHz, CDCl$_3$, 25° C.): □3.143 (t, 6H, J=7.5 Hz, CH$_2$), 3.908 (s, 3H, CH$_3$), 4.460 (t, 2H, J=7.0 Hz, CH$_2$), 4.570 (t, 6H, J=7.5 Hz, CH$_2$), 7.740 (s, 2H, ArH).

$^{13}$C NMR (500 MHz, CDCl$_3$, 25° C.): □29.24, 29.84, 55.49, 56.50, 62.53, 127.24, 127.72, 133.15, 157.66, 166.19, 168.77.

Example 2

The reaction of a 2-methoxy-1,3,5-tris-(2-thioxo-thiazolidine-3-carbonyl)-benzene core for a triamide with various amines is set forth. The example demonstrates that the core can be derivatized to form an amide that has diversity in the amine component. A representative synthetic scheme is set forth in Scheme 2.

2.1 Synthesis of 4-methoxy-N-methyl-3,5-bis-(2-thioxo-thiazolidine-3-carbonyl)-benzamide (6A)

To a slurry of the trithiazolide 5 (27.1 g, 0.05 mol) in dichloromethane (600 mL), a mixture of 2 mL methylamine solution (40% wt in water, d=0.902) and isopropanol (30 mL) was added dropwise over 48 h. The reaction mixture was applied directly onto a gradient flash silica column (1-5% methanol in methylene chloride). The desired product was obtained as a thick, yellow oil, yield 7.5 g (71% based on the methylamine). 12.8 g of unreacted starting trithiazolide was recovered during the separation.

$^1$H NMR (500 MHz, CDCl$_3$, 25° C.): □2.295 (d, 3H, J=4.5, NCH$_3$), 3.390 (t, 4H, J=7.5 Hz, CH$_2$), 3.877 (s, 3H, CH$_3$), 4.554 (t, 2H, J=7.5 Hz, CH$_2$), 6.825 (s, 1H, AmideH), 7.832 (s, 2H, ArH).

$^{13}$C NMR (500 MHz, CDCl$_3$, 25° C.): □26.82, 29.26, 55.57, 62.44, 64.25, 127.41, 128.75, 130.51, 156.88, 166.74, 166.70, 201.12.

2.2 Synthesis of 4-methoxy-N$^1$,N$^3$-dimethyl-5-(2-thioxo-thiazolidine-3-carbonyl)-isophthalamide (7A)

To a solution of compound 6A in dichloromethane, a mixture of 1 mL methylamine solution (40% wt in water, d=0.902) and isopropanol (10 mL) was added dropwise over 48 h. The reaction mixture was applied directly onto a gradient flash silica column (1-5% methanol in dicholoromethane). The desired product was obtained as a thick, yellow oil. Yield 2.9 g (68% based on methylamine).

$^1$H NMR (500 MHz, CDCl$_3$, 25° C.): □2.814 (d+d, 3+3H, J=4.5, NCH$_3$), 3.330 (t, 3H, J=7.5 Hz, CH$_2$), 3.791 (s, 3H, CH$_3$), 4.513 (t, 2H, J=7.0 Hz, CH$_2$), 7.538 (q, 1H, J=5 Hz, AmideH), 7.538 (q, 1H, J–5 Hz, AmideH), 7.832 (s, 2H, ArH).

$^{13}$C NMR (500 MHz, CDCl$_3$, 25° C.): □26.82, 29.26, 55.57, 62.44, 64.25, 127.41, 128.75, 130.51, 156.88, 166.74, 166.70, 201.12.

(+)-FABMS (TG/G): m/Z: 368 [MH$^+$]

2.3 Synthesis of 3-[4-methoxy-3,5-bis-(2-thioxo-thiazolidine-3-carbonyl)-benzoylamino]-propionic acid ethyl ester (6B)

To slurry of the 2-methoxy-TIAM-trithiazolide 5 (27.1 g, 0.05 mol) and triethylamine (2 mL) in dichloromethane (600 mL), a solution of □-alanine ethyl ester HCl salt (1.1 g, 7 mmol) in DMF (15 mL) and dichloromethane (100 mL) was added dropwise over 36 h. The reaction mixture was applied directly onto a gradient flash silica column (1-3% methanol in dichloromethane). The desired product was obtained as thick, yellow oil. Yield 2.3 g (61% based on the □-alanine ethyl ester HCl salt).

¹H NMR (300 MHz, CDCl₃, 25° C.): □1.253 (t, 3H, J=7.2 Hz, ala-esterCH₃), 2.613 (t, 2H, J=6.0 Hz, alaCH₂), 3.432 (t, 4H, J=7.3 Hz, thiazCH₂), 3.667 (q, 2H, J=6.0 Hz, alaCH₂), 3.903 (s, 3H, CH₃), 4.146 (q, 2H, J=7.0 Hz, ala-esterCH₂), 4.597 (t, 4H, J=7.3 Hz, thiazCH₂), 6.922 (t, 1H, J=6.0 Hz, AmideH), 7.796 (s, 3H, ArH).
¹³C NMR (500 MHz, CDCl₃, 25° C.): □ 14.02, 29.17, 33.70, 35.44, 55.47, 60.66, 62.36, 127.37, 128.35, 130.35, 156.84, 164.70, 166.52, 173.41, 200.98.
(+)-FABMS (TG/G): m/Z: 542.0 [MH⁺].

2.4 Synthesis of 3-[4-methoxy-3-methylcarbamoyl-5-(2-thioxo-thiazolidine-3-carbonyl)-benzoylamino]-propionic acid ethyl ester (7B)

To a solution of compound 6B (2.3 g, 4.25 mmol) in dichloromethane, a mixture of 0.2 mL methylamine solution (40% wt in water, d=0.902) and 10 mL isopropanol was added dropwise over 24 h, the completeness of reaction was monitored by TLC. The reaction mixture was then directly applied onto a gradient flash silica column (1-5% methanol in dichloromethane). The desired product was obtained as a thick, yellow oil.
Yield 1.5 g (67%).
¹H NMR (300 MHz, CDCl₃, 25° C.): □0.963 (t, 3H, J=7.2 Hz, ala-esterCH₃), 2.376 (t, 2H, J=6.0 Hz, alaCH₂), 2.686 (m, 5H, CH₃+CH₂), 3.214 (t, 4H, J=7.3 Hz, thiazCH₂), 3.393 (q, 2H, J=6.0 Hz, alaCH₂), 3.645 (s, 3H, CH₃), 3.840 (q, 2H, J=7.0 Hz, ala-esterCH₂), 4.379 (t, 4H, J=7.3 Hz, thiazCH₂), 6.947 (t, 1H, J=4.5 Hz, AmideH), 7.425 (s, 1H, AmideH), 7.719 (s, 1H, ArH), 8.415 (s, 1H, ArH).
¹³C NMR (500 MHz, CDCl₃, 25° C.): 013.96, 26.61, 29.05, 31.14, 33.77, 35.68, 36.33, 55.59, 60.38, 62.52, 126.81, 128.70, 129.39, 130.89, 131.57, 157.27, 162.53, 165.08, 165.13, 166.55, 171.82, 201.71.
(+)-FABMS (can+NBA): m/Z: 454.1 [MH⁺].

2.5 Synthesis of {3-[4-methoxy-3,5-bis-(2-thioxo-thiazolidine-3-carbonyl)-benzoylamino]-propyl}-carbamic acid benzyl ester (6C)

To a slurry of trithiazolide 5 (27.1 g, 0.05 mol) and triethylamine (3 mL) in dichloromethane (600 mL), a solution of N—Z-1,3-diaminepropane hydrochloride (CBZ3LI-amine HCl salt) (2.0 g, 8.2 mmol) in methanol (10 mL) and dichloromethane (150 mL) was added dropwise over 48 h. The reaction mixture was directly applied onto a gradient flash silica column (1-3% methanol in dichloromethane). The desired product was obtained as thick, yellow oil. Yield 4.9 g (77% based on the CBZ3LI-amine HCl salt). 20.7 g of unreacted starting trithiazolide was recovered during the separation.
¹H NMR (500 MHz, CDCl₃, 25° C.): □1.654 (qint, 2H, J=6.0, Hz, CH₂), 3.260 (q, 2H, J=6.0 Hz, NCH₃), 3.347 (t, 4H, J=7.2 Hz, CH₂), 3.379 (q, 2H, J=6.0 Hz, CH₂), 3.889 (s, 3H, CH₃), 4.538 (t, 4H, J=7.5 Hz, CH₂), 5.082 (s, 2H, □CH₂), 5.467 (t, 1H, J=6.0 Hz, AmideH), 7.25-7.32 (m, 5H, ArH), 7.366 (q, 1H, J=5.0 Hz, AmideH), 7.905 (s, 2H, ArH).
¹³C NMR (500 MHz, CDCl₃, 25° C.): □29.20, 29.68, 36.25, 37.56, 55.55, 62.44, 66.59, 127.41, 127.77, 127.98, 128.42, 130.53, 136.47, 157.05, 157.15, 164.98, 166.71, 201.04.
(+)-FABMS (TG/G): m/Z: 633.0 [MH⁺]

2.6 Synthesis of {3-[4-methoxy-3-methylcarbamoyl-5-(2-thioxo-thiazolidine-3-carbonyl)-benzoylamino]-propyl}-carbamic acid benzyl ester (7C)

Compound 7C was prepared by the same procedure as compound 7A except compound 6C was used instead of compound 6A. Separation and purification were performed as described for compound 7A, pure material was obtained as a thick, bright yellow oil, yield: 71%.
¹H NMR (500 MHz, CDCl₃, 25° C.): □ 1.606 (qint, 2H, J=6.0, Hz, CH₂), 2.829 (d, 3H, J=5.0 Hz, CH₃), 3.099 (q, 2H, J=6.0 Hz, NCH₃), 3.129 (s, 3H, CH₃), 3.279 (t, 4H, J=7.2 Hz, CH₂), 3.313 (q, 2H, J=6.0 Hz, CH₂), 3.772 (s, 3H, CH₃), 4.479 (t, 4H, J=7.5 Hz, CH₂), 4.960 (s, 2H, □CH₂), 5.994 (t, 1H, J=6.0 Hz, AmideH), 7.14-7.21 (m, 5H, ArH), 7.525 (q, 1H, J=5.0 Hz, AmideH), 7.820 (q, 1H, J=6.0 Hz, AmideH), 7.851 (s, 2H, ArH), 8.318 (s, 2H, ArH).
¹³C NMR (500 MHz, CDCl₃, 25° C.): □29.02, 29.76, 36.64, 37.73, 52.50, 55.55, 62.85, 66.56, 127.94, 128.41, 129.03, 129.84, 131.40, 136.60, 157.68, 164.96, 165.46, 166.78, 201.53.
(+)-FABMS (TG/G): m/Z: 545 [MH⁺].

Example 3

Set forth herein are representative synthetic procedures for the conjugation of the activated a 2-methoxy-1,3,5-tris-(2-thioxo-thiazolidine-3-carbonyl)-benzene core to a polyamine core. An exemplary synthetic scheme is provided in Scheme 3.

3.1 Synthesis of Me₄H(2,2)TIAM (8A)

To a solution of H(2,2)-amine (0.5 mmol) in CH₂Cl₂ (50 mL), 7A (0.81 g, 2.2 mmol) was added. The mixture was stirred until TLC indicated that the reaction was complete. The reaction mixture was applied to a gradient flash silica gel column (2-7% CH₃OH in CH₂Cl₂), and the appropriate fractions were evaporated to dryness to give 0.50 g (82%) pure product as white foam.
¹H NMR (500 MHz, CDCl₃,): □□2.753 (s, 4H, CH2), 2.775 (qint, br, 8H, J=7.5 Hz, CH₂), 2.844 (d, 12H, J=5.0 Hz, CH₃), 2.972 (d, 12H, J=5.0 Hz, CH₃), 3.545 (q, 8H, J=6.5 Hz, CH₂), 3.804 (s, 12H, CH₃), 7.704 (d, br, 4H, J=2.5 Hz, ArH), 7.668 (t, br, 4H, J=2.5 Hz, ArH), 7.692 (t, br, 4+4H, J=7.0 Hz, AmideH), 7.842 (t, br, 2H, J=5.8 Hz, AmideH).
¹³C NMR (500 MHz, CDCl₃) □□26.28, 26.32, 37.49, 53.13, 62.27, 64.95, 129.07, 129.56, 129.83, 129.98, 130.04, 156.79, 165.06, 165.32, 165.99.
(+)-FABMS (TG/G): m/Z: 1225 [MH⁺].

3.2 Synthesis of H₄H(2,2)TIAM (9A)

Compound 8A (1 g, 0.82 mmol) was suspended in dry degassed CH₂Cl₂ (30 mL). The solution was cooled in an ice bath and BBr₃ (2 mL, 22.8 mmol) was added via syringe under nitrogen. The resultant pale yellow slurry was stirred for 64 hrs, after which the volatile was removed under vacuum and the residue was quenched with methanol (30 mL). The methanol solution was diluted with water (40 mL) and refluxed until a colorless transparent solution was obtained; the volume of which was reduced to 10 mL. The solution was cooled, and white precipitate deposited, which was collected by filtration and vacuum dried. Yield: 70%.
¹H NMR (500 MHz, D₂O—NaOD): □□2.583 (s, 12H, CH₃), 2.647 (q, br, 8H, J=6.0 Hz, CH₂), 2.705 (s, 12H, CH₃), 2.755 (s, br, 4H, CH₂), 3.300 (t, 8H, J=6.5 Hz, CH₂), 7.852 (d, 4H, J=2.5 Hz, ArH), 7.872 (d, 4H, J=2.5 Hz, ArH).
¹H NMR (500 MHz, DMSO-d₆): □□2.755 (d, 12H, J=4.5 Hz, CH₃), 2.805 (d, 12H, J=4.5 Hz, CH₃), 3.467 (s, br, 8H, CH₂), 3.754 (s, br, 12H, CH₂), 8.406 (d, 4H, J=4.5 Hz, AmideH), 8.491 (s, 4H, ArH), 8.539 (s, 4H, ArH). 8.905 (s, br, 4H, AmideH), 9.029 (s, br, 4H, AmideH).

(+)-FABMS (NBA): m/Z: 1169.4 [MH$^+$].

Calcd. (Found) for $C_{54}H_{68}N_{14}O_{16} \cdot 2HBr \cdot 2H_2O$ (1367.06): C, 47.44 (47.21); H, 5.45 (5.59); N, 14.34 (13.09).

3.2(a) Characterization

3.2(a)(1) Absorbance of the Complex 9A

The UV/Vis spectrum of complex 9A includes and extra band in addition to those found in the spectra of the lanthanide complexes of salicylamide and 2-hydroxyisophthalamide chelating units; the additional band is centered around 275 nm. This absorbance band has been demonstrated to be efficient for the excitation of lanthanide metal ion. The molar absorptivity is between about 15,000 and 25,000.

Figure 1B:
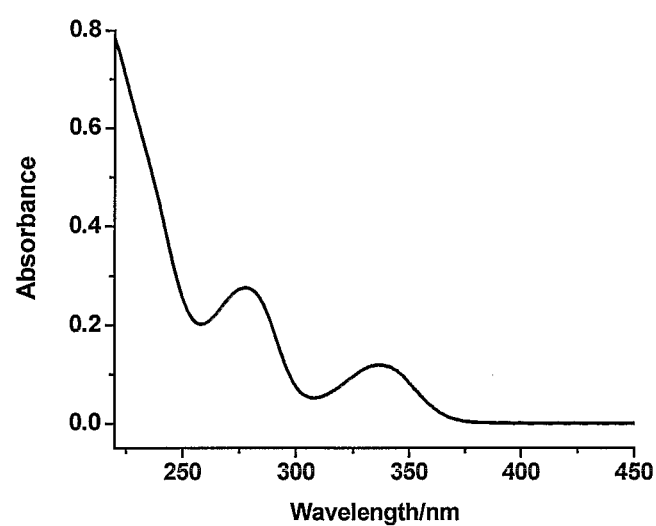

The absorbance spectra of Tb complexes formed with the ligands H22TAMDIAM (9A) and H22tetra3LITIAM (9G) are very similar, indicating that the different group of the para amide does not have a strong effect on the electronic structure of the resulting complexes. FIG. 2 shows the absorption spectra of aqueous solutions of the Tb complexes formed with the ligands H22MeTIAM (9A) (FIG. 1A) and H22tetra3LITIAM (9G) (FIG. 1B).

3.2(a)$_2$ Luminescence of the Complexes

Figure 2A:
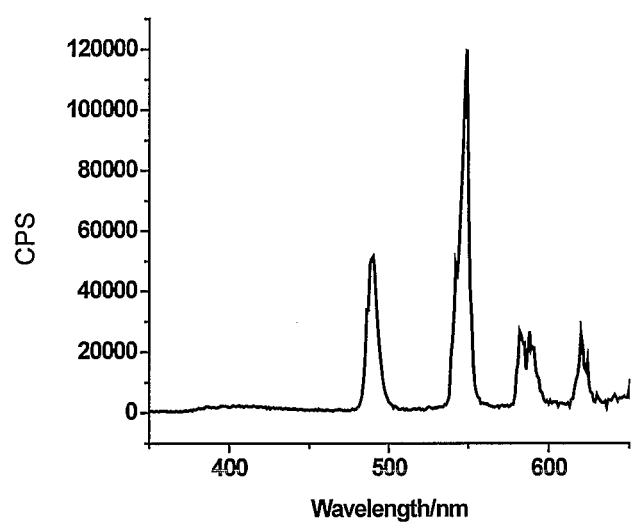
FIG. 2 Emission spectra of the Tb complexes formed with the ligands H22MeTIAM (9A) (FIG. 2A) and H22tetra3LITIAM (9G) (FIG. 2B). These spectra have been recorded upon on aqueous solutions upon excitation at 340 nm.
Figure 2B:
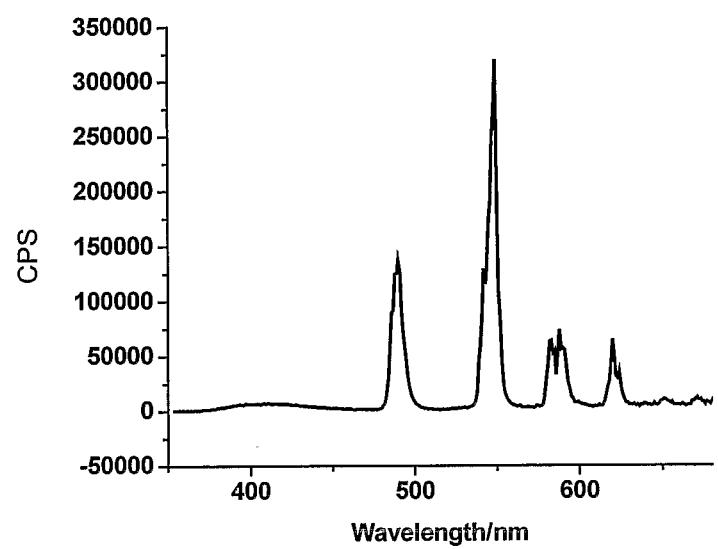

When the triamide ligand complexes a lanthanide cation, the emission of the ligand is replaced by the sharp emission arising from the lanthanide cation. FIG. 2 shows the emission spectra of the Tb complexes formed with the ligands H22MeTAM (9A) (FIG. 2A) and H22tetra3LITIAM (9G) (FIG. 2B). These spectra have been recorded upon on aqueous solutions upon excitation at 340 nm. The absence of ligand emission indicates an efficient and directional transfer of energy from the ligand to Tb. The quantum yields of the Tb complexes formed with the ligands 9A and 9B in aqueous solution are greater than 10%.

3.2(a)3 Stability of the Complexes in Aqueous Solution

The stability constants of the lanthanide complexes formed with the ligand H22TAMDIAM(9A) were estimated through spectrophotometric titrations. The values of the first four protonation constants have been attributed to the four phenolic protons and are set forth in Table 2.

TABLE 2

Protonation constants of the ligand H22MeTIAM (9A)

| Proton Affinity | | pK$_a$ | |
|---|---|---|---|
| Log $\square_{011}$ | 8.58(2) | 8.58 | IAM |
| Log $\square_{012}$ | 15.17(3) | 6.59 | IAM |
| Log $\square_{013}$ | 20.38(4) | 5.21 | IAM |
| Log $\square_{014}$ | 24.46(6) | 4.08 | IAM |

Figure 3:
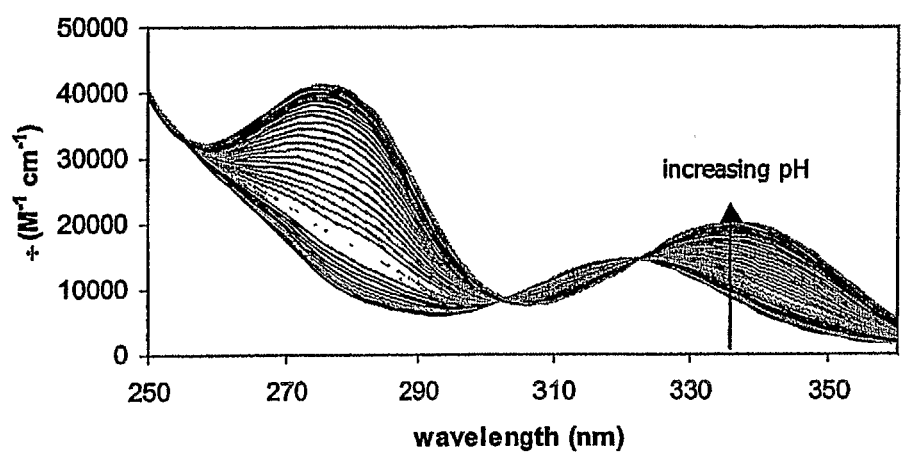
FIG. 3 Spectrophotometric titration of a 1:1 ratio Eu:H22MeTIAM (9A): I=0.1, 25° C., optical path=1 cm.

The spectrophotometric titration of a 1:1 ratio Eu:H22MeTIAM (9A) is shown in FIG. 3. The stability constants of the Eu and Tb complexes formed with the ligand H22TAMDIAM (9A) have been calculated form these experiments and the results are reported in the table.

TABLE 3

Stability constants of the Eu and Tb complexes with the ligand H22MeTIAM (9A)

| Eu, pM = 18.2, n = 3 | | | Tb, pM = 19.7, n = 3 | | |
|---|---|---|---|---|---|
| Log $\square_{110}$ | 17.29(1) | pK$_a$ | Log $\square_{110}$ | 17.85(3) | pK$_a$ |
| Log $\square_{11-1}$ | 11.04(2) | 6.25 | Log $\square_{11-1}$ | 12.60(7) | 5.25 |
| Log $\square_{11-2}$ | 1.98(10) | 9.06 | Log $\square_{11-2}$ | 3.62(9) | 8.98 |

Figure 4A:
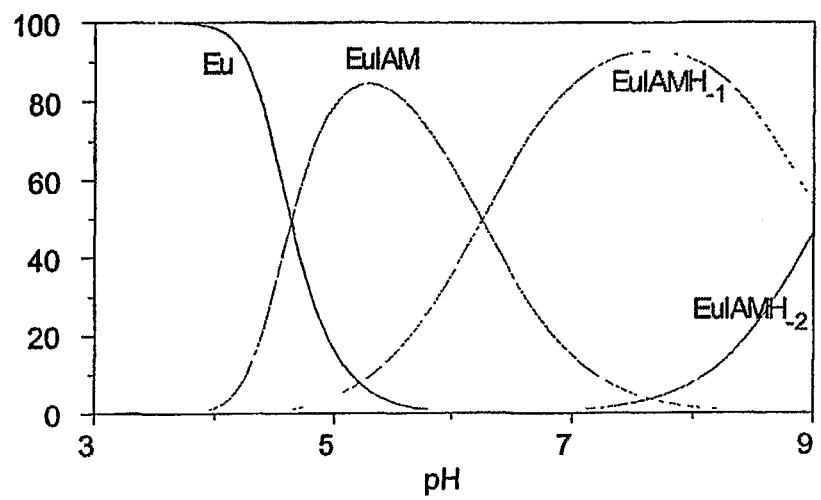
FIG. 4A shows the species distribution of the Eu complexes with the ligand H22MeTIAM (9A) at nanomolar concentration.
Figure 4B:
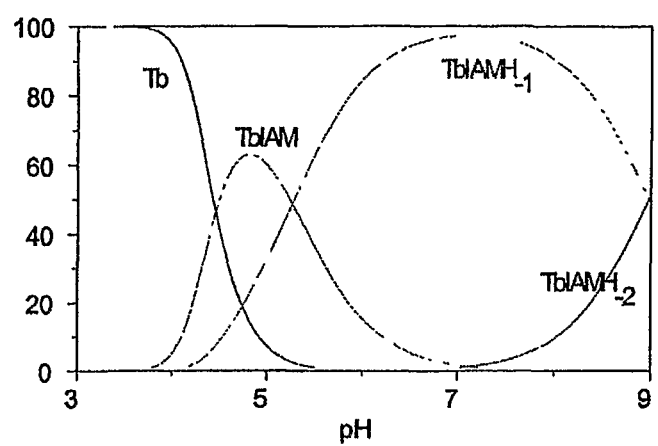
FIG. 4B shows the species distribution of the Tb complexes with the ligand H22MeTIAM (9A) at nanomolar concentration.

The stability constants of both complexes indicate that these luminescent species can be used at very low concentration over a wide range of pH as exemplified by the species distribution calculated for the Tb and Eu complexes at nanomolar concentration (FIG. 4). According to the stability constants, the Eu complex is less stable than the Tb complex formed with the same ligand, allowing discrimination between lanthanides based upon their size.

3.3 Synthesis of Me$_4$H(2,2)TIAM-Tetra-Alanine Ethyl Ester (8D)

To a solution of 0.2 mmol of H(2,2)-amine in CH$_2$Cl$_2$ (50 mL), compound 7B (0.45 g, 1 mmol) was added, the mixture was stirred until TLC indicate the reaction was finished. The reaction mixture was applied to a gradient flash silica gel column (2-7% CH$_3$OH in CH$_2$Cl$_2$), and the appropriate fractions of were evaporated to dryness to give 0.24 g (77%) pure product as white foam.

$^1$H NMR (500 MHz, CDCl$_3$, 25° C.): $\square$1.113 (t, 12H, J=7.0 Hz, ala-esterCH$_3$), 2.493 (s, br, 8H, alaCH$_2$), 2.615 (s, br, 8H, CH$_2$), 2.708 (s, 4H, ethylene bridgeH), 2.790 (m, 8H, CH$_2$), 3.329 (s, br, 8H, alaCH$_2$), 3.460 (s, br, 8H, CH$_2$), 3.664 (s, 12H, NHCH$_3$), 3.985 (q, 8H, J=7.0 Hz, ala-esterCH$_2$), 7.690 (s, 4H, AmideH), 7.724 (s, 8H, ArH), 7.830 (s, br, 4H, AmideH).

$^{13}$C NMR (500 MHz, CDCl$_3$, 25° C.): 013.84, 24.97, 26.43, 31.05, 33.53, 35.59, 36.20, 37.61, 60.39, 62.27, 127.72, 128.04, 128.98, 130.78, 157.16, 162.33, 165.41, 165.57, 165.82, 171.

(+)-FABMS (TG/G): m/Z: 1569.3 [MH$^+$].

3.4 Synthesis of Me$_4$H(2,2)TIAM-tetra-alanine (9D)

Me$_4$H(2,2)TIAM-tetra-alanine ethyl ester 8B (0.24 g, 0.15 mmol) was dissolved in dry degassed CH$_2$Cl$_2$ (20 mL). The solution was cooled in an ice bath and BBr$_3$ (0.5 mL, 4.2 mmol) was added via syringe under nitrogen. The resulting pale yellow slurry was stirred for 64 h, after which the volatiles were removed under vacuum and the residue was quenched with methanol (30 mL). The methanol solution was diluted with water (40 mL) and boiled until a colorless transparent solution was obtained; the volume was reduced to 10 mL. The solution was cooled, and white precipitate deposited, which was collected by filtration and vacuum dried. Yield: 70%.

$^1$H NMR (500 MHz, DMSO-d$_6$, 25° C.): $\square$2.535 (t, 8H, J=5.6 Hz, ala CH$_2$), 2.796 (d, 12H, J=4.3 Hz, NHCH$_3$), 3.469 (q, 8H, J=6.4 Hz, CH$_2$), 3.5843 (s, 14H, ethylene bridgeH+ CH$_3$), 3.729 (m, 8H, CH$_2$), 8.464 (s, br, 8H, ArH), 8.544 (t, 4H, AmideH), 8.863 (s, 8H, AmideH), 8.993 (s, br, 4H, AmideH).

(+)-FABMS (TG/G): m/Z: 1401.5 [MH$^+$].

3.5 Synthesis of Me$_4$H(2,2)Z$_4$3LITIAM (8G)

Compound 8C was prepared by the same procedure as compound 8A except 7C was used instead of 7A. Separation and purification were performed as described for compound 8A, pure material was obtained as white foam, yield: 72%.

$^1$H NMR (500 MHz, CDCl$_3$): □□1.605 (s, br, 8H, CH$_2$), 2.618 (s, br, 4H+8H, CH$_2$), 2.807 (s, br, 12H, NCH$_2$), 3.092 (s, br, 8H, CH$_2$), 3.257 (s, br, 8H, CH$_2$), 3.335 (s, br, 8H, CH$_2$), 3.697 (s, 12H, OCH$_3$), 4.987 (s, br, 8H, □ArH), 5.985 (s, br, 4H, Z-amideH), 7.244 (s, br, 20H, Z—ArH), 7.666 (s, br, 8H, Amide+ArH), 7.822 (s, br, 4H, AmideH), 7.908 (s, br, 8H, ArH+AmideH).

$^{13}$C NMR (500 MHz, CDCl$_3$) □□25.09, 26.54, 29.33, 36.75, 37.81, 45.95, 50.12, 62.29, 66.29, 127.37, 127.73, 127.81, 128.09, 128.25, 129.17, 130.81, 136.45, 156.68, 157.20, 165.64, 166.08, 166.18.

(+)-FABMS (TG/G): m/Z: 1934.8 [MH$^+$].

3.6 Synthesis of H$_4$H(2,2)tetra3LITIAM (9G)

Compound 9C was deprotected in the same BBr$_3$ deprotection procedure as mentioned for compound 9A. Because this compound was obtained as a salt of hexa hydrobromic acid, only methanol was used as the solvent to get the final product. A beige solid was obtained as final product, yield 81%.

$^1$H NMR (500 MHz, D$_2$O—NaOD): □□1.440 (qint, 8H, J=7.0 Hz, CH$_2$), 2.396 (t, 8H, J=7.0 Hz, CH$_2$), 2.525 (s, 12H, CH$_3$), 2.545 (s, br, 8H, CH$_2$), 2.623 (s, 4H, CH$_2$), 3.077 (t, 8H, J=7.0 Hz, CH$_2$), 3.173 (s, 8H, CH$_2$), 7.769 (d, 4H, J=3.0 Hz, ArH), 7.784 (d, 4H, J=3.0 Hz, ArH).

(+)—FABMS (NBA): m/Z: 1341.9 [MH$^+$].

Calcd. (Found) for C$_{62}$H$_{88}$N$_{18}$O$_{16}$.6HBr.4H$_2$O (1899.0): C, 39.21 (39.33); H, 5.41 (5.48); N, 13.34 (13.06).

3.7 Synthesis of Me$_3$H(2,2)-triMeTIAM-monoamine (10A)

To a solution of H(2,2)-amine (0.50 g, 2 mmol) in CH$_2$Cl$_2$ (150 mL), a solution of 4-Methoxy-N1,N3-dimethyl-5-(2-thioxo-thiazolidine-3-carbonyl)-isophthalamide (7A) (2.2 g, 6 mmol) in CH$_2$Cl$_2$ (150 mL) was added dropwise over 48 h, and the mixture was stirred for another 2 h. The reaction mixture was loaded on a flash silica gel column and eluted with 5-15% isopropanol+0.5% TEA in CH$_2$Cl$_2$ to give 0.99 g (50%) of the pure product as white foam.

$^1$H NMR (500 MHz, CD$_3$OD, 25° C.): □2.693 (t, br, 4H, J=6.0, CH$_2$), 2.754 (s, br, 4H, CH$_2$), 2.806 (t, 4H, J=5.5, CH$_2$), 2.829 (t, 2H, J=5.5, CH$_2$), 2.850 (s, 3H, CH$_3$), 2.867 (s, 6H, CH$_3$), 2.916 (s, 3H, CH$_3$), 2.928 (s, 6H, CH$_3$), 3.500 (t, 6H, J=6.0, CH$_2$), 3.861 (s, 6H, CH$_3$), 3.885 (s, 3H, CH$_3$), 8.048 (d, 2H, J=2.5, ArH), 8.069 (d, 2H, J=2.5, ArH), 8.089 (d, 1H, J=2.5, ArH), 8.136 (d, 1H, J=2.5, ArH).

$^{13}$C NMR (500 MHz, CD$_3$OD, 25° C.): □□26.98, 39.02, 39.73, 49.85, 53.32, 53.44, 54.39, 54.83, 56.38, 63.35, 63.40, 130.09, 130.24, 130.37, 130.41, 130.58, 130.67, 131.95, 132.24, 159.09, 167.79, 167.97, 168.07, 168.42.

(+)-FABMS (NBA): m/Z: 977 [MH$^+$].

3.8 Synthesis of Me$_4$monoCBZ$^3$LIamino-H(2,2) TIAM (11B)

To a solution of compound 10A (0.98 g, 1 mmol) in CH$_2$Cl$_2$ (50 mL), compound 7C (0.60 g, 1.1 mmol) was added, and the mixture was stirred until TLC indicated that the reaction was complete. The reaction mixture was applied to a gradient flash silica gel column (2-7% CH$_3$OH in CH$_2$Cl$_2$), and the appropriate fractions were collected and evaporated to dryness to give 1.2 g (75%) of the pure product as a white foam.

$^1$H NMR (500 MHz, CD$_3$OD+CDCl$_3$, 25° C.): □1.748 (quint, J=7.0, 2H, CH$_2$), 2.808 (s, br, 9H, CH$_3$), 2.841 (s, br, 12H, CH$_3$), 2.907 (s, br, 12H, CH$_3$), 3.191 (t, J=7.5, 2H, CH$_2$), 3.509 (s, br, 8H, CH$_2$), 3.166 (s, 9H, CH$_3$), 3.858 (s, 12H, CH$_3$), 5.038 (s, 2H, CH$_2$), 7.2-7.4 (m, 5H, benzylArH), 8.03-8.08 (m, 8H, ArH).

$^{13}$C NMR (500 MHz, CD$_3$OD, 25° C.): □□25.08, 25.21, 28.38, 36.19, 36.82, 37.08, 47.99, 51.06, 52.16, 61.34, 65.23, 126.55, 126.78, 127.27, 127.52, 127.75, 128.38, 130.00, 130.18, 135.93, 156.52, 156.84, 165.35, 165.44, 165.80, 165.98, 166.08.

(+)-FABMS (NBA): m/Z: 1402.7 [MH$^+$].

3.9 Synthesis of H$_4$mono-3LIamino-H(2,2)TIAM (12B)

Compound 11B was deprotected in a standard BBr$_3$ deprotection procedure as mentioned for compound 9G. A beige solid was obtained as the final product, yield 81%.

$^1$H NMR (500 MHz, D$_2$O—NaOD): □□1.248 (quint, J=7.0, 2H, CH$_2$), 1.740 (qint, 6H, J=7.0 Hz, CH$_2$), 2.376 (t, 8H, J=7.0 Hz, CH$_2$), 2.425 (s, 12H, CH$_3$), 2.575 (s, br, 8H, CH$_2$), 2.723 (s, 4H, CH$_2$), 3.177 (t, 8H, J=7.0 Hz, CH$_2$), 3.293 (s, 8H, CH$_2$), 3.391 (t, J=7.5, 2H, CH$_2$), 7.769 (d, 4H, J=3.0 Hz, ArH), 7.784 (d, 4H, J=3.0 Hz, ArH).

(+)-FABMS (NBA): m/Z: 1212.5 [MH$^+$].

Calcd. (Found) for C$_{56}$H$_{73}$N$_{15}$O$_{16}$.6HBr2.5H$_2$O (1899.0): C, 38.58 (38.33); H, 4.86 (4.48); N, 12.05 (11.86).

3.10 Synthesis of 2-hydroxy-benzene-1,3,5-tricarboxylic acid (13)

A mixture of 2-methoxy-benzene-1,3,5-tricarboxylic acid (3) (24 g, 0.1 mol) and 48% HBr (500 mL) was placed in a 1 L bound bottom flask. The reaction mixture was heated to reflux at 150° C. for 48 h. The progress of the deprotection was monitored by proton NMR. When the reaction was complete, the hydrobromic acid was removed under reduced pressure, and the residue was mixed with small amount of water. The deprotected triacid (13) was collected by filtration; yield 17 grams (75%).

$^1$H NMR (500 MHz, D2O—NaOD, 25° C.): □7.959 (s, 2H, ArH).

$^{13}$C NMR (125 MHz, DMSO-d$_6$, 25° C.): □117.03, 130.15, 130.40, 166.86, 176.02, 179.10.

3.11 Synthesis of 2-benzyloxy-benzene-1,3,5-tricarboxylic acid tribenzyl ester (14)

Compound 13 (22.6 g, 0.1 mol), benzyl chloride (57 g, 0.46 mol) and anhydrous potassium carbonate (120 g, 0.87 mol) were mixed in dry DMF (500 mL). The mixture was heated at 75° C. while stirring under nitrogen overnight. TLC confirmed that the reaction was complete. The reaction mixture was cooled, filtered, and the filtrate was evaporated to remove the volatiles. The residue was dissolved in 1 L of recycling [?] methylene chloride and a silica gel plug was used to remove some impurities with low R$_f$. The fully benzyl-protected product was obtained as a thick, yellow oil after removing the solvent: raw yield 53 g (90%).

$^1$H NMR (500 MHz, CDCl$_3$) □4.619 (s, 1H, benzyl CH$_2$), 5.131 (s, 1H, benzyl CH$_2$), 5.226 (s, 1H, benzyl CH$_2$), 5.361 (s, 2H, benzyl CH$_2$), 5.402 (s, 1H, benzyl CH$_2$), 5.416 (s, 1H, benzyl CH$_2$), 5.452 (s, 1H, benzyl CH$_2$), 7.30-7.52 (m, 20H, ArH), 8.690 (s, 1H, ArH), 8.833 (s, 1H, ArH).

¹³C NMR (125 MHz, CDCl₃) □: 66.85, 67.08, 67.33, 67.36, 69.56, 71.69, 78.09, 116.63, 120.63, 125.52, 127.63, 128.14, 128.18, 128.19, 128.23, 128.27, 128.30, 128.31, 128.35, 128.38, 128.44, 128.48, 128.50, 128.53, 128.56, 135.06, 135.17, 135.94, 136.08, 138.16, 154.95, 161.21, 164.43, 164.63, 164.88, 164.64.

3.12 Synthesis of 2-benzyloxy-benzene-1,3,5-tricarboxylic acid (15)

2-Benzyloxy-benzene-1,3,5-tricarboxylic acid tribenzyl ester (14) (52 g, 88 mmol) was hydrolyzed with NaOH (20 g, 0.5 mol) in 4:1 methanol-water (1 L). The solvents were removed under reduced pressure after the completion of hydrolysis, and the residue was dissolved in saline and extracted with recycling methylene chloride to remove the benzyl alcohol. 2-benzyloxy benzene-1,3,5-tricarboxylic acid (15) deposited after acidification of the solution. It was collected by filtration and dried under vacuum, yield 25.6 g, 92%.

¹H NMR (500 MHz, D₂O—NaOD, 25° C.) □: 5.08 (s, 2H, benzyl CH₂), 7.30-7.47 (m, 3H, ArH), 7.456 (d, 2H, J=7.0 Hz, ArH), 8.351 (s, 2H, ArH).

¹³C NMR (125 MHz, D₂O—NaOD, 25° C.), □: 76.30, 128.39, 128.54, 128.65, 128.76, 133.88, 152.79, 174.07, 175.44.

3.13 Synthesis of [2-benzyloxy-3,5-bis-(2-thioxo-thiazolidine-3-carbonyl)-phenyl]-(2-thioxo-thiazolidin-3-yl)-methanone (17)

To a solution of compound 15 (25.3 g, 80 mmol) in dry benzene, excess oxalyl chloride (38 g, 0.3 mol) and a drop of DMF were added with stirring. The mixture was kept at 60° overnight under N₂. The volatiles were then removed under reduced pressure. The residue was co-evaporated with dry THF (50 mL) and dissolved in dry THF (200 mL). To this pale yellow solution, 2-mercaptothiazoline (36 g, 0.3 mol) and 40 mL of triethylamine in 200 mL dry THF were added dropwise with stirring and cooling. The reaction immediately turned yellow and the resulting thick, yellow slurry was stirred overnight and then filtered. The yellow filtrate was evaporated to dryness, dissolved in CH₂Cl₂, extracted with 1N HCl and 1N KOH successively, then purified by flash chromatography to give 39 g of product, yield: 71%.

¹H NMR (500 MHz, CDCl₃, 25° C.) □: 3.079 (t, J=7.5, 4H, CH₂), 3.486 (t, J=7.5, 2H, CH₂), 4.448 (t, J=7.5, 4H, CH₂), 4.523 (t, J=7.5, 2H, CH₂), 5.082 (s, 2H, BnCH₂), 7.36-7.42 (m, 5H, ArH), 7.827 (d, J=7.5, 2H, ArH).

¹³C NMR (500 MHz, CDCl₃, 25° C.) L 28.95, 30.12, 55.81, 56.99, 75.74, 127.87, 128.03, 128.16, 128.42, 128.52, 132.37, 136.12, 155.53, 165.89, 169.12, 201.83.

3.14 Synthesis of 4-benzyloxy-N-(2-methoxy-ethyl)-3,5-bis-(2-thioxo-thiazolidine-3-carbonyl)-benzamide (18A)

To a slurry of the trithiazolide 17 (31.0 g, 0.05 mol) in dichloromethane (600 mL), a solution of 2-methoxyethylamine (0.38 g, 5 mmol) in dichloromethane (30 mL) was added dropwise over 48 h. The reaction mixture was applied directly onto a gradient flash silica column (1-5% methanol in methylene chloride). The desired product was obtained as yellow, thick oil; yield 2.1 g (73% based on the methoxyethylamine). 25.8 g of unreacted starting trithiazolide was also recovered during the separation.

¹H NMR (500 MHz, CDCl₃, 25° C.): □3.005 (d, 4H, J=6.5, NCH₂), 3.302 (s, 3H, CH₃), 3.487 (s, br, 2H, NHCH₂), 3.544 (s, br, 2H, OCH₂), 4.368 (t, 4H, J=7.0 Hz, CH₂), 4.993 (s, 2H, □CH₂), 6.963 (s, 1H, AmideH), 7.037 (m, 5H, ArH), 7.865 (s, 2H, ArH).

¹³C NMR (500 MHz, CDCl₃, 25° C.): □28.74, 39.69, 55.45, 58.58, 70.73, 76.52, 127.85, 128.04, 128.34, 128.41, 128.83, 130.53, 136.10, 155.37, 162.40, 166.71, 200.94.

3.15 Synthesis of 4-Benzyloxy-N1-(2-methoxy-ethyl)-N3-methyl-5-(2-thioxo-thiazolidine-3-carbonyl)-isophthalamide (19A)

To a solution of compound 18A (2.1 g, 3.65 mmol) in dichloromethane (100 mL), a solution of 0.1 mL methylamine solution (40% wt in water, d=0.902) and 50 mL dichloromethane was added dropwise over 24 h. The reaction progress was monitored by TLC chromatography. When the reaction was judged complete, the reaction mixture was directly applied to a gradient flash silica column (1-5% methanol in dicholoromethane). The desired product was obtained as yellow, thick oil; yield 1.22 g, (69% based on compound 18A).

¹H NMR (500 MHz, CDCl₃, 25° C.): □2.818 (d, 3H, J=4.5, NCH₃), 3.268 (t, 2H, J=7.5 Hz, CH₂), 3.385 (s, 3H, CH₃), 3.549 (t, 2H, J=5.0 Hz, CH₂), 3.645 (q, 2H, J=5.0 Hz, CH₂), 4.564 (t, 2H, J=7.5 Hz, CH₂), 5.060 (s, 2H, □CH₂), 6.672 (t, br, 1H, AmideH), 7.33-7.44 (m, 5H, ArH), 8.044 (d, 1H, J=2 Hz, ArH), 8.048 (d, 1H, J=2 Hz, ArH).

¹³C NMR (500 MHz, CDCl₃, 25° C.): □26.35, 28.69, 39.75, 55.49, 58.60, 70.73, 77.99, 127.41, 128.10, 128.67, 128.83, 129.54, 130.15, 131.47, 131.76, 135.33, 156.30, 164.58, 164.98, 166.63, 201.47.

(+)-FABMS (TG/G): m/Z: 488 [MH⁺]

3.16 4-benzyloxy-N1,N3-bis-(2-methoxy-ethyl)-5-(2-thioxo-thiazolidine-3-carbonyl)-isophthalamide (19B)

This compound was prepared by the same procedure as compound 18A except the molar ratio of compound 17 and 2-methoxyethylamine was 1:2 instead of compound 17 in large excess. Separation and purification were performed as described for compound 18A. Pure material was obtained as thick, bright, yellow oil; yield: 73%.

¹H NMR (500 MHz, CDCl₃, 25° C.): □3.111 (t, 2H, J=7.0 Hz, NCH₂), 3.180 (s, 3H, CH₃), 3.378 (s, 3H, CH₃), 3.386 (t, 2H, J=5.5 Hz, CH₂), 3.534 (t, t, 4H, J=5.5 Hz, CH₂), 3.364 (q, 2H, J=5.5 Hz, CH₂), 4.479 (t, 2H, J=7.5 Hz, CH₂), 5.077 (s, 2H, □CH₂), 6.694 (s, br, 1H, AmideH), 7.734 (m, 5H, ArH), 7.737 (s, br, 1H, AmideH), 8.028 (s, 1H, ArH), 8.458 (s, 1H, ArH).

¹³C NMR (500 MHz, CDCl₃, 25° C.): 028.43, 39.48, 39.67, 55.40, 58.28, 58.50, 70.31, 70.67, 77.42, 126.87, 127.63, 128.43, 128.47, 129.64, 130.07, 131.46, 131.79, 135.53, 156.19, 163.96, 164.92, 166.46, 201.38.

(+)-FABMS (TG/G): m/Z: 532 [MH⁺]

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications are incorporated herein by reference.

The invention claimed is:

1. A compound having the structure:

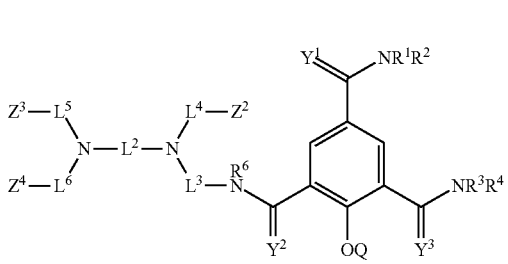

wherein $R^1$, $R^2$, $R^3$, $R^4$, and $R^6$ are members independently selected from H, substituted or unsubstituted alkyl, substituted or unsubstituted heteroalkyl, substituted or unsubstituted aryl, and substituted or unsubstituted heterocycloalkyl, wherein a member selected from $R^1$ and $R^2$; and $R^3$ and $R^4$, together with the nitrogen atom to which they are attached, optionally form a ring system selected from heteroaryl and heterocycloalkyl;

$Y^1$, $Y^2$ and $Y^3$ are members independently selected from O and $(H)_2$, wherein at least one group selected from $Y^1$, $Y^2$ and $Y^3$ is O;

Q is H; a protecting group and a cleavable group;

$L^2$ is a member selected from substituted or unsubstituted alkyl, substituted or unsubstituted heteroalkyl, substituted or unsubstituted aryl, substituted or unsubstituted heteroaryl, substituted or unsubstituted heterocycloalkyl;

$L^3$, $L^4$, $L^5$ and $L^6$ are members independently selected from a single bond, substituted or unsubstituted alkyl and substituted or unsubstituted heteroalkyl; and $Z^2$, $Z^3$, and $Z^4$ are members independently selected from H, substituted or unsubstituted aryl and substituted or unsubstituted heteroaryl.

2. The compound according to claim 1, wherein a member selected from $R^1$ and $R^3$ has the structure:

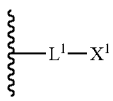

wherein $L^1$ is a member selected from substituted or unsubstituted alkyl, substituted or unsubstituted heteroalkyl and substituted or unsubstituted aryl; and $X^1$ is a member selected from protected or unprotected reactive functional groups.

3. The compound according to claim 2, wherein a member selected from $R^1$ and $R^3$ is a member selected from:

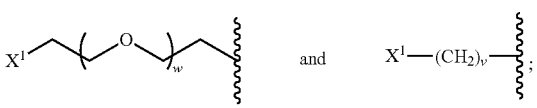

$X^1$ is a member selected from:

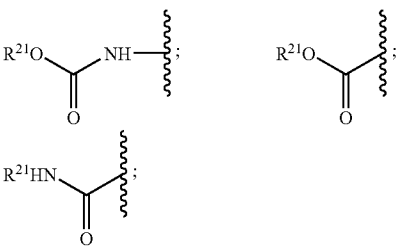

in which $R^{21}$ is a member selected from H, substituted or unsubstituted alkyl and substituted or unsubstituted aryl;

v is an integer from 1 to 20; and w is an integer from 1 to 1,000.

4. The compound according to claim 2 wherein said reactive functional group is a non-covalent protein binding group.

5. The compound according to claim 4, wherein said non-covalent protein binding group is sulfonate.

6. The compound according to claim 1, wherein a member selected from $R^1$ and $R^3$ has the structure:

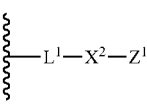

wherein $L^1$ is a member selected from substituted or unsubstituted alkyl and substituted or unsubstituted heteroalkyl; and $X^2$ is a linking member adjoining $L^1$ to $Z^1$; and $Z^1$ is a member selected from carrier molecules and detectable labels.

7. The compound according to claim 6, wherein said carrier molecule is a targeting agent.

8. The compound according to claim 2, wherein $R^1$ has the structure:

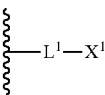

wherein $X^1$ is a member selected from $NH_2$, SH, $COR^7$, $O(CH_2)_m Z^6$, $NHNH_2$ and $O(CH_2)_2(OCH_2CH_2)_s O(CH_2)_2 Z^6$ wherein $R^7$ is a member selected from H, $OR^8$, $OCOR^8$, $NR^8 R^9$, wherein $R^8$ and $R^9$ are members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl;

$Z^6$ is a member selected from $OR^{10}$, $OCOR^{10}$, $NR^{10}R^{11}$ wherein $R^{10}$ and $R^{11}$ are members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl;

m is an integer from 1 to 20; and s is an integer from 1 to 1000.

9. The compound according to claim 1, wherein $Z^2$, $Z^3$, and $Z^4$ are members independently selected from substituted or unsubstituted pyridyl, substituted or unsubstituted salicylamidyl, substituted or unsubstituted phthalamidyl, substituted or unsubstituted terephthalamidyl, substituted or unsubstituted catechol and

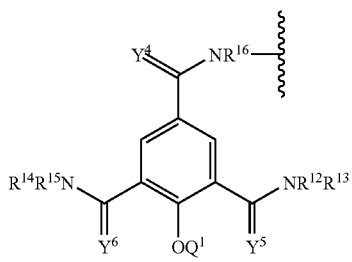

wherein $R^{12}$, $R^{13}$, $R^{14}$, $R^{15}$ and $R^{16}$ are members independently selected from H, substituted or unsubstituted alkyl, substituted or unsubstituted heteroalkyl, substituted or unsubstituted aryl, and substituted or unsubstituted heterocycloalkyl;

$Y^4$, $Y^5$ and $Y^6$ are members independently selected from O and $(H)_2$; and $Q^1$ is H.

10. The compound according to claim 1, wherein $L^2$ is a substituted or unsubstituted $C_1$-$C_6$ alkyl group.

11. The compound according to claim 1, wherein at least one of $R^1$ and $R^3$ has the structure:

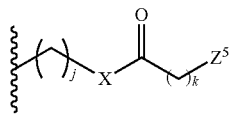

wherein, $Z^5$ is a member selected from H, $OR^{17}$, $SR^{17}$, $NHR^{17}$, $OCOR^{18}$, $OC(O)NHR^{18}$, $NHC(O)OR^{17}$, $OS(O)_2OR^{17}$, and $C(O)R^{18}$;

$R^{17}$ is a member selected from H, substituted or unsubstituted alkyl, and substituted or unsubstituted heteroalkyl;

$R^{18}$ is a member selected from H, $OR^{19}$, $NR^{19}NH_2$, SH, $C(O)R^{19}$, $NR^{19}H$, substituted or unsubstituted alkyl and substituted or unsubstituted heteroalkyl;

$R^{19}$ is a member selected from H, substituted or unsubstituted alkyl and substituted or unsubstituted alkyl;

X is a member selected from O, S and $NR^{20}$ wherein $R^{20}$ is a member selected from H, substituted or unsubstituted alkyl and substituted or unsubstituted heteroalkyl; and j and k are members independently selected from the group consisting of integers from 1 to 20.

12. A polymer comprising a subunit having said structure according to claim 1.

13. The polymer according to claim 12, wherein said polymer is a biomolecule.

14. The polymer according to claim 12, wherein $R^1$ has the structure:

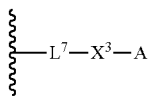

wherein $L^7$ is a member selected from a single bond, substituted or unsubstituted alkyl and substituted or unsubstituted aryl; and $X^3$ is linking member joining $L^7$ to A;

A is a carrier molecule.

15. The polymer according to claim 14, wherein A is a biopolymer; and said biopolymer is a member selected from polypeptides, nucleic acids and saccharides.

16. The polymer according to claim 15, wherein said polypeptide is a member selected from antibodies, enzymes, and serum proteins.

17. A chelate comprising an organic ligand having said structure according to claim 1 and a metal ion.

18. The chelate according to claim 17, wherein said metal ion is a lanthanide ion.

19. The chelate according to claim 18, wherein said chelate is luminescent.

20. The chelate according to claim 17, wherein said chelate is covalently attached to a carrier molecule.

21. A method for detecting enzyme in a sample, said method comprising:
(a) contacting said sample with a peptide construct comprising:
i) a peptide sequence, said sequence comprising a cleavage site for said enzyme;
ii) a complex according to claim 17 covalently bound to said peptide; and
iii) a quencher of light energy covalently bound to said peptide sequence, said quencher having an absorbance band overlapping an emission band of said complex,
wherein said peptide sequence conformation allows light energy transfer between said complex and said quencher when said complex is excited;
(b) exciting said complex;
(c) determining a fluorescence property of said sample; and
(d) comparing said fluorescence property from step (c) with a reference fluorescence property for said peptide construct, wherein said activity of said enzyme in said sample alters said light energy transfer, resulting in a change in said fluorescence property.

22. A method of determining the effect of a compound on enzyme activity, said method comprising:
(a) contacting a sample comprising said enzyme with a peptide construct comprising:
i) a peptide sequence, said sequence comprising a cleavage site for said enzyme;
ii) a complex according to claim 17 covalently bound to said peptide sequence; and
iii) a quencher of light energy covalently bound to said peptide sequence, said quencher having an absorbance band overlapping an emission band of said complex,
wherein said peptide sequence conformation allows light energy transfer between said complex and said quencher when said complex is excited;

(b) exciting said complex;
(c) determining a fluorescence property of said sample; and
(d) comparing said fluorescence property from step (c) with a reference fluorescence property for said peptide construct, wherein said activity of said enzyme in said sample alters said light energy transfer, resulting in a change in said fluorescence property.

23. A method for detecting a target nucleic acid sequence, said method comprising:
(a) contacting said target sequence with a detector oligonucleotide comprising a single-stranded target binding sequence, said detector oligonucleotide having covalently linked thereto,
  i) a complex according to claim 17;
  ii) a quencher of light energy having an absorbance band overlapping an emission band of said complex,
    wherein said detector nucleic acid conformation allows fluorescence energy transfer between said complex and said quencher when said complex is excited;
(b) hybridizing said target binding sequence to said target sequence, thereby altering said conformation of said detector oligonucleotide, causing a change in a fluorescence parameter of said complex; and
(c) determining a fluorescence property of said sample; and
(d) comparing said fluorescence property from step (c) with a reference fluorescence property for said peptide construct, wherein said activity of said enzyme in said sample alters said light energy transfer, resulting in a change in said fluorescence property.

24. The method according to claim 23, wherein said detector oligonucleotide has a format selected from molecular beacons, scorpion probes, sunrise probes, light up probes and TaqMan™ probes.

25. The method according to claim 21, 22 or 23, wherein said fluorescence property is detected in-real time.

26. The method according to claim 21, 22 or 23, wherein said change and said fluorescence property measured is a change in fluorescence intensity.

27. A microarray comprising a complex according to claim 17, wherein said complex is conjugated to a solid support or to a carrier molecule attached to said solid support.

28. The microarray according to claim 27, wherein said carrier molecule is a member selected from a nucleic acid, a peptide, a peptide nucleic acid, a pharmaceutical agent and combinations thereof.

29. The microarray according to claim 27, wherein said solid support is divided into a first region and a second region, said first region having attached thereto a first complex, and said second region having attached thereto a second.

30. A method of providing radiation therapy to a subject requiring such therapy, said method comprising:
administering to said subject a complex according to claim 17, said complex having radiosensitization properties; and
administering ionizing radiation to said subject, thereby providing radiation therapy to said subject.

31. A method for photodynamic therapy of a lesion or of a lesion beneath melanodermic tissue of a subject, said method comprising:
(a) administering a complex according to claim 17 to said subject; and
(b) photoirradiating said lesion.

32. The method according to claim 31, wherein said photoirradiating is with light having a wavelength range of about 610 to about 1150 nanometers.

33. The method of claim 32 wherein the photoirradiating is with light having a wavelength range of about 730 to about 770 nanometers.

34. The chelate according to claim 17, wherein said chelate comprises a fluorophore.

35. The compound of claim 1 wherein $Y^2$ is O.

36. The compound of claim 1 wherein at least two groups selected from $Y^1$, $Y^2$ and $Y^3$ are each O.

37. The compound of claim 1 wherein $Y^1$, $Y^2$ and $Y^3$ are each O.

38. A compound having the structure:

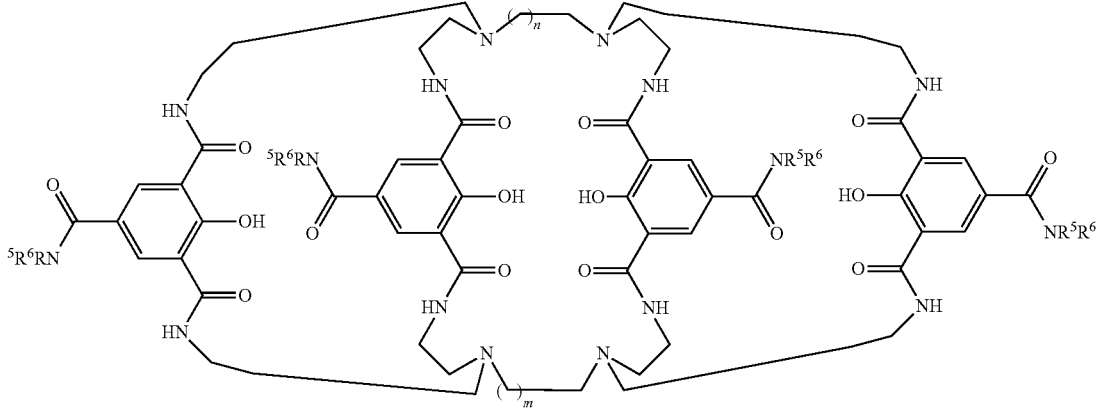

wherein each $R^5$ and each $R^6$ are independently selected from H, substituted or unsubstituted alkyl, substituted or unsubstituted heteroalkyl, substituted or unsubstituted aryl, and substituted or unsubstituted heterocycloalkyl, and wherein $R^5$ and $R^6$, together with the nitrogen atom to which they are attached, optionally form a ring system selected from heteroaryl and heterocycloalkyl; and m and n are independently selected from 1, 2 and 3.

39. The compound of claim 38 wherein each $R^5$ is H.

40. The compound of claim 39 wherein each $R^6$ is independently selected from substituted or unsubstituted alkyl and substituted or unsubstituted heteroalkyl.

41. The compound of claim 40 wherein m and n are each 1.

42. The compound of claim 41 having the structure:
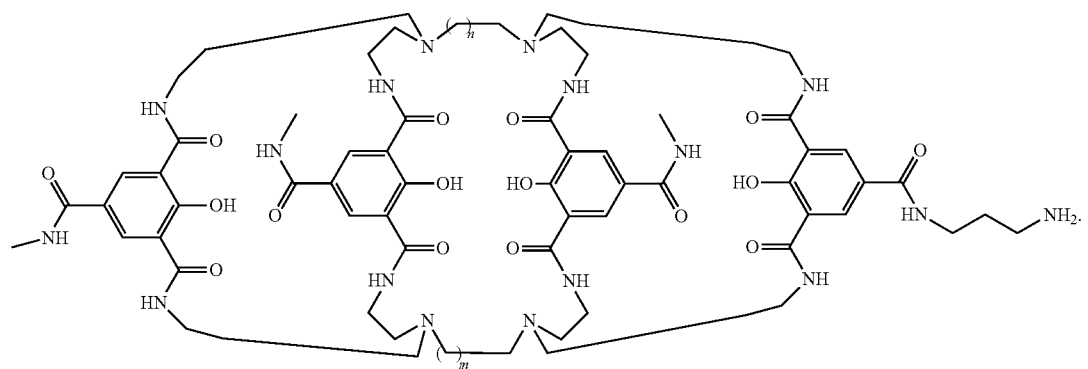
43. The compound of claim 9, wherein $Z^2$, $Z^3$, and $Z^4$ each have the structure:
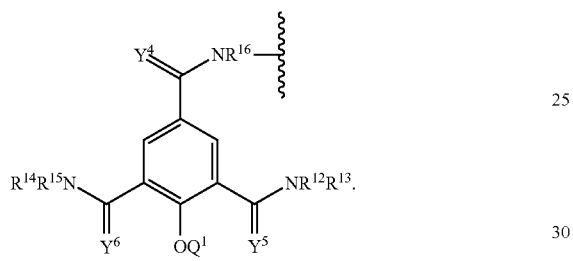
* * * * *